US012466817B2

United States Patent

(12) United States Patent
Luo et al.

(10) Patent No.: US 12,466,817 B2
(45) Date of Patent: Nov. 11, 2025

(54) PYRIDINE DERIVATIVE AND APPLICATION THEREOF

(71) Applicant: Nicoya Therapeutics (Shanghai) Co., Ltd, Shanghai (CN)

(72) Inventors: Yunfu Luo, Shanghai (CN); Yuyong Ba, Shanghai (CN); Shuhui Chen, Shanghai (CN)

(73) Assignee: Nicoya Therapeutics (Shanghai) Co., Ltd, Shanghai (CN)

( * ) Notice: Subject to any disclaimer, the term of this patent is extended or adjusted under 35 U.S.C. 154(b) by 466 days.

(21) Appl. No.: 17/998,355

(22) PCT Filed: May 19, 2021

(86) PCT No.: PCT/CN2021/094677
§ 371 (c)(1),
(2) Date: Nov. 9, 2022

(87) PCT Pub. No.: WO2021/233349
PCT Pub. Date: Nov. 25, 2021

(65) Prior Publication Data
US 2023/0183221 A1 Jun. 15, 2023

(30) Foreign Application Priority Data
May 22, 2020 (CN) ........................ 202010444113.6

(51) Int. Cl.
*C07D 405/14* (2006.01)

(52) U.S. Cl.
CPC .................................. *C07D 405/14* (2013.01)

(58) Field of Classification Search
CPC .................................................... C07D 405/14
See application file for complete search history.

(56) References Cited

U.S. PATENT DOCUMENTS

| | | | |
|---|---|---|---|
| 6,936,602 | B1 | 8/2005 | Shiraishi et al. |
| 2004/0235822 | A1 | 11/2004 | Shiraishi |
| 2020/0223801 | A1 | 7/2020 | Luo et al. |
| 2020/0268768 | A1 | 8/2020 | Lefebvre |
| 2020/0361911 | A1 | 11/2020 | Song et al. |
| 2023/0002360 | A1 | 1/2023 | Luo et al. |

FOREIGN PATENT DOCUMENTS

| | | | |
|---|---|---|---|
| CN | 108289881 | A | 7/2018 |
| CN | 110023286 | A | 7/2019 |
| JP | 2001058992 | A | 3/2001 |
| JP | 2003119191 | A | 4/2003 |
| RU | 2420284 | C2 | 6/2011 |
| RU | 2018113437 | A | 10/2019 |
| WO | 03014105 | A1 | 2/2003 |
| WO | 2018045043 | A1 | 3/2018 |
| WO | 2019149089 | A1 | 8/2019 |

OTHER PUBLICATIONS

Aug. 13, 2021 International Search Report issued in International Patent Application No. PCT/CN2021/094677.
Aug. 13, 2021 Written Opinion of the International Searching Authority issued in International Patent Application No. PCT/CN2021/094677.
Apr. 4, 2024 Canadian Office Action issued in Canadian Patent Application No. 3,179,593.
Apr. 2, 2024 European Search Report issued in European Patent Application No. 21808699.9.
First office action dated Apr. 23, 2025 issued in the Indonesian application No. P00202215125.
First office action dated May 23, 2023 issued in the Russian application No. 2022133713.
First office action dated May 16, 2023 issued in the Australia application No. 2021276287.
V. G. Belikov "Medpharmaceutical chemistry". Chapter 2.6 "Relationship between chemical structure, properties of substances and their effect on the body".—M.: MEDpress-inform, 2007, pp. 26-28.
(Continued)

*Primary Examiner* — Laura L Stockton
(74) *Attorney, Agent, or Firm* — Houston Beshining Law Office PLLC; Liangang Ye

(57) ABSTRACT

Disclosed are a series of compounds having pyridine structures or pharmaceutically acceptable salts thereof, and an application thereof in the preparation of drugs for the treatment of related diseases. Specifically, disclosed is a compound represented by formula (I) or a pharmaceutically acceptable salt thereof.

(I)

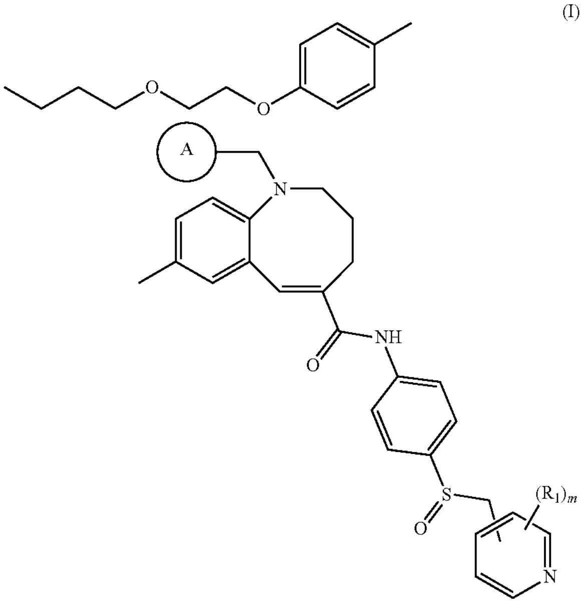

8 Claims, No Drawings

(56) References Cited

OTHER PUBLICATIONS

Richard J. Bastin et al.: "Salt selection and Optimization procedures for Pharmaceutical New Chemical Entities" Organic Process Research & Development, 2000, vol. 4, pp. 427-435.
Search Report dated Sep. 6, 2023 issued in Chinese application No. 2021800364330.
First office action dated Sep. 6, 2023 issued in Chinese application No. 2021800364330.
First office action dated Dec. 12, 2023 issued in Japanese application No. 2022-567108.
First office action dated Dec. 19, 2024 issued in the Korean application No. 10-2022-7044558.

PYRIDINE DERIVATIVE AND APPLICATION THEREOF

The present application is a National Stage of International Application No. PCT/CN2021/094677, filed on May 19, 2021, which claims the priority of Chinese patent application CN202010444113.6 filed on May 22, 2020. The content of the above-mentioned Chinese patent is incorporated herein by reference.

TECHNICAL FIELD

The present disclosure relates to a series of compounds with a pyridine structure, isomers thereof or pharmaceutically acceptable salts thereof, and a use thereof in the manufacture of a medicament for the treatment of related diseases, in particular to compounds represented by formula (I) or pharmaceutically acceptable salts thereof.

BACKGROUND

Chemical inducer cytokines (i.e., chemokines) are relatively small proteins (8-10 kD) that stimulate the migration of cells. The chemokine family is divided into four subfamilies based on the number of amino acid residues between the first and second highly conserved cysteines. Monocyte chemotactic protein-1 (MCP-1) is a member of the CC chemokine subfamily (wherein CC represents a subfamily with adjacent first and second cysteines) and binds cell surface chemokine receptor 2 (CCR2). MCP-1 is an effective chemokine that, upon binding to CCR2, mediates the migration of monocytes and lymphocytes to sites of inflammation (i.e., chemotaxis). MCP-1 is also expressed by cardiomyocytes, vascular endothelial cells, fibroblasts, chondrocytes, smooth muscle cells, mesangial cells, alveolar cells, T lymphocytes, esophageal cancer, etc. After monocytes enter inflammatory tissues, they differentiate into CCR5-expressing macrophages, providing a secondary source of several pro-inflammatory regulators, including tumor necrosis factor-a (TNF-α), interleukin-1 (IL-1), IL-8 CXC chemokine subfamily (wherein CXC represents an amino acid residue between the first and second cysteines), IL-12, arachidonic acid metabolites (such as PGE 2 and LTB 4), oxygen-derived free radicals, matrix metalloproteinases and complement components.

The complementary cellular distribution and differential cellular functions of CCR2 and CCR5 provide the theoretical basis that dual targeting of the two receptors may have greater efficacy than targeting the receptors alone. In monocyte/macrophage biology, CCR2 plays an important role in mediating the migration of monocytes from bone marrow to blood and from blood to tissue, where CCR5 mainly regulates the activation of macrophages in inflammatory tissues, survival and possible retention. Furthermore, CCR5 blockade could improve the therapeutic potential of dual antagonists by suppressing T cell responses in addition to the effects on monocytes/macrophages. CCR2/5 dual antagonists have good potential for druggability.

WO2003014105A1 reported the compound Cenicriviroc (CVC), reference A, the structure of which is shown below.

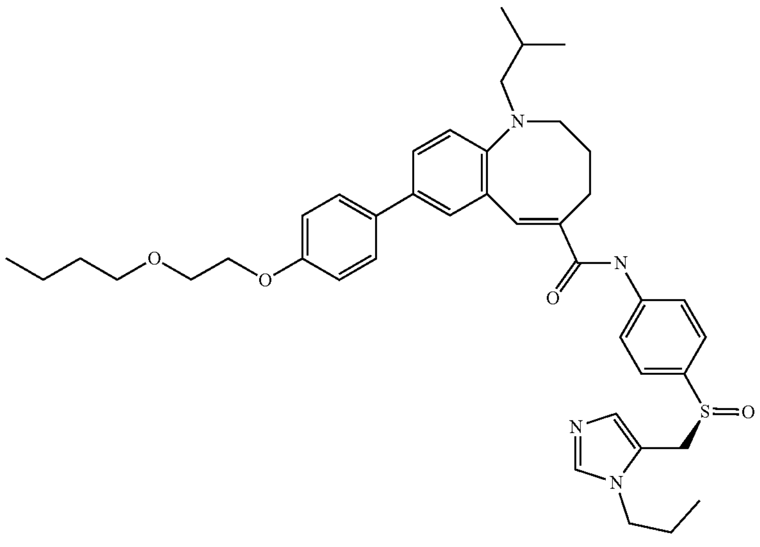

Cenicriviroc

-continued

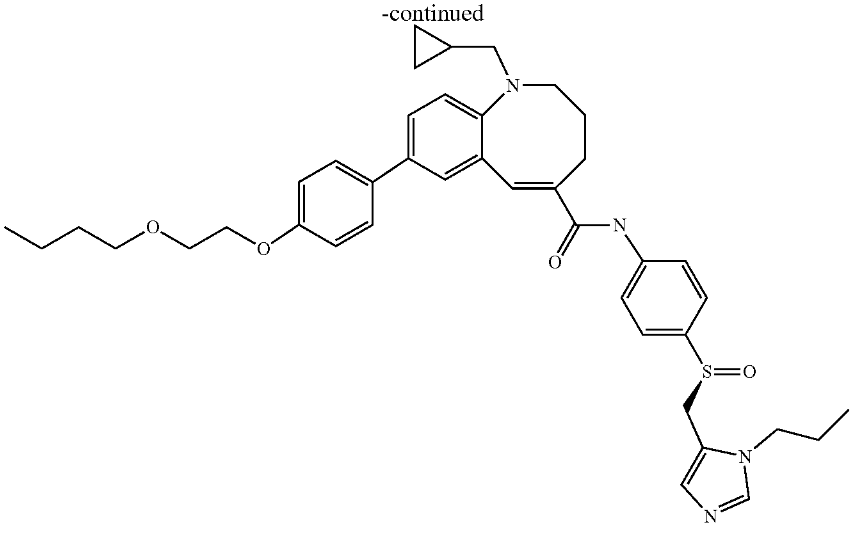

Reference A

CONTENT OF THE PRESENT INVENTION

The present disclosure provides a compound represented by formula (I) or a pharmaceutically acceptable salt thereof,

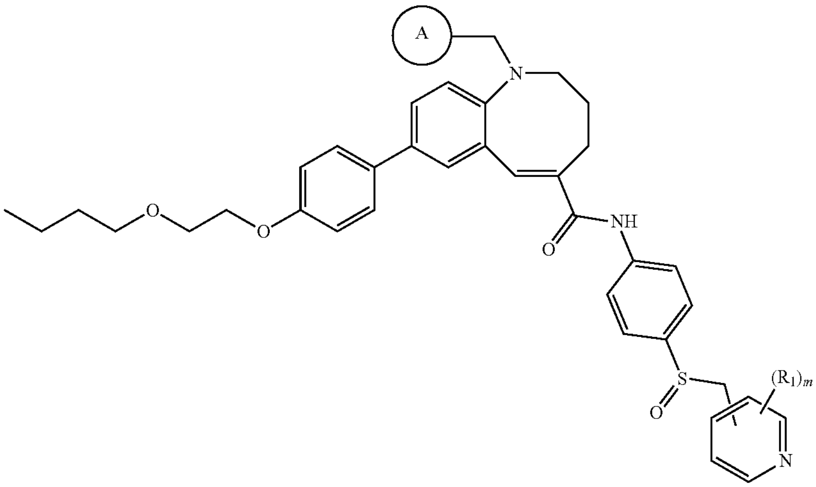

(I)

wherein, each of $R_1$ is independently selected from halogen, OH, $NH_2$, CN, $C_{1-3}$ alkyl and $C_{1-3}$ alkoxy, and the $C_{1-3}$ alkyl and $C_{1-3}$ alkoxy are optionally substituted by 1, 2 or 3 F;

m is selected from 0, 1 and 2;

ring A is selected from 5- to 6-membered heterocycloalkyl;

the heterocycloalkyl contains 1, 2 or 3 heteroatoms or heteroatom groups independently selected from —O—, —NH—, —S— and N.

In some embodiments of the present disclosure, each of the $R_1$ is independently selected from halogen, OH, $NH_2$, CN, $C_{1-3}$ alkyl and $C_{1-3}$ alkoxy, and other variables are as defined in the present disclosure.

In some embodiments of the present disclosure, each of the $R_1$ is independently selected from methyl, ethyl and n-propyl, and other variables are as defined in the present disclosure.

In some embodiments of the present disclosure, the ring A is selected from

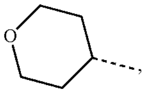

, 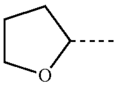

and 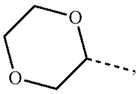

, and, and other variables are as defined in the present disclosure.

In some embodiments of the present disclosure, the structural moiety is

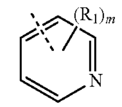

selected from and

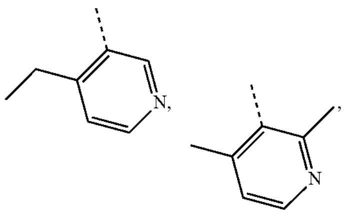

-continued

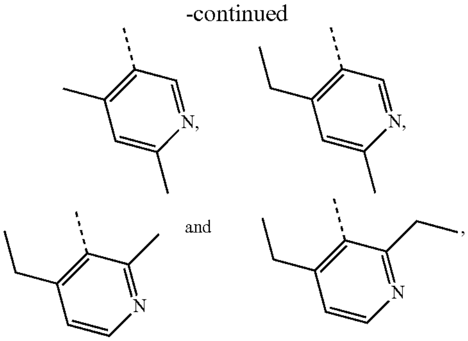

and other variables are as defined in the present disclosure.

There are also some embodiments of the present disclosure that come from any combination of the above-mentioned variables.

The present disclosure also provides a compound represented by the following formula or a pharmaceutically acceptable salt thereof:

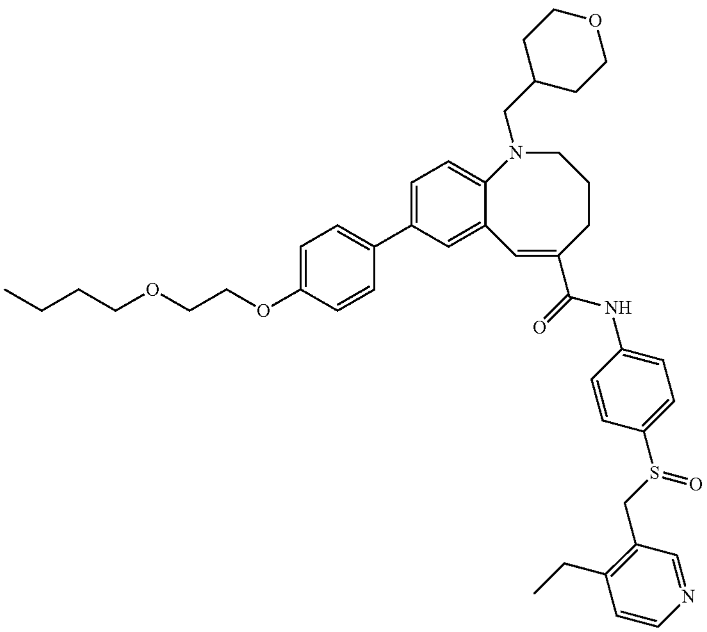

-continued
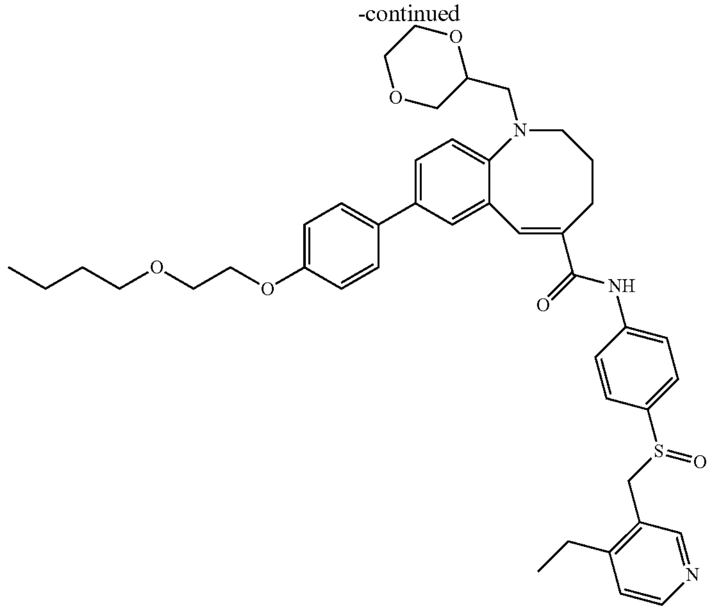
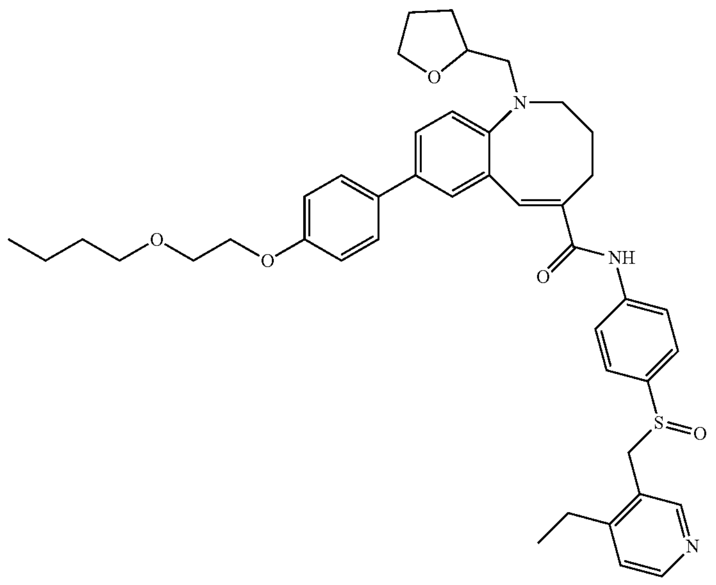

-continued
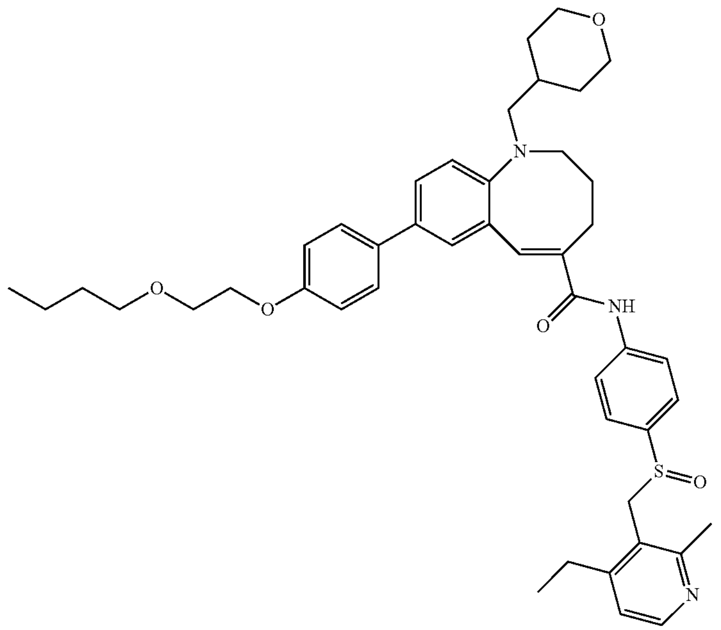
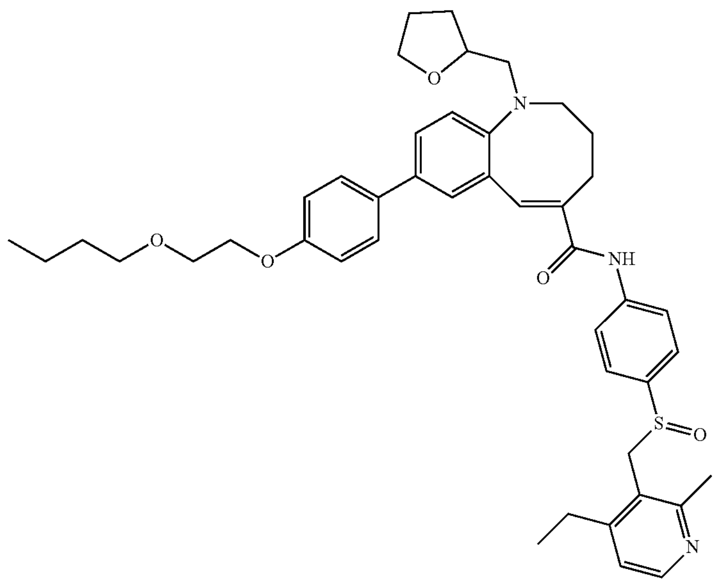

-continued
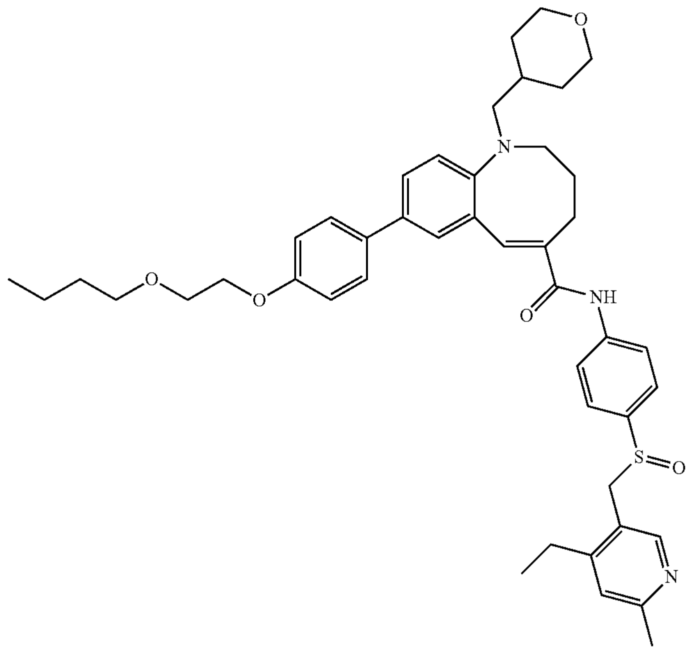
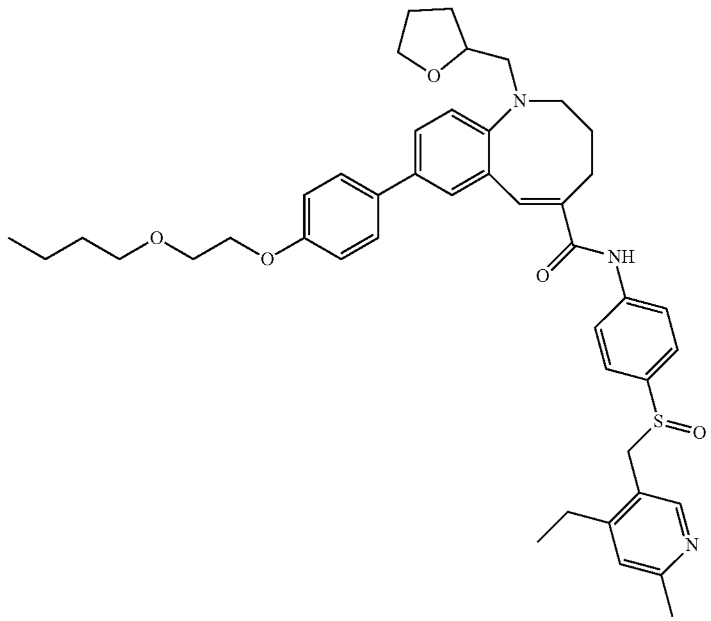

-continued
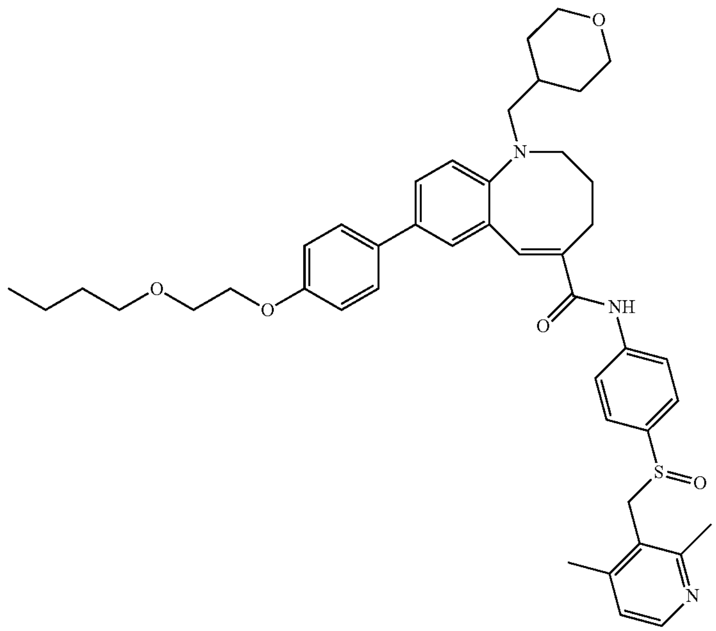
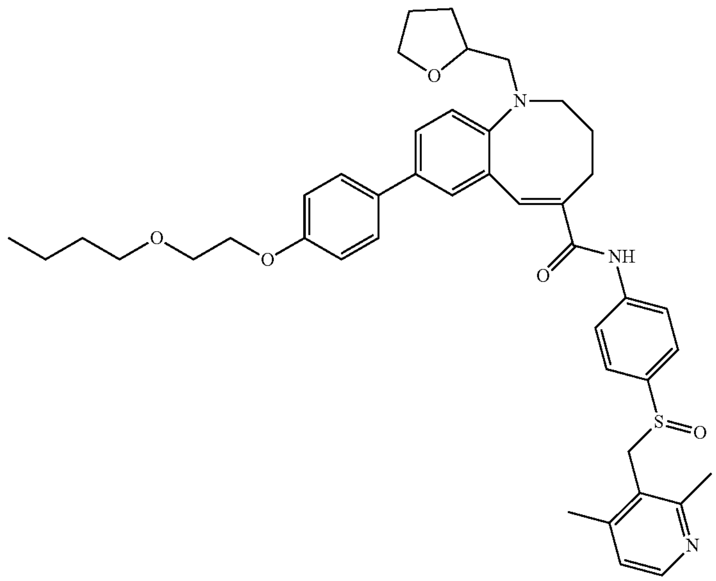

-continued
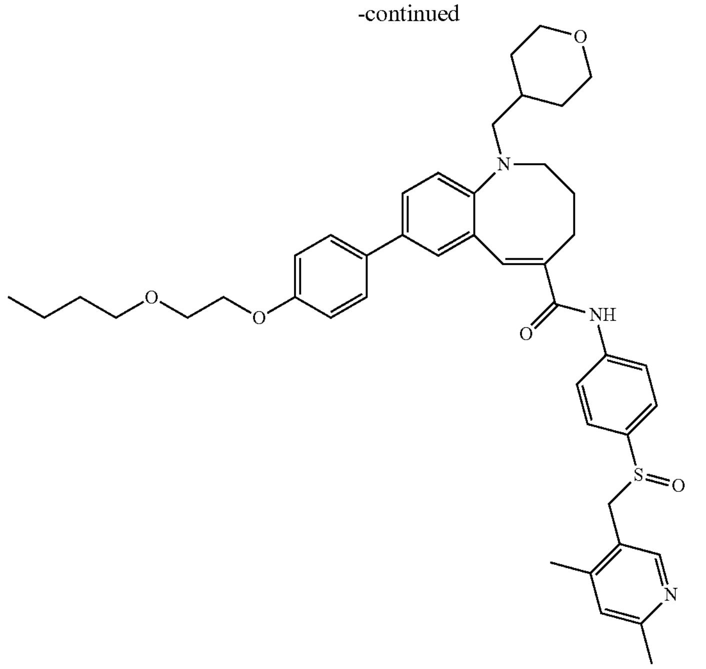
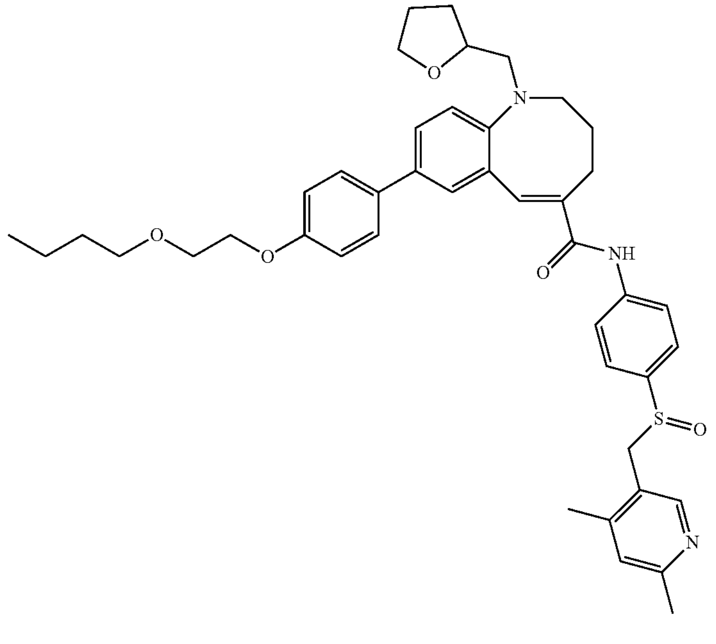

-continued
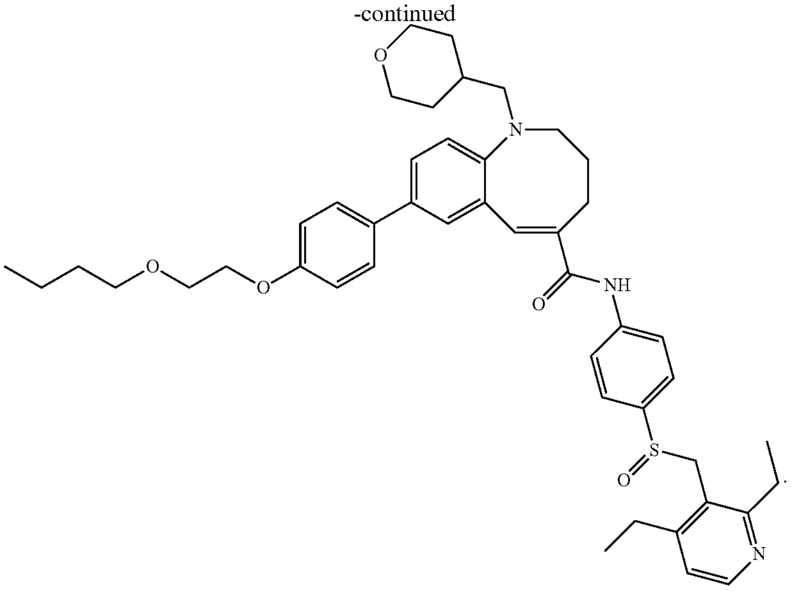
In some embodiments of the present disclosure, the compound or the pharmaceutically acceptable salt thereof is selected from
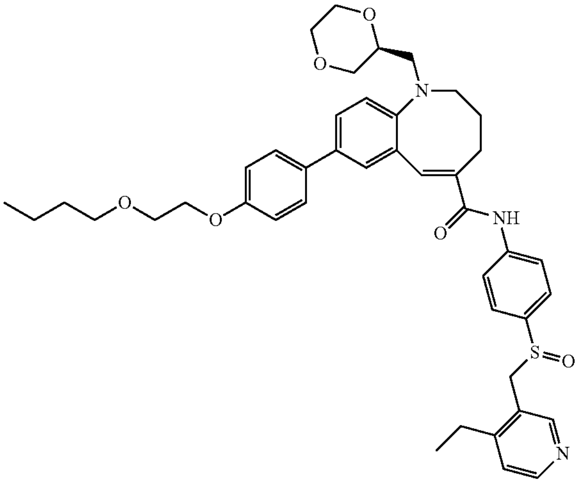
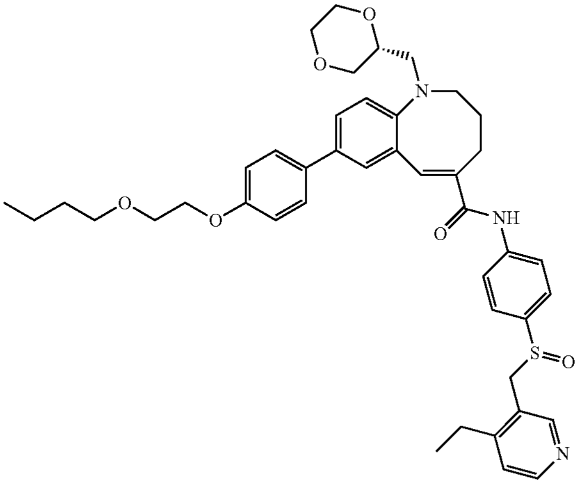
-continued
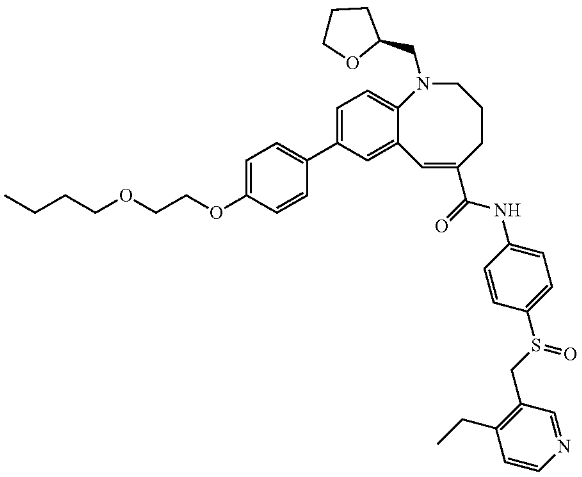
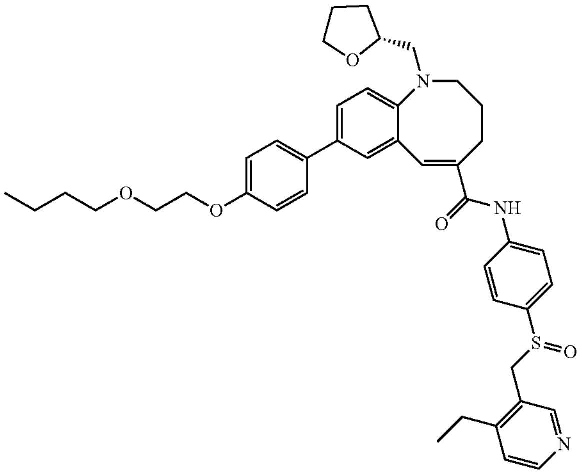

-continued
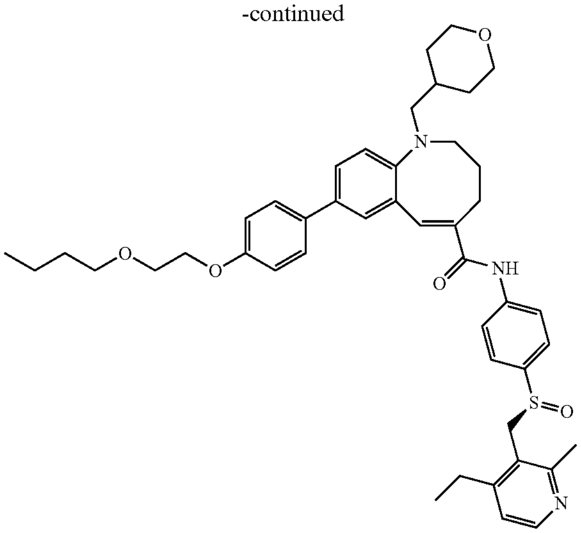
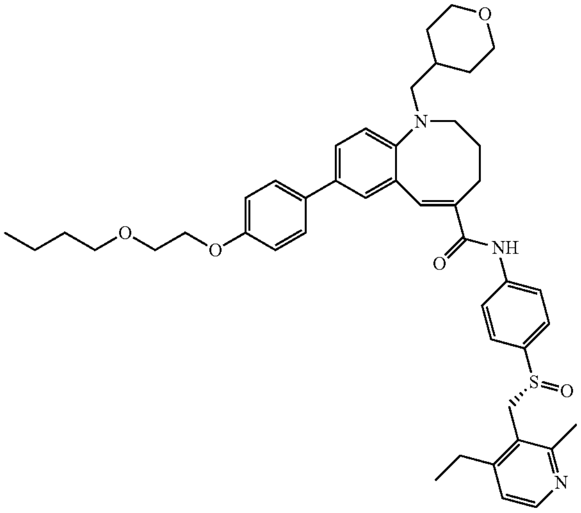
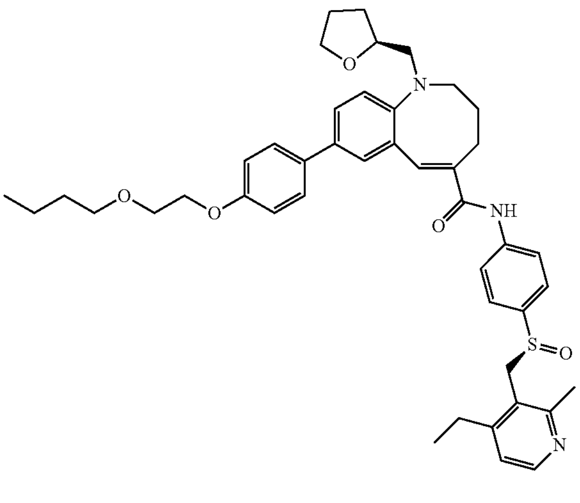
-continued
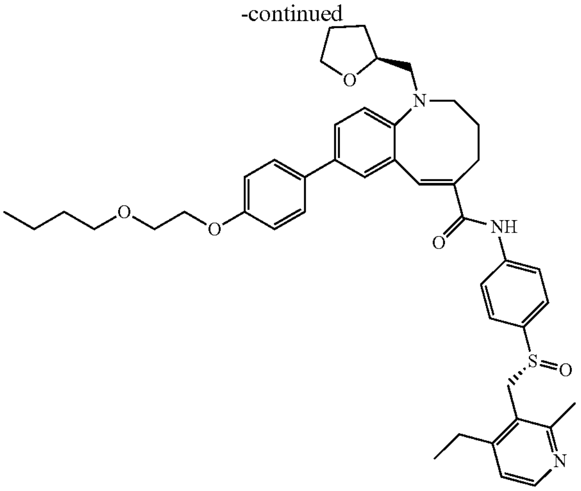
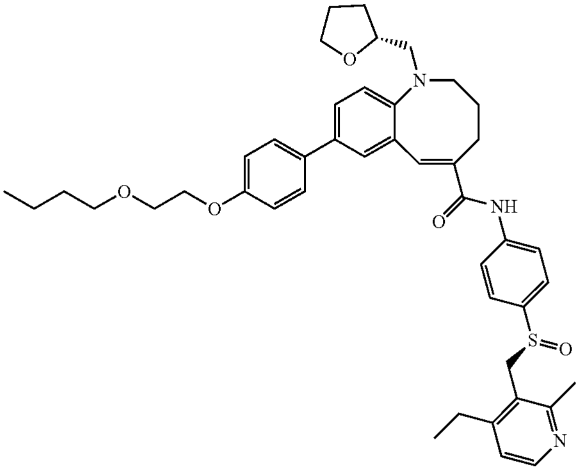
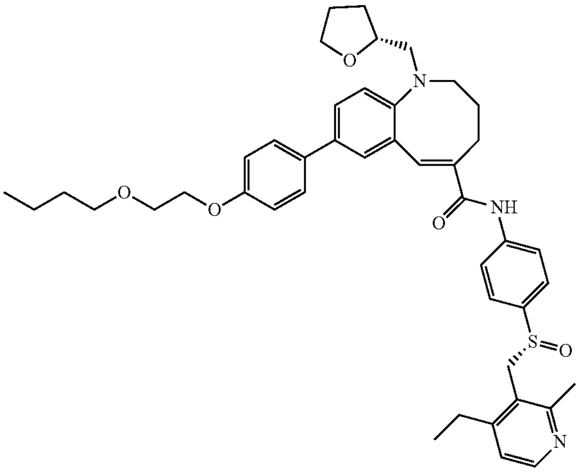

-continued
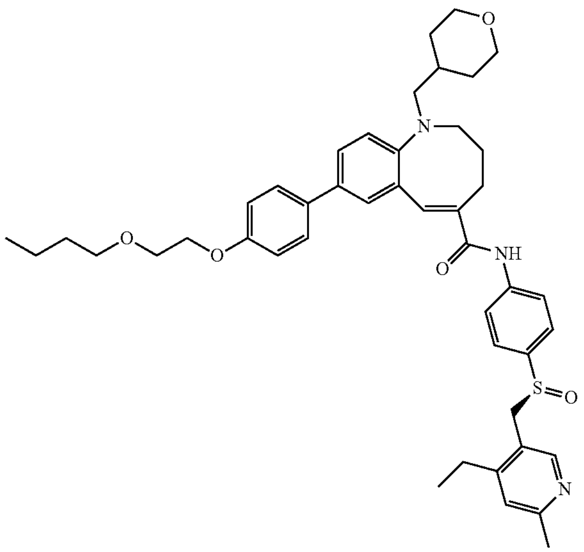
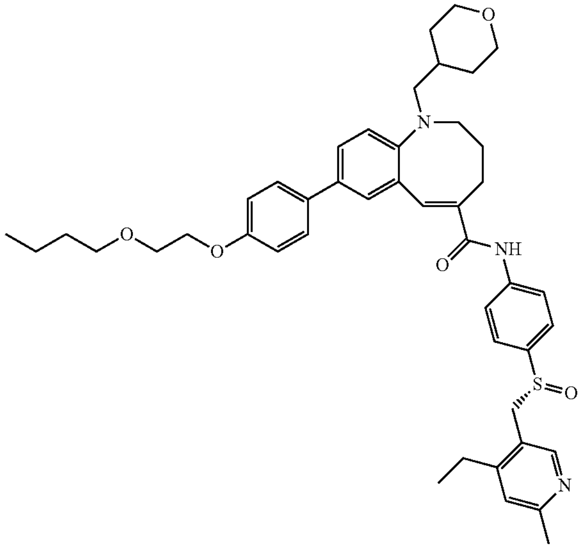
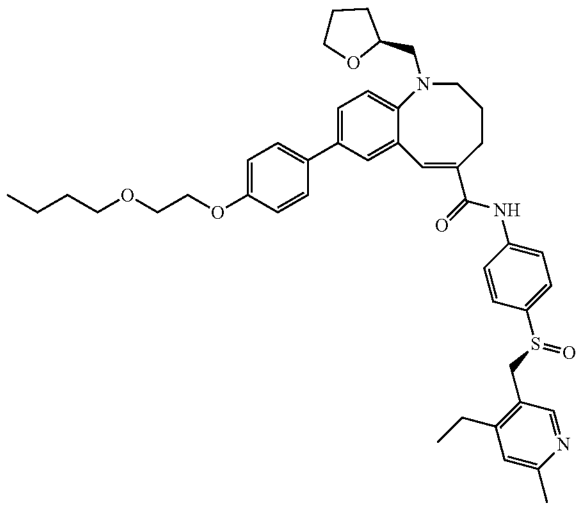
-continued
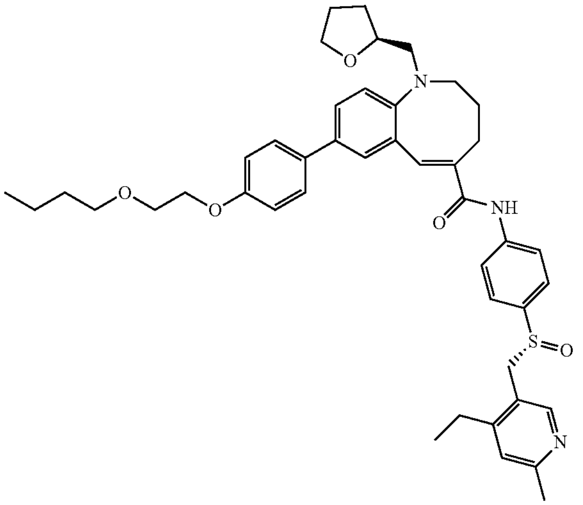
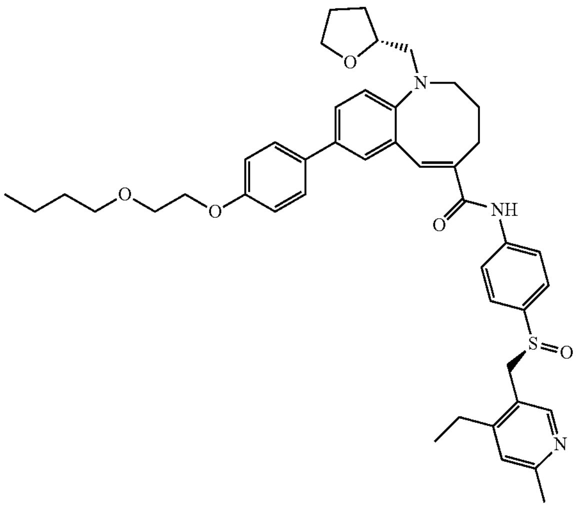
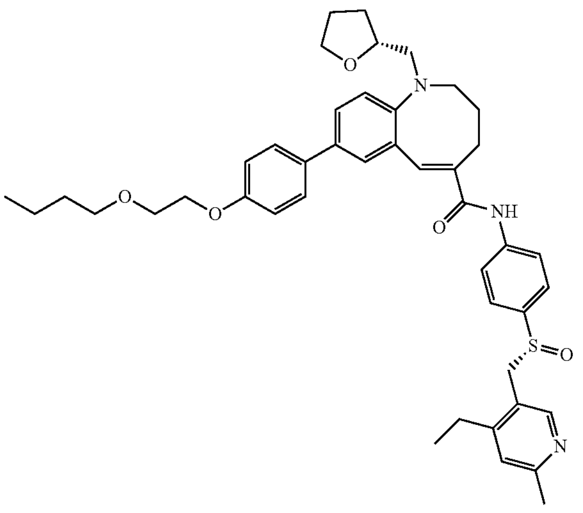

-continued
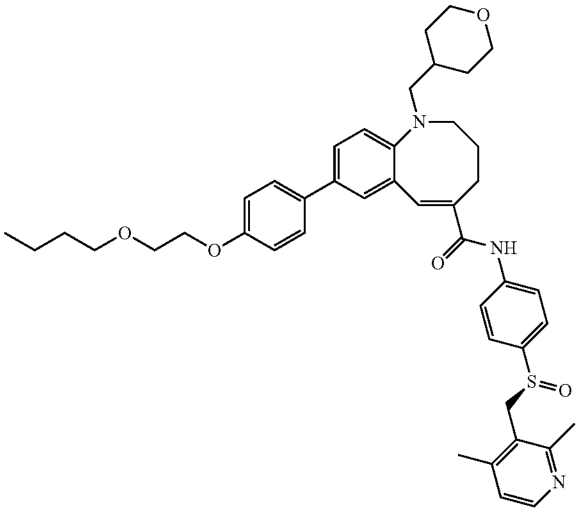
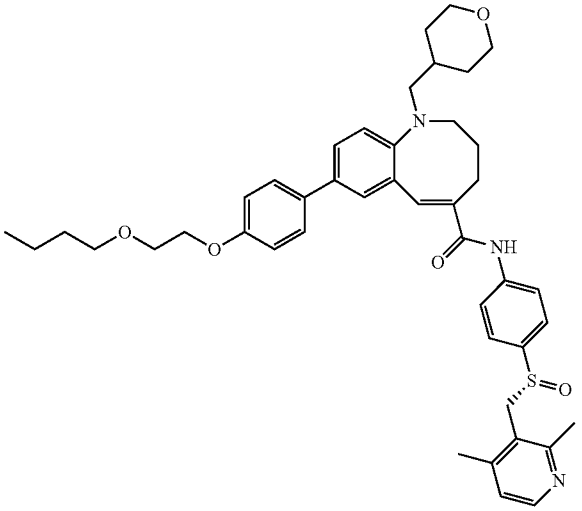
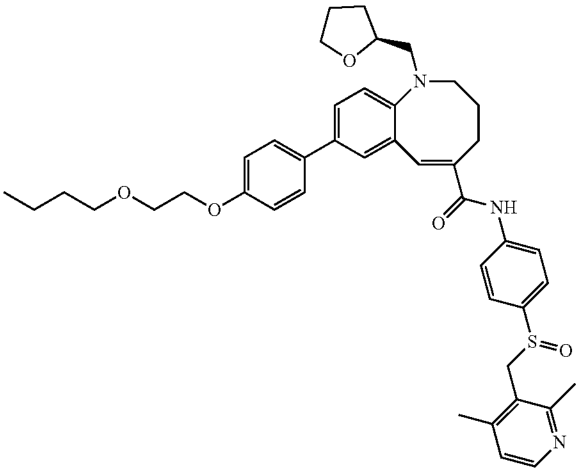
-continued
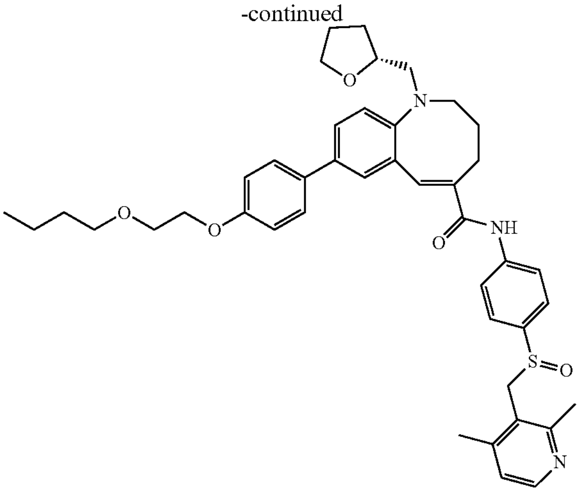
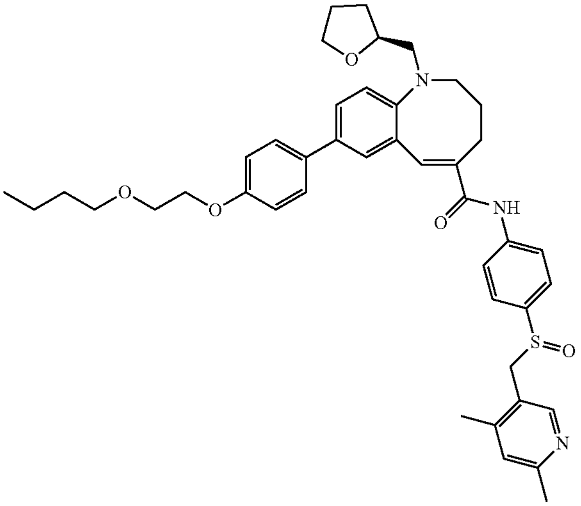
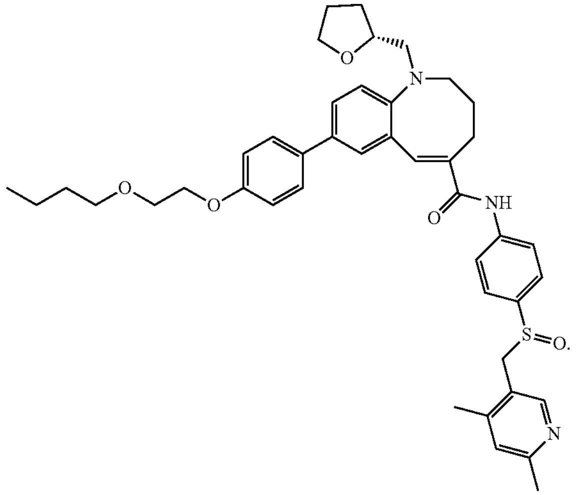
The present disclosure also provides use of the compound or the pharmaceutically acceptable salt thereof in the manufacture of a medicament for treating diseases related to a CCR2/CCR5 dual receptor antagonist.
Technical Effect
The antagonism of the compound of the present disclosure to CCR2 and CCR5 receptors is remarkable. The compound of the present disclosure has no risk of inhibiting the activity of human liver microsomal cytochrome P450 isoenzymes (CYP1A2, CYP2B6, CYP2C8, CYP2C9, CYP2C19, CYP2D6 and CYP3A4), while the reference compound has a strong inhibitory effect on CYP3A4.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ), a wave line ( ) is used to represent a wedged solid bond ( ) or a wedged dashed bond ( ), or the wave line ( ) is used to represent a straight solid bond ( ) and a straight dashed bond ( ).

Unless otherwise specified, when there is a double bond structure in the compound, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ), this refers to the (Z) isomer, (E) isomer or a mixture of two isomers of the compound. For example, the following formula (A) means that the compound exists in the form of a single isomer of formula (A-1) or formula (A-2) or in the form of a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists in the form of a single isomer of formula (C-1) or formula (C-2) or in the form of a mixture of two isomers of formula (C-1) and formula (C-2).

(A)

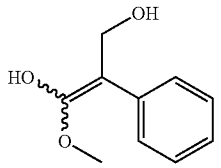

(A-1)

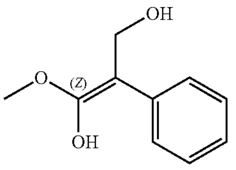

-continued (A-2)

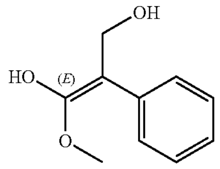

(B)

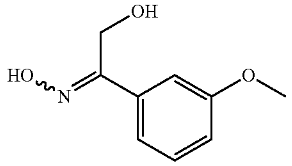

(B-1)

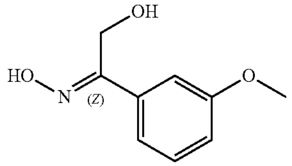

(B-2)

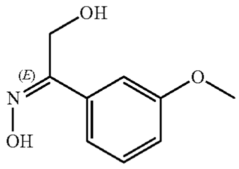

(C)

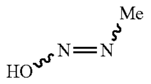

(C-1)

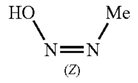

(C-2)

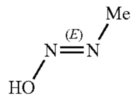

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally separated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, the substituent includes deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

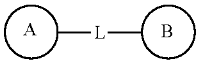

is -M-W—, then -M-W— can link ring A and ring B to form

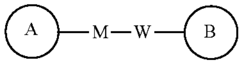

in the direction same as left-to-right reading order, and form

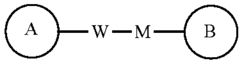

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (), a straight dashed bond () or a wavy line

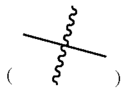

For example, the straight solid bond in $-OCH_3$ means that it is linked to other groups through the oxygen atom in the group; the straight dashed bonds in

means that it is linked to other groups through the two ends of nitrogen atom in the group; the wave lines in

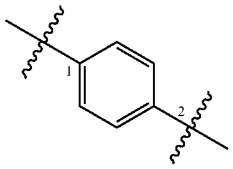 [SMILES: *c1ccc(*)cc1]

means that the phenyl group is linked to other groups through carbon atoms at position 1 and position 2;

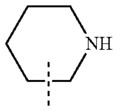

means that it can be linked to other groups through any linkable sites on the piperidinyl by one chemical bond, including at least four types of linkage, including

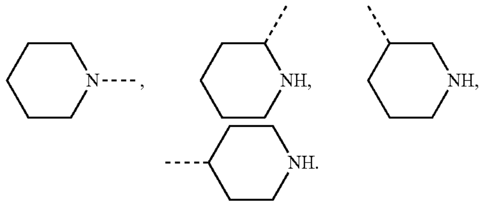

Even though the H atom is drawn on the —N—,

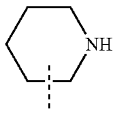

still includes the linkage of

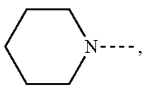

merely when one chemical bond is connected, the H of this site will be reduced by one to the corresponding monovalent piperidinyl.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include, but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, "5- to 6-membered ring" means cycloalkyl, heterocycloalkyl, cycloalkenyl, heterocycloalkenyl, cycloalkynyl, heterocycloalkynyl, aryl or heteroaryl consisting of 5 to 6 ring atoms. The ring includes a single ring, and also includes a bicyclic ring system such as a spiro ring, a fused ring and a bridged ring. Unless otherwise specified, the ring optionally contains 1, 2 or 3 heteroatoms independently selected from O, S and N. The 5- to 6-membered ring includes 5-membered ring and 6-membered ring and the like. The term "5- to 6-membered ring" includes, for example, phenyl, pyridyl and piperidinyl; on the other hand, the term "5- to 6-membered heterocycloalkyl" includes piperidinyl and the like, but does not include phenyl. The term "ring" also includes ring systems containing at least one ring, wherein each "ring" independently meets the above-mentioned definition.

Unless otherwise specified, the term "halo" or "halogen" by itself or as part of another substituent refers to fluorine, chlorine, bromine or iodine atom.

The term "protecting group" includes, but is not limited to "amino protecting group", "hydroxy protecting group" or "thiol protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvent used in the present disclosure is commercially available. The present disclosure adopts the following abbreviations: aq stands for water; EDC stands for N-(3-dimethylaminopropyl)-N'-ethylcarbodiimide hydrochloride; eq stands for equivalent; DMF stands for N,N-dimethylformamide; DCM stands for dichloromethane; DMSO stands for dimethyl sulfoxide; EtOH stands for ethanol; MeOH stands for methanol; $Boc_2O$ for di-tert butyl dicarbonate; TFA stands for trifluoroacetic acid; DMP stands for Dess-Martin periodinane.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

The present disclosure is described in detail by the embodiments below, but it does not mean that there is any adverse restriction on the present disclosure. The present disclosure has been described in detail herein, wherein specific embodiments thereof are also disclosed.

It will be apparent to those skilled in the art that various variations and improvements can be made to specific embodiments of the present disclosure without departing from the spirit and scope of the present disclosure.

Reference Embodiment 1

AA-1

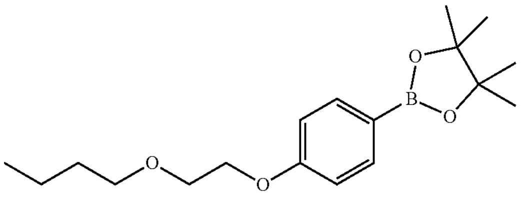

Synthetic Route:

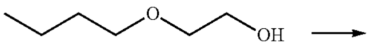

AA-1-1

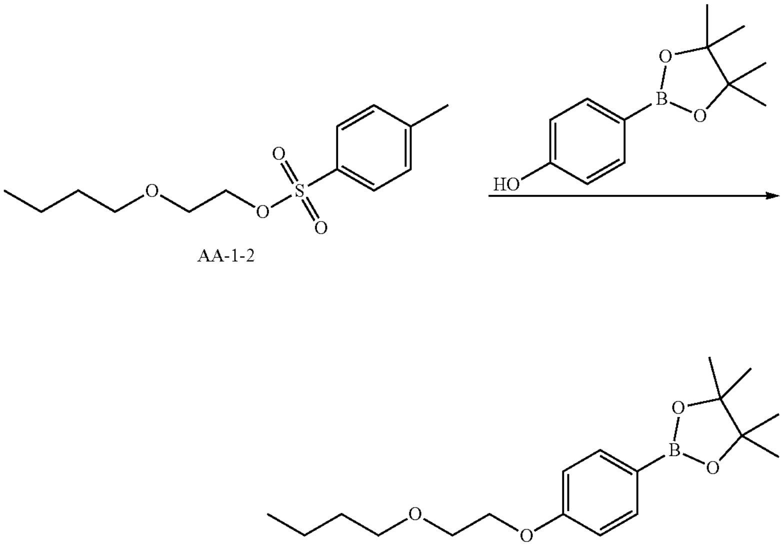

AA-1-2, AA-1

Step 1: Synthesis of Compound AA-1-2

Compound AA-1-1 (100 g), p-toluenesulfonyl chloride (146.67 g), and triethylamine (233.54 g) were dissolved in dichloromethane (0.5 L) and stirred at room temperature for 12 hours. Then the reaction mixture was cooled to room temperature, and the solvent was removed under reduced pressure, and then water (400 mL) was added to dissolve the residue. The aqueous phase was extracted three times with ethyl acetate (1.5 L), and the combined organic phases were washed twice with saturated brine (400 mL), and dried over anhydrous sodium sulfate. After the drying agent was filtered off, the solvent was removed under reduced pressure to obtain compound AA-1-2.

$^1$H NMR (400 MHz, $CDCl_3$) δ ppm 7.73 (d, J=8.00 Hz, 2H), 7.27 (d, J=8.00 Hz, 2H), 4.05-4.10 (m, 2H), 3.50-3.55 (m, 2H), 3.30 (t, J=6.4 Hz, 2H), 2.37 (s, 3H), 1.35-1.44 (m, 2H), 1.16-1.27 (m, 2H), 0.81 (t, J=7.2 Hz, 3H).

Step 2: Synthesis of Compound AA-1.

Compound AA-1-2 (170.10 g), 4-hydroxyphenylboronicacidpinacolester (137.44 g) were dissolved in acetonitrile (1.6 L), and then potassium carbonate (86.32 g) and potassium iodide (10.37 g) were added thereto at room temperature. The obtained solution was stirred for 12 hours at 60° C. under nitrogen protection. After the reaction solution was cooled to room temperature, the solvent was removed under reduced pressure, and water (500 mL) was added to dissolve the residue. The aqueous phase was extracted three times with ethyl acetate (2 L×3), and the solvent was removed under reduced pressure after combination, and compound AA-1 was obtained by column chromatography.

$^1$H NMR (400 MHz, $CDCl_3$) δ ppm 7.78-7.71 (m, 2H), 6.95-6.88 (m, 2H), 4.19-4.12 (m, 2H), 3.83-3.75 (m, 2H), 3.54 (t, J=6.8 Hz, 2H), 1.65-1.57 (m, 2H), 1.44-1.36 (m, 2H), 1.34 (s, 12H), 0.93 (t, J=7.2 Hz, 3H).

Reference Embodiment 2

AA-2

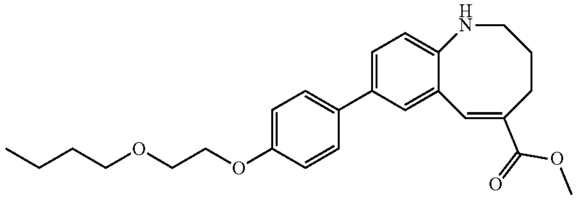

Synthetic Route:

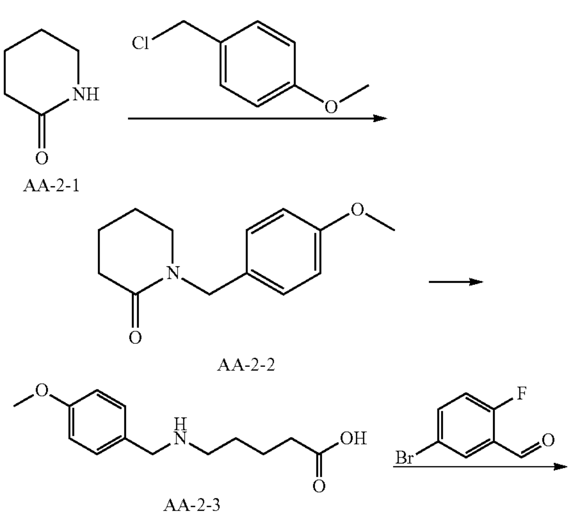

AA-2-1, AA-2-2, AA-2-3

-continued

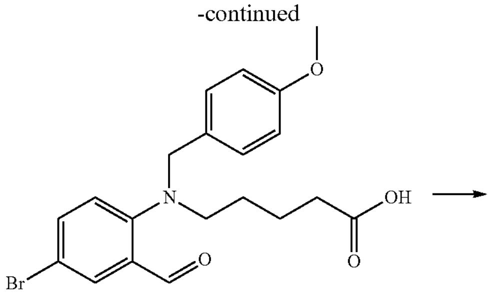

AA-2-4

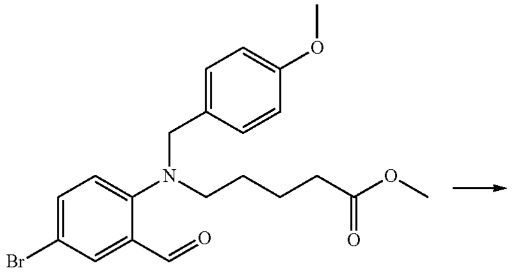

AA-2-5

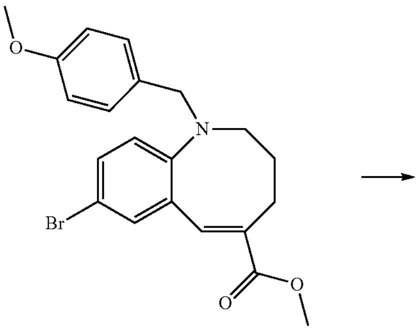

AA-2-6

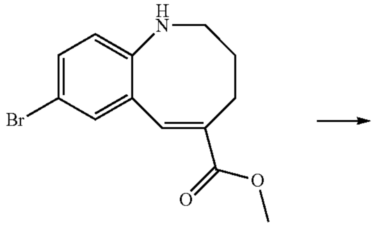

AA-2-7

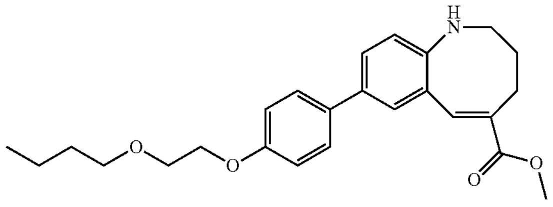

AA-2

Step 1: Synthesis of Compound AA-2-2

Tetrabutylammonium bromide (86.58 g) and potassium hydroxide (339.6 g) were suspended in toluene (5000 mL), and the mixture was refluxed for 16 hours, and then piperidin-2-one (500.00 g) and 4-methoxybenzylchloride (1.03 kg) were added thereto. The mixture was kept at 100° C. and stirred for 24 hours. The reaction solution was cooled to room temperature, washed three times with water (2000 mL×3), and the organic phase was dried over anhydrous sodium sulfate, filtered and concentrated. The concentrated solution was separated by column chromatography to obtain compound AA-2-2.

Step 2: Synthesis of Compound AA-2-4

A solution of compound AA-2-2 (40 g) and sodium hydroxide (7.29 g) in water (200 mL) was stirred at 80° C. for 24 hours. The mixture was neutralized with concentrated hydrochloric acid (7.38 mL) at 0° C. to obtain a mixed solution of compound AA-2-3. Sodium carbonate (65.66 g) and dimethyl sulfoxide (600 mL) were added to the mixture at room temperature. 5-Bromo-2-fluorobenzaldehyde (46.11 g) was then added dropwise to the mixture at 100° C. The reaction mixture was then refluxed at 100° C. for 48 hours. The reaction was adjusted to pH=7 with ammonium chloride aqueous solution (1 mol/L) under ice-bath, and extracted with ethyl acetate (1 L×3). The organic layer was washed with water and brine, dried over anhydrous sodium sulfate and concentrated. The residue was purified by column chromatography (petroleum ether/ethyl acetate=200:1 to 1:1). Compound AA-2-4 was obtained.

Step 3: Synthesis of Compound AA-2-5

A solution of iodomethane (22 g) in acetonitrile (50 mL) was added to a mixture of compound AA-2-4 (10 g) and sodium carbonate (12.61 g) in acetonitrile (100 mL). The reaction mixture was stirred at 15 to 30° C. for 24 hours under nitrogen protection. The reaction mixture was quenched with water (300 mL) and extracted with ethyl acetate (400 mL×2). The organic layer was washed with brine, dried over anhydrous sodium sulfate, and concentrated.

The crude product was purified by silica gel column chromatography (petroleum ether/ethyl acetate=50:1 to 20:1 to 10:1) to obtain compound AA-2-5.

$^1$H NMR (400 MHz, $CDCl_3$) δ ppm 10.31 (s, 1H), 7.89 (d, J=2.4 Hz, 1H), 7.54 (dd, J=9.2, 2.4 Hz, 1H), 7.04 (d, J=8.4 Hz, 2H), 6.97 (d, J=9.02 Hz, 1H), 6.80 (d, J=8.4 Hz, 2H), 4.21 (s, 2H), 3.77 (s, 3H), 3.63 (s, 3H), 3.07 (t, J=6.8 Hz, 2H), 2.25 (t, J=6.8 Hz, 2H), 1.46-1.58 (m, 4H).

Step 4: Synthesis of Compound AA-2-6

Sodium methoxide (6.84 g) was added to a solution of compound AA-2-5 (11 g) in dimethyl carbonate (42.8 g). Then the reaction mixture was heated to 60° C. and stirred at 60° C. for 35 hours. The pH (7-8) was adjusted with ammonium chloride (1 mol/L) aqueous solution, and the reaction mixture was filtered. The filter cake was concentrated under reduced pressure to obtain compound AA-2-6.

$^1$H NMR (400 MHz, $CDCl_3$) δ ppm 7.74 (s, 1H), 7.26 (s, 1H), 7.05-7.11 (m, 3H), 6.88 (d, J=8.4 Hz, 2H), 6.53 (d, J=9.2 Hz, 1H), 4.39 (s, 2H), 3.80 (d, J=2.0 Hz, 6H), 3.48 (t, J=5.2 Hz, 2H), 2.58 (t, J=6.0 Hz, 2H), 1.47 (d, J=5.6 Hz, 2H).

Step 5: Synthesis of Compound AA-2-7

Trifluoroacetic acid (100 mL) was added to a solution of compound AA-2-6 (10 g) in toluene (50 mL). The reaction mixture was heated to 60° C. and stirred at 60° C. for 8 hours. The reaction mixture was neutralized to pH=7 with saturated sodium bicarbonate under ice-bath, and the mixture was extracted with ethyl acetate (250 mL×2). The organic layer was washed with brine, dried over anhydrous sodium sulfate, and concentrated. The residue was purified by silica gel column (petroleum ether/ethyl acetate=50:1 to 5:1) to obtain compound AA-2-7.

$^1$H NMR (400 MHz, $CDCl_3$) δ ppm 7.66 (s, 1H), 7.39-7.05 (m, 1H), 6.85 (d, J=8.8 Hz, 1H), 6.36 (d, J=8.8 Hz, 1H), 3.81 (s, 3H), 3.51 (t, J=5.2 Hz, 2H), 2.75 (d, J=6.8 Hz, 2H), 1.49-1.40 (m, 2H).

Step 6: Synthesis of Compound AA-2

At 25° C., compounds AA-2-7 (7.5 g, 25.32 mmol, 1 eq) and AA-1 (8.92 g, 27.86 mmol, 1.1 eq) were dissolved in dimethyl sulfoxide (62.5 mL) and water (12.5 mL), and then Pd(dppf)$Cl_2$ (926.50 mg, 1.27 mmol, 0.05 eq) and potassium carbonate (10.50 g, 75.97 mmol, 3 eq) were added thereto, and then the reaction was conducted at 80° C. for 18 hours under nitrogen protection. The solution was first filtered, then 100 mL of water was added to the filtrate, and then extracted three times with ethyl acetate (100 mL×3). The combined organic phases were washed once with saturated brine, then dried over anhydrous sodium sulfate, filtered and then concentrated under reduced pressure to obtain the product as a black oil. The oil was separated by column chromatography (petroleum ether:ethyl acetate=20:1 to 8:1) to obtain compound AA-2. MS-ESI (m/z): 410.0 $[M+1]^+$.

Reference Embodiment 3

AA-3A

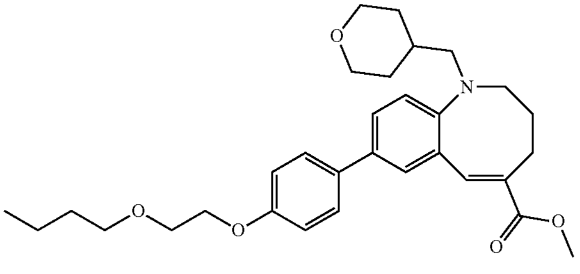

Synthetic Route:

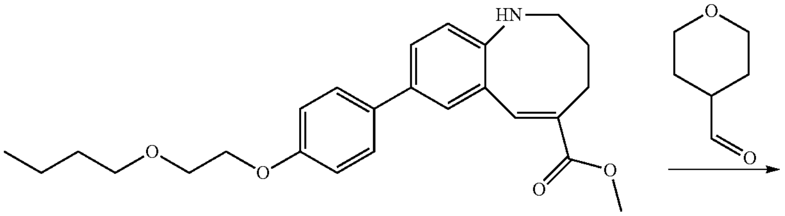

AA-2

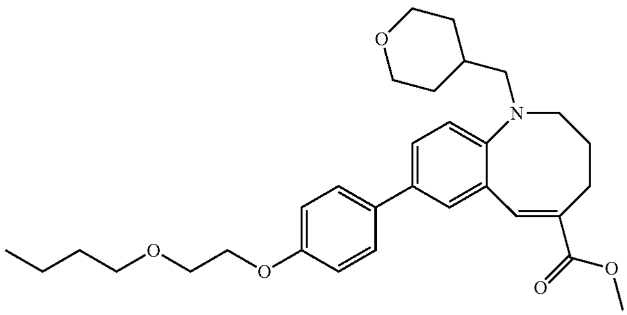

AA-3A

Step 1: Synthesis of Compound AA-3A

Zinc chloride (22.97 g) and sodium triacetoxyborohydride (107 g) were added to a solution of compound AA-2 (69 g) and tetrahydropyran-4-carbaldehyde (38.46 g) in dichloromethane (1500 mL) at 25° C., stirred under nitrogen for 18 hours. 500 mL of water was added to the reaction solution, then the reaction solution was extracted three times with dichloromethane (500 mL×3), and the organic phases were combined and washed once with saturated brine (500 mL), dried over anhydrous sodium sulfate, filtered, and concentrated under reduced pressure, then separated by silica gel column chromatography (petroleum ether:ethyl acetate=20:1 to 9:1) to obtain compound AA-3A.

Reference Embodiment 4

AA-3B-A or AA-3B-B

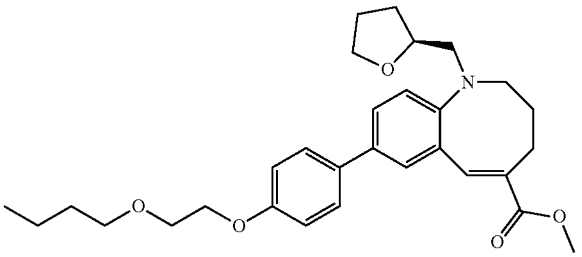

-continued

AA-3B-B or AA-3B-A

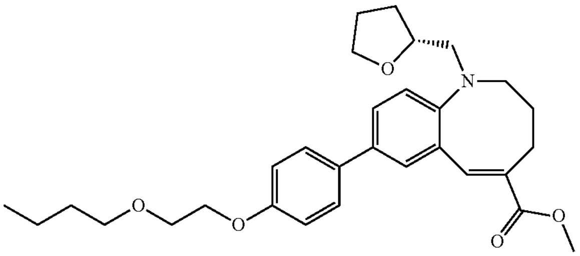

Synthetic Route:

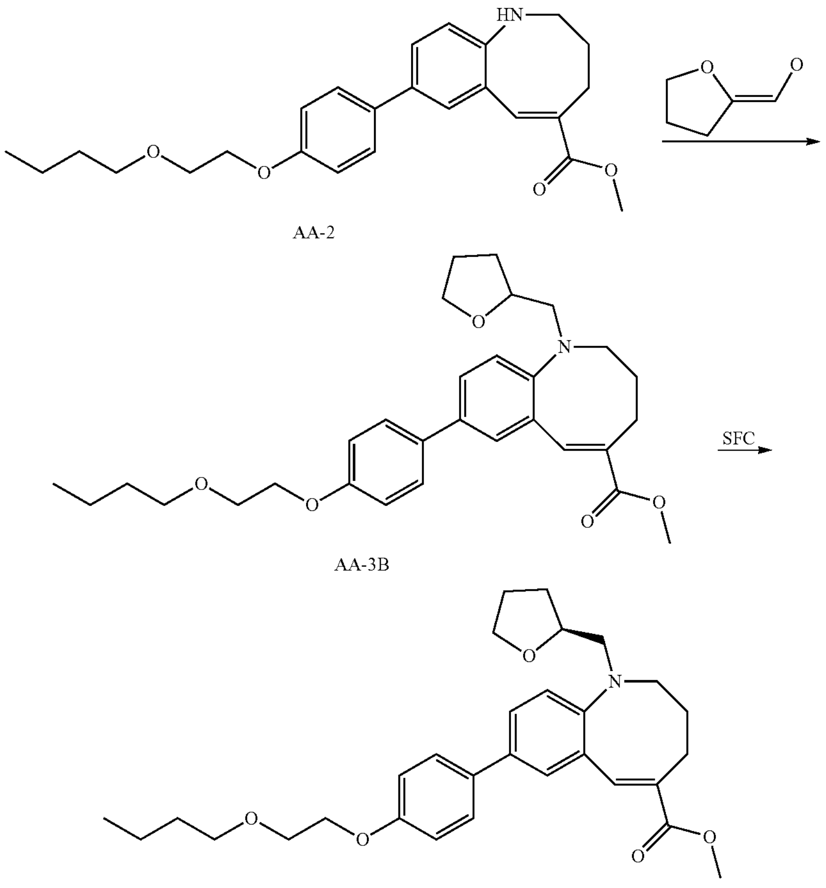

AA-2

AA-3B

AA-3B-A or AA-3B-B

-continued

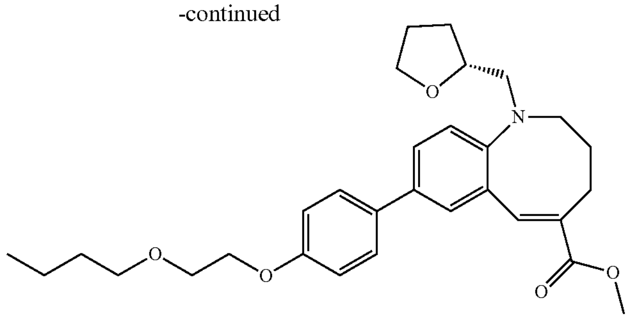

AA-3B-B or AA-3B-A

Step 1: Synthesis of Compound AA-3B

Compound AA-2 (327.24 mg) and tetrahydrofuran-2-carbaldehyde (0.1 g) were dissolved in dichloromethane (5 mL) at room temperature, stirred for 10 minutes, then sodium triacetoxyborohydride (635.09 mg) was added thereto, then the reaction was conducted under nitrogen protection at 25° C. for 14 hours. 5 mL of water was added to the solution, then the mixture was extracted three times with dichloromethane (10 mL×3), and the combined organic phases were washed once with saturated brine, dried over anhydrous sodium sulfate, filtered and concentrated under reduced pressure to obtain a yellow oil. The product was separated by HPLC. (Column type: Boston Green ODS 150*30 mm*5 m; mobile phase: [water (0.075% TFA)-ACN]; ACN %: 80%-100%, 8 min) to obtain compound AA-3B.

Step 2: Synthesis of Compounds AA-3B-A and AA-3B-B

The AA-3B (700 mg) sample was subjected to SFC separation (column type: Cellulose 2 150×4.6 mm I.D., 5 m; mobile phase: A: $CO_2$ B: methanol (0.05% DEA); gradient: 40% B; flow rate: 2.5 mL/min; column temperature: 35° C.; column pressure: 1500 psi. Compounds AA-3B-A (retention time: 5.053 min) and AA-3B-B (retention time: 5.514 min) were obtained.

Reference Embodiment 5

AA-3C-A or AA-3C-B

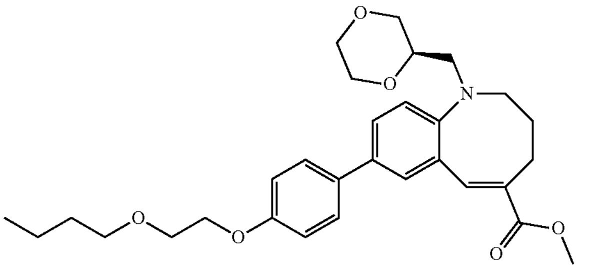

AA-3C-B or AA-3C-A

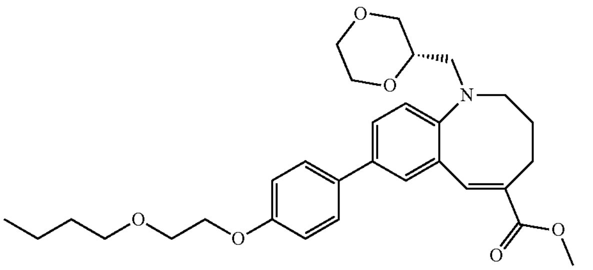

Synthetic Route:

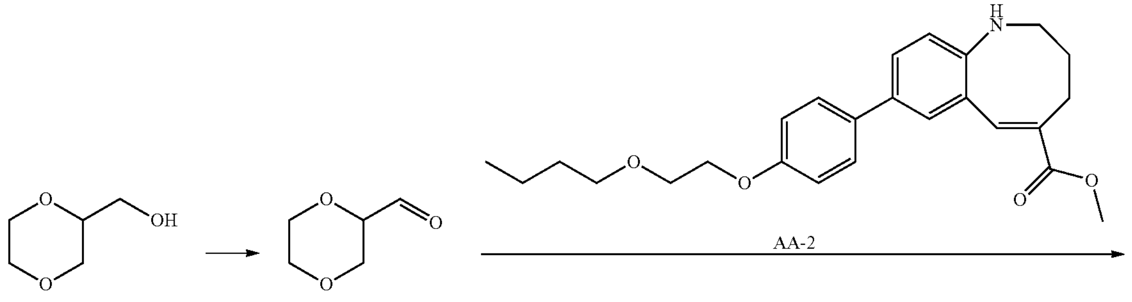

AA-3C-1

AA-3C-2

-continued

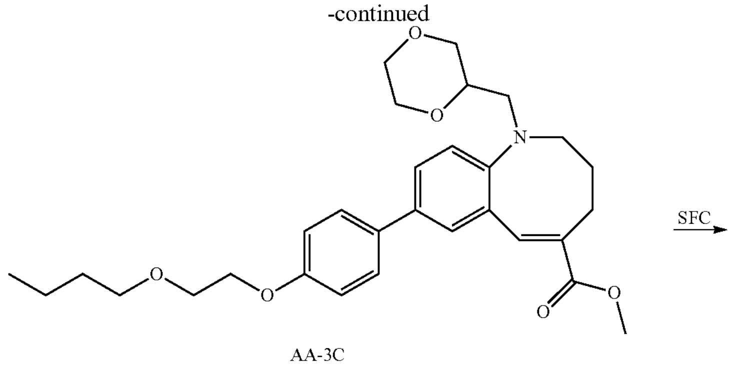

AA-3C

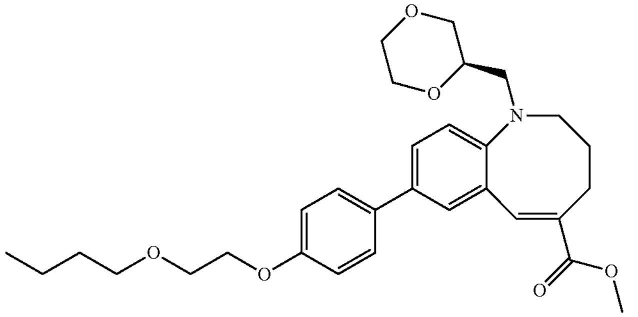

AA-3C-A or AA-3C-B

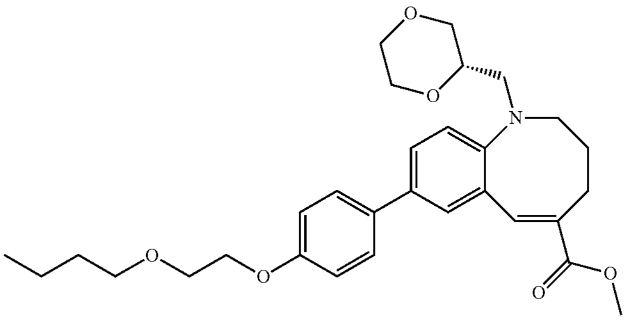

AA-3C-B or AA-3C-A

Step 1: Synthesis of Compound AA-3C-2

DMP (21.54 g) was added to a solution of compound AA-3C-1 (5 g) in dichloromethane (120 mL) at 0° C., and the whole mixture was stirred at 25° C. for 3 hours. The reaction solution was filtered through celite, and the filtrate was directly mixed with silica gel powder. The above-mentioned filtrate mixed with silica gel powder was separated by silica gel column chromatography (petroleum ether: ethyl acetate=10:1 to 5:1) to obtain compound AA-3C-2.

Step 2: Synthesis of Compound AA-3C

A solution of compounds AA-2 (3.17 g) and AA-3C-2 (0.9 g) in dichloromethane (30 mL) was stirred at 25° C. for 0.5 hours, then sodium triacetoxyborohydride (3.29 g) was added to the mixture, then the whole mixture was stirred at 25° C. for 16 hours. The reaction solution was added with water (100 mL), then extracted three times with dichloromethane (50 mL×3). The combined organic phase was washed once with saturated brine (100 mL), dried over anhydrous sodium sulfate, filtered, and concentrated under reduced pressure to obtain a yellow oil. The yellow oil was separated by silica gel column chromatography (petroleum ether:ethyl acetate=10:1 to 1:1) to obtain compound AA-3C.

Step 3: Synthesis of Compounds AA-3C-A and AA-3C-B

Compound AA-3C (0.75 g) was split to obtain compounds AA-3C-A (retention time: 5.053 min) and AA-3C-B (retention time: 5.514 min) through SFC separation. SFC: (column type: Cellulose 2 150×4.6 mm I.D., 5 m mobile phase: A: $CO_2$ B: methanol (0.05% DEA), gradient: 40% B, flow rate: 2.5 mL/min, column temperature: 35° C., pressure: 1500 psi). MS-ESI (m/z): 510.0[M+1]+.

Reference Embodiment 6

BB-1

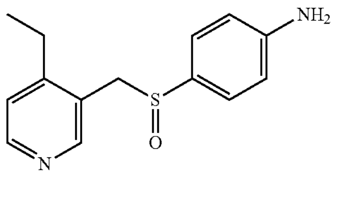

Synthetic Route:

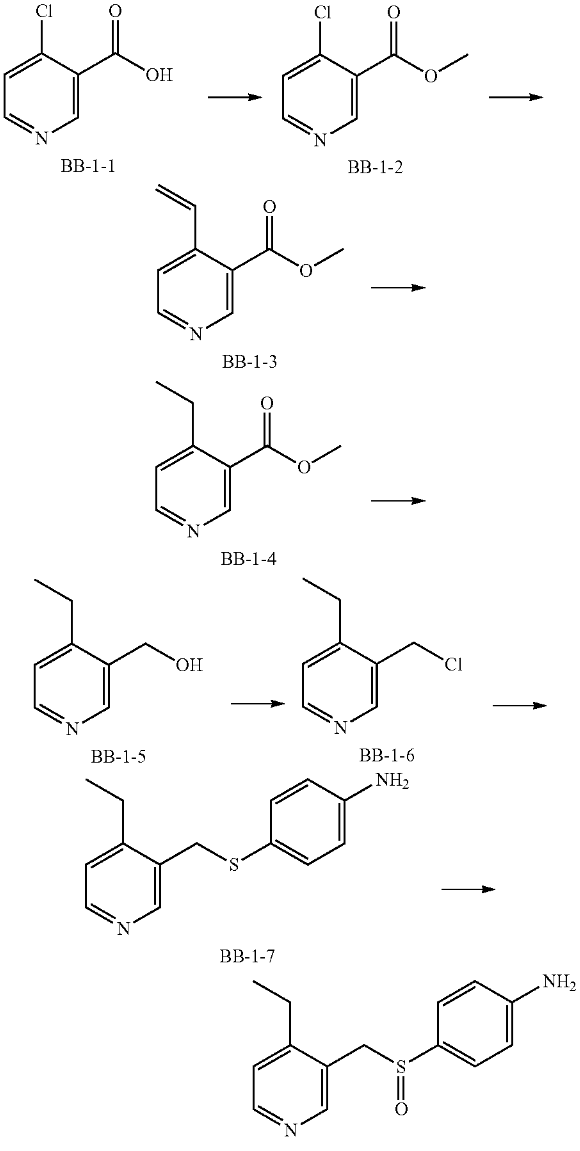

BB-1-1 BB-1-2 BB-1-3 BB-1-4 BB-1-5 BB-1-6 BB-1-7 BB-1

Step 1: Synthesis of Compound BB-1-2

At 25° C., oxalyl chloride (10.07 g) was added dropwise to a solution of compound BB-1-1 (5.0 g) and DMF (1.07 g) in dichloromethane (50.00 mL) and stirred for 3 hours, then methanol (10 mL) was added thereto and stirred for 1 hour, and the reaction solution was concentrated to obtain compound BB-1-2.

$^1H$ NMR (400 MHz, $CDCl_3$) δ ppm 9.32 (s, 1H), 9.09 (d, J=6.0 Hz, 1H), 8.07 (d, J=6.0 Hz, 1H), 4.05 (s, 3H).

Step 2: Synthesis of Compound BB-1-3

Under nitrogen atmosphere at 100° C., compound BB-1-2 (5.0 g) and potassium vinyltrifluoroborate (3.9 g) were added to a mixed solvent of dioxane (45 mL) and water (15 mL), and then Pd(dppf)$Cl_2$ (213 mg) and potassium carbonate (8.06 g) were added thereto and stirred for 12 hours, then the reaction solution was concentrated to remove dioxane. Water (10 mL) was added to the residue, then the mixture was extracted with dichloromethane (20 mL×3), and the organic phases were combined, dried over anhydrous sodium sulfate, filtered, concentrated, and the residue was purified by column chromatography (petroleum ether/ethyl acetate=10/1) to obtain compound BB-1-3.

$^1H$ NMR (400 MHz, $CDCl_3$) δ ppm 9.00 (s, 1H), 8.57 (d, J=5.6 Hz, 1H), 7.48-7.37 (m, 2H), 5.78 (d, J=17.6 Hz, 1H), 5.48 (d, J=17.6 Hz, 1H), 3.85 (s, 3H).

Step 3: Synthesis of Compound BB-1-4

At 25° C. and under hydrogen (15 psi) atmosphere, Pd/C (1.80 g, 10% purity) was added to a solution of compound BB-1-3 (1.00 g) in tetrahydrofuran (10.00 mL), stirred for 3 hours, and the reaction mixture was filtered and concentrated to obtain the crude product of compound BB-1-4 (880 mg), which was used directly in the next step.

Step 4: Synthesis of Compound BB-1-5

At 25° C., lithium aluminum hydride (303 mg) was added to a solution of compound BB-1-4 (880 mg) in tetrahydrofuran (10.00 mL) and stirred for 1 hour, and sodium sulfate decahydrate (10 g) was added to the reaction mixture, then water (10 mL) was added thereto.

The reaction mixture was extracted with dichloromethane (10 mL×3), and the organic phases were combined, dried over anhydrous sodium sulfate, filtered and concentrated to obtain the crude product of compound BB-1-5 (470 mg), which was directly used in the next step.

Step 5: Synthesis of the Hydrochloride of Compound BB-1-6

At 25° C., thionyl chloride (2.04 g) was added to a solution of compound BB-1-5 (470 mg) in dichloromethane (5.00 mL) and stirred for 2 hours. Then the reaction solution was directly concentrated to obtain compound BB-1-6 (670 mg, hydrochloride), which was used directly in the next step.

Step 6: Synthesis of Compound BB-1-7

At 25° C., triethylamine (1.06 g) was added to a suspension of compound BB-1-6 (670 mg, hydrochloride) and 4-aminothiophenol (1.31 g) in dichloromethane (5.00 mL) and stirred for 4 hours, and the reaction solution was concentrated and directly purified by column chromatography (petroleum ether/ethyl acetate=4/1 to 0/1) to obtain compound BB-1-7. MS-ESI m/z: 245.0 $[M+H]^+$.

Step 7: Synthesis of Compound BB-1

At 40° C., 30% hydrogen peroxide (2.92 g) was added to a solution of compound BB-1-7 (630 mg) in dichloromethane (10.00 mL), stirred for 18 hours, and then sodium sulfite (10 g) was added thereto, stirred for 30 minutes, and the mixture was filtered. The organic phase was dried over anhydrous sodium sulfate, filtered, concentrated, and the residue was purified by column chromatography to obtain compound BB-1. MS-ESI m/z: 261.1 $[M+H]^+$.

Reference Embodiment 7

BB-2

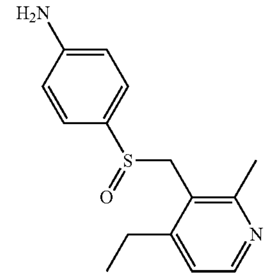

Synthetic Route:

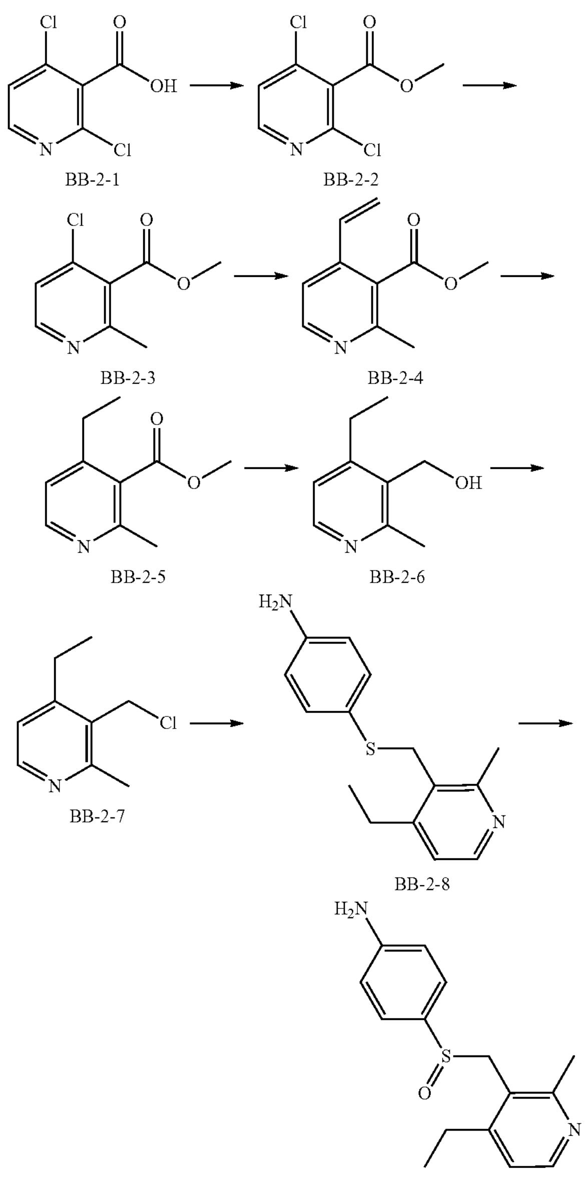

BB-2-1 BB-2-2 BB-2-3 BB-2-4 BB-2-5 BB-2-6 BB-2-7 BB-2-8 BB-2

Step 1: Synthesis of Compound BB-2-2

At 0° C., 2M trimethylsilyldiazomethane (239.06 mL) was slowly added dropwise to a solution of compound BB-2-1 (10 g) in dichloromethane (100 mL) to react for 1 hour. Acetic acid was slowly added dropwise to the reaction solution until no more bubbles were formed, then saturated sodium bicarbonate solution (300 mL) was added thereto, and the reaction solution was extracted with dichloromethane (300 mL×3). The organic phases were combined, washed with saturated brine (500 mL), dried over anhydrous sodium sulfate. After filtration and concentration, the crude product was purified by column chromatography (petroleum ether/ethyl acetate=20/1) to obtain compound BB-2-2. MS-ESI (m/z): 205.9 $[M+1]^+$.

Step 2: Synthesis of Compound BB-2-3

Compound BB-2-2 (11 g) was added to a solution of 50% trimethylboroxine (40.21 g) in water (30 mL) and dimethyl sulfoxide (150 mL) at 80° C. under nitrogen atmosphere, then potassium carbonate (22.14 g) and $Pd(dppf)Cl_2 \cdot CH_2Cl_2$ (4.36 g) were added to react for 12 hours. Water (500 mL) was added to the reaction solution, and the reaction solution was extracted with ethyl acetate (200 mL×3), and the organic phases were combined, washed with saturated brine (1 L), dried over anhydrous sodium sulfate, filtered, concentrated, and the crude product was purified by column chromatography (petroleum ether/ethyl acetate=10/1) to obtain compound BB-2-3. MS-ESI (m/z): 185.9 $[M+1]^+$.

Step 3: Synthesis of Compound BB-2-4

At 25° C., compound BB-2-3 (4.4 g) was added to a solution of potassium vinyltrifluoroborate (9.53 g) in water (10 mL) and dimethyl sulfoxide (50 mL), then potassium carbonate (9.83 g) and $Pd(dppf)Cl_2 \cdot CH_2Cl_2$ (1.94 g) were added thereto, and then the reaction was conducted at 80° C. for 12 hours. Water (100 mL) was added to the reaction solution, and the mixture was extracted with ethyl acetate (50 mL×3). The organic phases were combined, washed with saturated brine (100 mL), dried over anhydrous sodium sulfate. The organic phase was concentrated by rotary evaporation, and the crude product was purified by column chromatography (petroleum ether/ethyl acetate=10/1) to obtain compound BB-2-4. MS-ESI (m/z): 178.0 $[M+1]^+$.

Step 4: Synthesis of Compound BB-2-5

At 25° C., the hydrogenation bottle was washed and dried, and Pd/C (200 mg, 10% purity) was added thereto under argon atmosphere, and then a solution of compound BB-2-4 (1 g) in methanol (20 mL) was poured into the hydrogenation bottle, then the reaction was conducted under hydrogen atmosphere (20 psi) for 12 hours. The reaction solution was filtered through celite, and the filtrate was concentrated by rotary evaporation to obtain the crude product of compound BB-2-5.

Step 5: Synthesis of Compound BB-2-6

At 0° C., a solution of compound BB-2-5 (1.1 g) in tetrahydrofuran (10 mL) was added dropwise to a solution of lithium aluminum hydride (500 mg) in tetrahydrofuran (20 mL), then the reaction was conducted at 25° C. for 1 hour. Water (0.5 mL), 15% NaOH (0.5 mL), water (1.5 mL) were slowly added to the reaction solution; after stirring for 1 hour, the reaction solution was filtered, and the filtrate was dried over anhydrous sodium sulfate and concentrated by rotary evaporation to obtain the crude product of compound BB-2-6. MS-ESI (m/z): 151.9 $[M+1]^+$.

Step 6: Synthesis of Compound BB-2-7

At 0° C., thionyl chloride (2.20 g) was added dropwise to a solution of compound BB-2-6 (930 mg) in dichloromethane (20 mL), and then the reaction was conducted at 25° C. for 40 minutes. The reaction solution was directly rotary evaporated to obtain the crude product of compound BB-2-7. MS-ESI (m/z): 170.0 $[M+1]^+$.

Step 7: Synthesis of Compound BB-2-8

At 25° C., compound BB-2-7 (1 g) was added to a solution of 4-aminothiophenol (1.03 g) and triethylamine (1.79 g) in isopropanol (15 mL) to react for 12 hours, and the reaction solution was concentrated by rotary evaporation, and the crude product was purified by column chromatography (dichloromethane/methanol=100/1 to 20/1) to obtain compound BB-2-8. MS-ESI (m/z): 259.0 $[M+1]^+$.

Step 8: Synthesis of Compound BB-2

Potassium peroxymonosulfate (1.07 g) was added to a solution of compound BB-2-8 (0.9 g) in acetonitrile (25 mL) and water (25 mL), and the reaction solution was stirred at 0° C. for 40 minutes. Saturated sodium sulfite solution was added dropwise to the reaction solution until the starch KI test paper did not turn blue, and the reaction solution was directly concentrated by rotary evaporation to remove $CH_3CN$ and water. The crude product was purified by column chromatography (dichloromethane/methanol=100/1 to 20/1) to obtain compound BB-2. MS-ESI (m/z): 275.0 $[M+1]^+$.

Reference Embodiment 8

BB-3

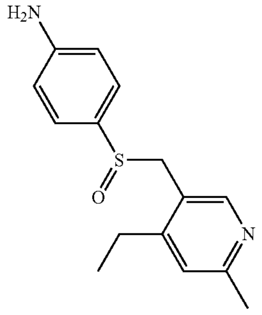

Synthetic Route:

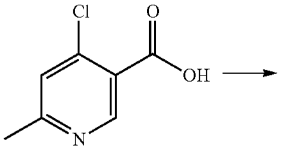

BB-3-1

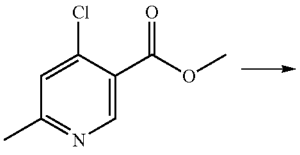

BB-3-2

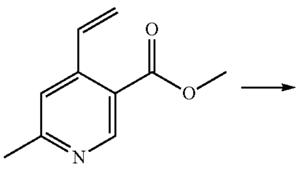

BB-3-3

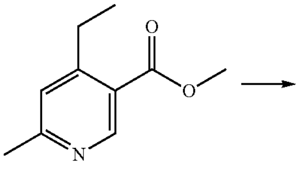

BB-3-4

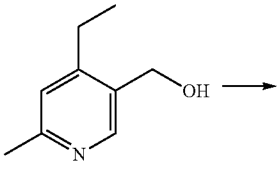

BB-3-5

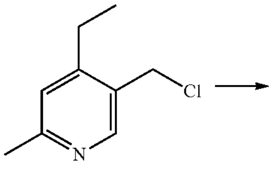

BB-3-6

-continued

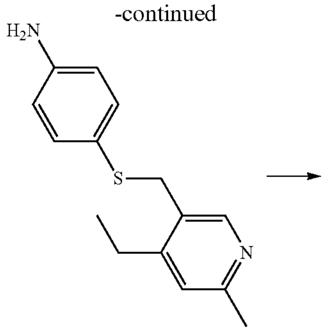

BB-3-7

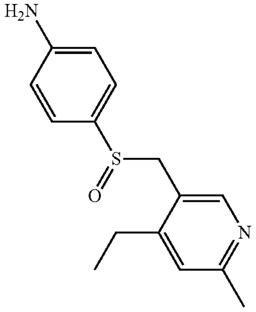

BB-3

Step 1: Synthesis of Compound BB-3-2

At 0° C., 2M trimethylsilyldiazomethane (8.74 mL) was slowly added dropwise to a solution of compound BB-3-1 (2.00 g) in dichloromethane (20 mL) to react for 1 hour, and acetic acid was slowly added dropwise to the reaction solution until no more bubbles were formed, then 30 mL of saturated sodium bicarbonate solution was added thereto. The reaction solution was extracted with dichloromethane (30 mL×3), and the organic phases were combined, washed with saturated brine (50 mL), and dried over anhydrous $Na_2SO_4$. The organic phase was concentrated by rotary evaporation, and the crude product was purified by column chromatography (petroleum ether/ethyl acetate=20/1) to obtain compound BB-3-2. MS-ESI (m/z): 185.9$[M+1]^+$.

Step 2: Synthesis of Compound BB-3-3

At 25° C., potassium carbonate (3.35 g) and Pd(dppf)$Cl_2$·$CH_2Cl_2$ (660 mg) were added to a solution of compound BB-3-2 (3.25 g) and potassium vinyltrifluoroborate (3.25 g) in water (8 mL) and dimethyl sulfoxide (40 mL), and the reaction was conducted at 80° C. for 12 hours. Water (100 mL) was added to the reaction solution, and the reaction solution was extracted with ethyl acetate (50 mL×3), and then the organic phases were combined, washed with saturated brine (100 mL), dried over anhydrous sodium sulfate, filtered, and concentrated by rotary evaporation. The crude product was purified by column chromatography (petroleum ether/ethyl acetate=100/1 to 10/1) to obtain compound BB-3-3. MS-ESI (m/z): 178.0 $[M+1]^+$.

Step 3: Synthesis of Compound BB-3-4

At 25° C., the hydrogenation bottle was washed and dried, and Pd/C (200 mg, 10% purity) was added thereto under argon atmosphere, and a solution of compound BB-3-3 (710 mg) in methanol (20 mL) was poured into the hydrogenation bottle, then the reaction was conducted under the hydrogen atmosphere (15 psi) for 12 hours. The reaction solution was filtered through celite, and the filtrate was concentrated by rotary evaporation to obtain the crude product of compound BB-3-4. MS-ESI (m/z): 180.0 $[M+1]^+$.

Step 4: Synthesis of Compound BB-3-5

At 0° C., lithium aluminum hydride (305 mg) was added to a solution of compound BB-3-4 (720 mg) in tetrahydrofuran (20 mL), and then the reaction was conducted at 25° C. for 1 hour, and water (0.3 mL), 15% NaOH (0.3 mL), water (0.9 mL) were added to the reaction solution. The reaction solution was stirred for 20 minutes and filtered, and the filtrate was dried over anhydrous sodium sulfate, filtered, and concentrated to obtain the crude product of compound BB-3-5. MS-ESI (m/z): 152.0[M+1]$^+$.

Step 5: Synthesis of Compound BB-3-6

At 0° C., thionyl chloride (1.94 g) was added dropwise to a solution of compound BB-3-5 (820 mg) in dichloromethane (20 mL), and then reacted at 25° C. for 40 minutes, and the reaction solution was directly rotary evaporated to obtain the crude product of compound BB-3-6. MS-ESI (m/z): 169.8 [M+1]$^+$.

Step 6: Synthesis of Compound BB-3-7

At 25° C., compound BB-3-6 (920 mg) was added to a solution of 4-aminothiophenol (950 mg) and triethylamine (1.65 g) in isopropanol (15 mL) to react for 12 hours, then the reaction solution was concentrated by rotary evaporation, and the organic phase was concentrated by rotary evaporation, and the crude product was purified by column chromatography (dichloromethane/methanol=100/1 to 20/1) to obtain compound BB-3-7. MS-ESI (m/z): 259.1 [M+1]$^+$.

Step 7: Synthesis of Compound BB-3

Potassium peroxymonosulfate (310.50 mg) was added to a solution of compound BB-3-7 (290 mg) in acetonitrile $CH_3CN$ (15 mL) and water (15 mL), and the reaction solution was stirred at 0° C. for 40 minutes. Saturated sodium sulfite solution was added dropwise to the reaction solution until the starch KI test paper did not turn blue, and the reaction solution was directly concentrated by rotary evaporation to remove acetonitrile and water. The crude product was purified by column chromatography (dichloromethane/methanol=100/1 to 20/1) to obtain compound BB-3. MS-ESI (m/z): 275.0 [M+1]$^+$.

Reference Embodiment 9

BB-4

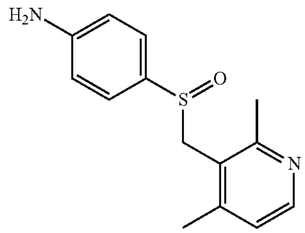

Synthetic Route:

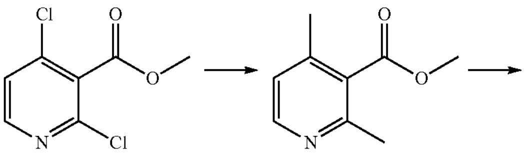

BB-4-1 BB-4-2

-continued

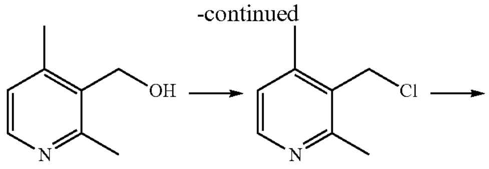

BB-4-3 BB-4-4

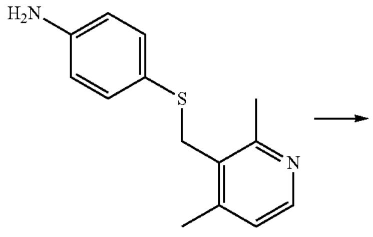

BB-4-5

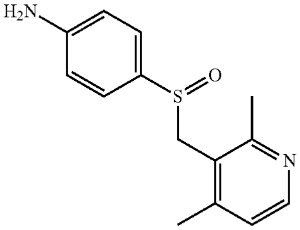

BB-4

Step 1: Synthesis of Compound BB-4-2

Trimethylboroxine (30.47 g, 50% purity) was added to a solution of compound BB-4-1 (5 g) and cesium carbonate (15.81 g) in dioxane (150 mL) and water (15 mL) at 25° C. under nitrogen protection, then Pd(dppf)$Cl_2$ (888 mg) was added thereto, and then the reaction solution was stirred at 100° C. under nitrogen protection for 17 hours. The reaction solution was poured into water (200 mL), and then extracted three times with ethyl acetate (150 mL×3), and the combined organic phases were washed once with water (100 mL), washed three times with saturated brine (100 mL), dried over anhydrous sodium sulfate, filtered and concentrated under reduced pressure to obtain a yellow oil. The yellow oil was separated by silica gel column chromatography (petroleum ether:ethyl acetate=20:1 to 4:1) to obtain compound BB-4-2. MS-ESI (m/z): 166.0[M+1]$^+$.

Step 2: Synthesis of Compound BB-4-3

At 0° C., lithium aluminum hydride (712 mg) was added to a solution of compound BB-4-2 (3.1 g) in tetrahydrofuran (30 mL), and then the whole mixture was stirred at 0° C. for 3 hours. Water, 15% sodium hydroxide aqueous solution, water (0.7 mL, 2.1 mL, 0.7 mL) were added to the reaction solution sequentially, and stirred at 10-minute intervals, then the mixture was filtered through celite, and the filtrate was concentrated under reduced pressure to obtain the crude product of compound BB-4-3. MS-ESI (m/z): [M+1]$^+$.

Step 3: Synthesis of Compound BB-4-4

At 0° C., thionyl chloride (4.51 g) was added to a solution of compound BB-4-3 (2.6 g) in dichloromethane (25 mL), and then the whole mixture was stirred at 45° C. for 2 hours. The reaction solution was directly concentrated under reduced pressure to obtain the crude product of compound BB-4-4. MS-ESI (m/z): 155.8 [M+1]$^+$.

Step 4: Synthesis of Compound BB-4-5

At 0° C., triethylamine (5.75 g) was added to a solution of compound BB-4-4 (3.64 g) in isopropanol (30 mL), then the reaction mixture was stirred for ten minutes, and then 4-aminothiophenol was added to the above mixture, and the whole mixture was stirred at 25° C. under nitrogen for 20 hours. The reaction solution was directly concentrated under reduced pressure to obtain a solid residue. The solid residue was separated by silica gel column chromatography (dichloromethane:methanol=100:1 to 15:1) to obtain compound BB-4-5. MS-ESI (m/z): 244.9$[M+1]^+$.

Step 5: Synthesis of Compound BB-4

At 0° C., potassium peroxymonosulfate (2.52 g) was added to a solution of compound BB-4-5 (2 g) in acetonitrile (10 mL) and water (10 mL), and the reaction solution was stirred at 0° C. for 0.5 hours. The reaction solution was added to saturated sodium sulfite aqueous solution (30 mL) for quenching, and after quenching, the reaction solution was also directly concentrated under reduced pressure to remove acetonitrile and water, and then a mixed solution of dichloromethane:methanol (10:1) was added to the above-mentioned mixture (150 mL), stirred for 1 hour, and then the mixture was filtered through celite. The filtrate was concentrated under reduced pressure to obtain a pale yellow solid, then dichloromethane (20 mL) was added to the above-mentioned mixture, stirred for 1 hour, and then the mixture was filtered through celite, and the filtrate was concentrated under reduced pressure to obtain a pale yellow solid. The pale yellow solid was separated by silica gel column chromatography (dichloromethane:methanol=100:1 to 20:1) to obtain compound BB-4. MS-ESI (m/z): 260.9 $[M+1]^+$.

Reference Embodiment 10

BB-5

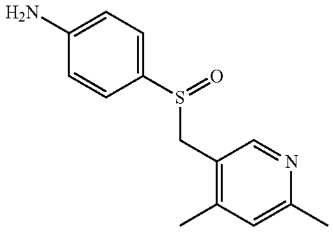

Synthetic Route:

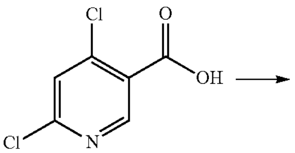

BB-5-1

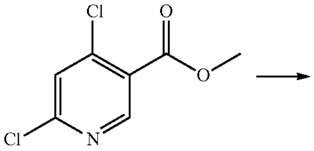

BB-5-2

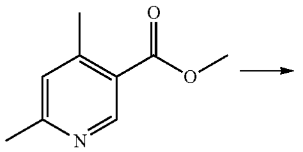

BB-5-3

-continued

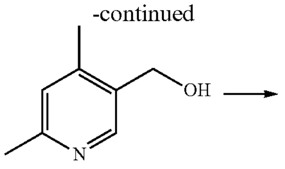

BB-5-4

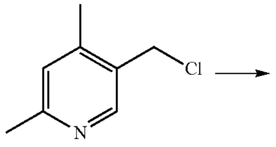

BB-5-5

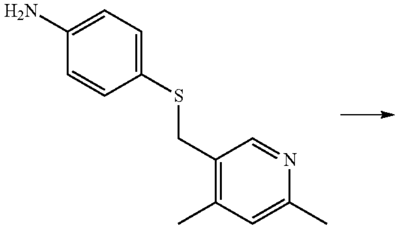

BB-5-6

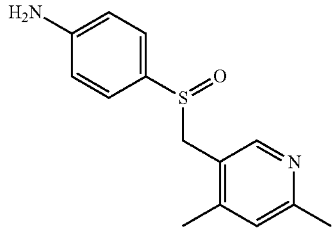

BB-5

Step 1: Synthesis of Compound BB-5-2

At 0° C., trimethylsilyldiazomethane (2 M, 19.53 mL) was slowly added dropwise to a solution of compound BB-5-1 (5 g) in dichloromethane (50 mL) and methanol (5 mL), and the reaction was conducted at 0° C. for 1 hour; first, acetic acid was added dropwise to the reaction solution until no bubbles were formed, then saturated sodium bicarbonate solution (50 mL) was added and extracted with dichloromethane (50 mL×3). The organic phases were combined and washed once with saturated brine (50 mL), dried over anhydrous sodium sulfate, filtered and concentrated under reduced pressure to obtain the crude product of compound BB-5-2. MS-ESI (m/z): 205.8 $[M+1]^+$.

Step 2: Synthesis of Compound BB-5-3

Compound 50% trimethylboroxine (26.94 g, 50% purity) was added to a solution of BB-5-2 (5.4 g) and cesium carbonate (17.08 g) in dioxane (150 mL) and water (15 mL) at 25° C. under nitrogen protection, then Pd(dppf)$Cl_2$ (575 mg) was added to the above-mentioned mixture, and the whole reaction solution was stirred at 100° C. for 15 hours under nitrogen protection. The reaction solution was added to water (200 mL), then extracted three times with ethyl acetate (150 mL×3), and the combined organic phases were washed once with water (100 mL), washed three times with saturated brine (100 mL), dried over anhydrous sodium sulfate, filtered and concentrated under reduced pressure, then separated by silica gel column chromatography (petroleum ether:ethyl acetate=20:1 to 4:1) to obtain compound BB-5-3. MS-ESI (m/z): 166.0$[M+1]^+$.

Step 3: Synthesis of Compound BB-5-4

At 0° C., lithium aluminum hydride (12 mg) was added to a solution of compound BB-5-3 (0.05 g) in tetrahydrofuran (30 mL), and then the whole mixture was stirred at 0° C. for 1 hour. Sodium sulfate decahydrate was added to the reaction solution, stirred for 20 minutes, then the mixture was filtered through celite, and the filtrate was concentrated under reduced pressure to obtain the crude product of compound BB-5-4.

Step 4: Synthesis of Compound BB-5-5

At 0° C., thionyl chloride (69 mg) was added to a solution of compound BB-5-4 (0.04 g) in dichloromethane (10 mL), and then the whole mixture was stirred at 45° C. for 3 hours.

The reaction solution was directly concentrated under reduced pressure to obtain the crude product of compound BB-5-5. MS-ESI (m/z): 155.8[M+1]$^+$.

Step 5: Synthesis of Compound BB-5-6

At 0° C., triethylamine (109 mg) was added to a solution of compound BB-5-5 (0.056 g) in isopropanol (20 mL), then the reaction solution was stirred for ten minutes, and then 4-aminothiophenol (68 mg) was added to the above-mentioned mixture, then the whole mixture was stirred at 25° C. under nitrogen protection for 12 hours. The reaction solution was directly concentrated under reduced pressure and then separated by silica gel column chromatography (dichloromethane:methanol=100:1 to 15:1) to obtain compound BB-5-6. MS-ESI (m/z): 244.9 [M+1]$^+$.

Step 6: Synthesis of Compound BB-5

At 0° C., potassium peroxymonosulfate (88.06 mg) was added to a solution of compound BB-5-6 (0.07 g) in acetonitrile (10 mL) and water (10 mL), and the reaction was conducted for 1 hour. The reaction solution was added to saturated sodium sulfite aqueous solution (30 mL) for quenching, and after quenching, the reaction solution was directly concentrated under reduced pressure to remove acetonitrile and water, and then a mixed solution (150 mL) of dichloromethane:methanol (10:1) was added to the above-mentioned mixture, stirred for 1 hour, and then the reaction mixture was filtered through celite. The filtrate was concentrated under reduced pressure to obtain a pale yellow solid, then dichloromethane (20 mL) was added to the above-mentioned mixture, stirred for 1 hour, and then the mixture was filtered through celite, and the filtrate was concentrated under reduced pressure and then separated by silica gel plate (dichloromethane:methanol=100:1 to 15:1) to obtain compound BB-5. MS-ESI (m/z): 260.9 [M+1]$^+$.

Reference Embodiment 11

BB-6

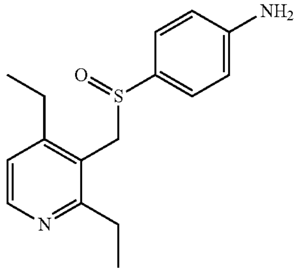

Synthetic Route:

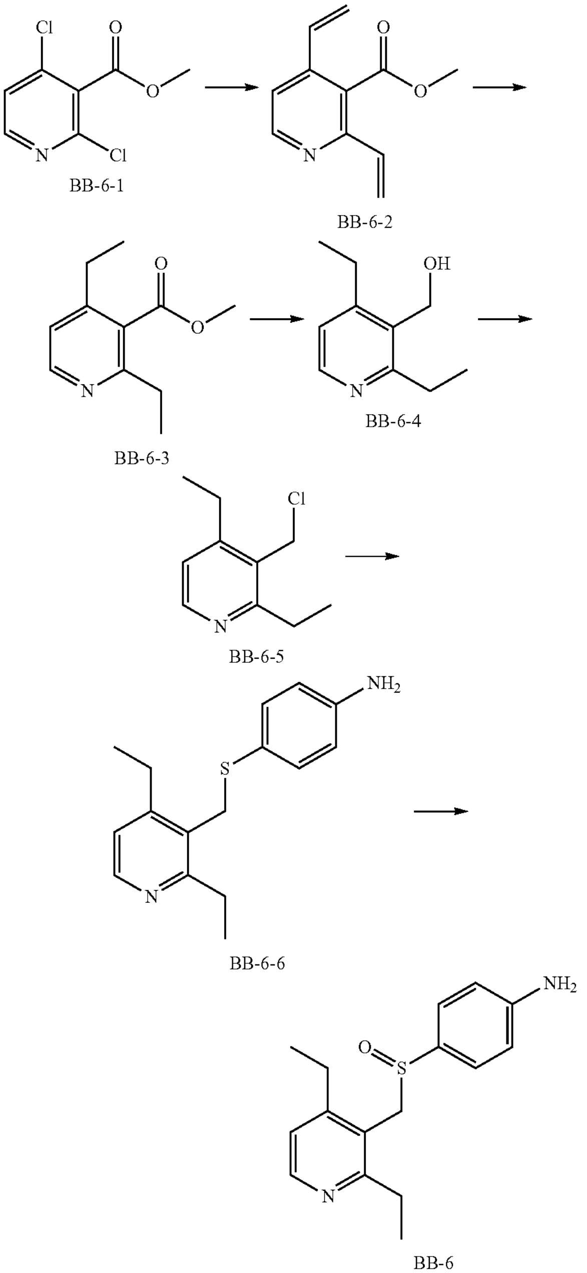

Step 1: Synthesis of Compound BB-6-2

At 25° C., compound BB-6-1 (5 g) was added to a solution of potassium vinyltrifluoroborate (13.00 g) in dioxane (100 mL) and water (10 mL), then potassium carbonate (6.71 g) and Pd(dppf)$Cl_2$·$CH_2Cl_2$ (991 mg) were added thereto, and then the reaction solution was reacted at 100° C. for 12 hours. Water (300 mL) was added to the reaction solution, and the reaction solution was extracted with ethyl acetate (100 mL×3). The organic phases were combined and washed with saturated brine (300 mL) and dried over anhydrous sodium sulfate. The organic phase was concentrated by rotary evaporation, and the crude product was purified by column chromatography (petroleum ether/ethyl acetate=100/1 to 10/1) to obtain compound BB-6-2. MS-ESI (m/z): 190.0 [M+1]$^+$.

Step 2: Synthesis of Compound BB-6-3

At 25° C., the hydrogenation bottle was washed and dried, and Pd/C (150 mg, 10% purity) was added under argon atmosphere, and then a solution of compound BB-6-2 (280 mg) in MeOH (15 mL) was poured into the hydrogenation bottle, then the reaction was conducted at 40° C. for 12 hours under a hydrogen atmosphere (40 psi). The reaction solution was filtered through celite, and the filtrate was concentrated by rotary evaporation to obtain the crude product of compound BB-6-3. MS-ESI (m/z): 194.0 $[M+1]^+$.

Step 3: Synthesis of Compound BB-6-4

Compound BB-6-3 (0.33 g) was dissolved in tetrahydrofuran (3 mL), then the solution was stirred under ice bath for 10 minutes, then lithium aluminum hydride (71 mg) was added to react for 2 hours. Water:15% NaOH:water=1:1:3 was used to quench, then the reaction mixture was filtered and concentrated to obtain the crude product of compound BB-6-4. MS-ESI (m/z): 166.0 $[M+1]^+$.

Step 4: Synthesis of Compound BB-6-5

At 25° C., compound BB-6-4 (0.37 g) was dissolved in dichloromethane (3 mL), then thionyl chloride (799 mg) was added thereto under ice bath, then the reaction solution was stirred at 40° C. for 1 hour. The reaction solution was directly concentrated to obtain the crude product of compound BB-6-5. MS-ESI (m/z): 183.9 $[M+1]^+$.

Step 5: Synthesis of Compound BB-6-6

At 25° C., compound BB-6-5 (0.411 g) and 4-aminothiophenol (364 mg) were dissolved in isopropanol (10 mL), then triethylamine (679 mg) was added thereto. The reaction was conducted at 25° C. under nitrogen protection for 12 hours, and the solution was concentrated and purified by column chromatography (dichloromethane:methanol=100:1 to 15:1) to obtain compound BB-6-6. MS-ESI (m/z): 273.1 $[M+1]^+$.

Step 6: Synthesis of Compound BB-6

At 25° C., compound BB-6-6 (0.56 g) was dissolved in a mixed solvent of water (3 mL) and acetonitrile (3 mL), then potassium peroxymonosulfate (505 mg) was added thereto, and the mixture was stirred at 25° C. for 1 hour; firstly the reaction was quenched by adding 50 mL of saturated sodium sulfite solution, then the reaction solution was extracted three times with ethyl acetate (50 mL×3). The combined organic phases were washed once with saturated brine, then dried over anhydrous sodium sulfate, filtered and concentrated. The residue was purified by column chromatography (dichloromethane:methanol=100:1 to 15:1) to obtain compound BB-6. MS-ESI (m/z): 289.1 $[M+1]^+$.

$^1H$ NMR (400 MHz, $CDCl_3$) δ=8.39 ppm (d, J=5.2 Hz, 1H), 7.21 (d, J=8.4 Hz, 2H), 6.98 (d, J=5.6 Hz, 1H), 6.69 (d, J=8.4 Hz, 2H), 4.38 (d, J=12.80 Hz, 1H), 3.95-4.05 (m, 3H), 2.68 (br d, J=7.6 Hz, 2H), 2.55 (br dd, J=7.6, 4.4 Hz, 2H), 1.23 (t, J=7.6 Hz, 3H), 1.17 (t, J=7.6 Hz, 3H).

Embodiment 1

WX001

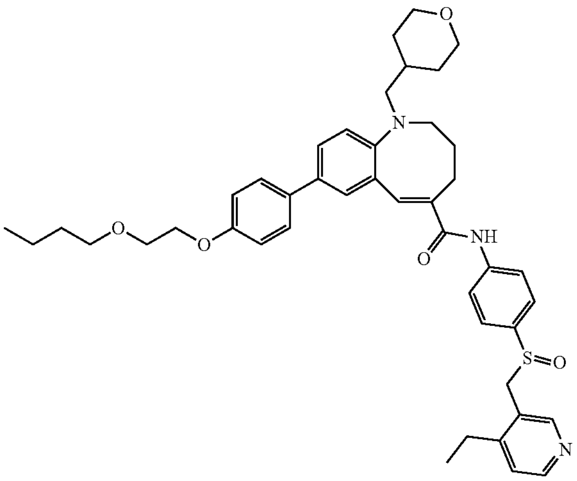

Synthetic Route:

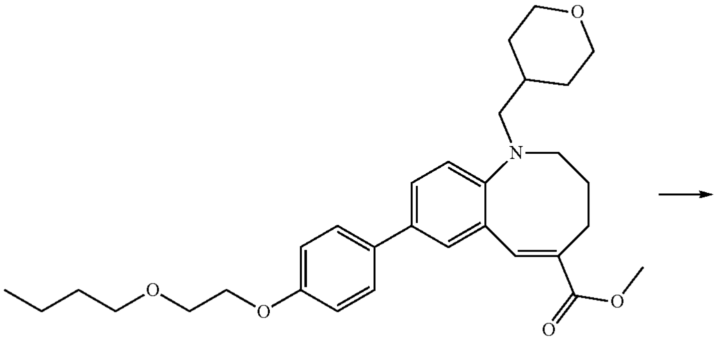

AA-3A

-continued

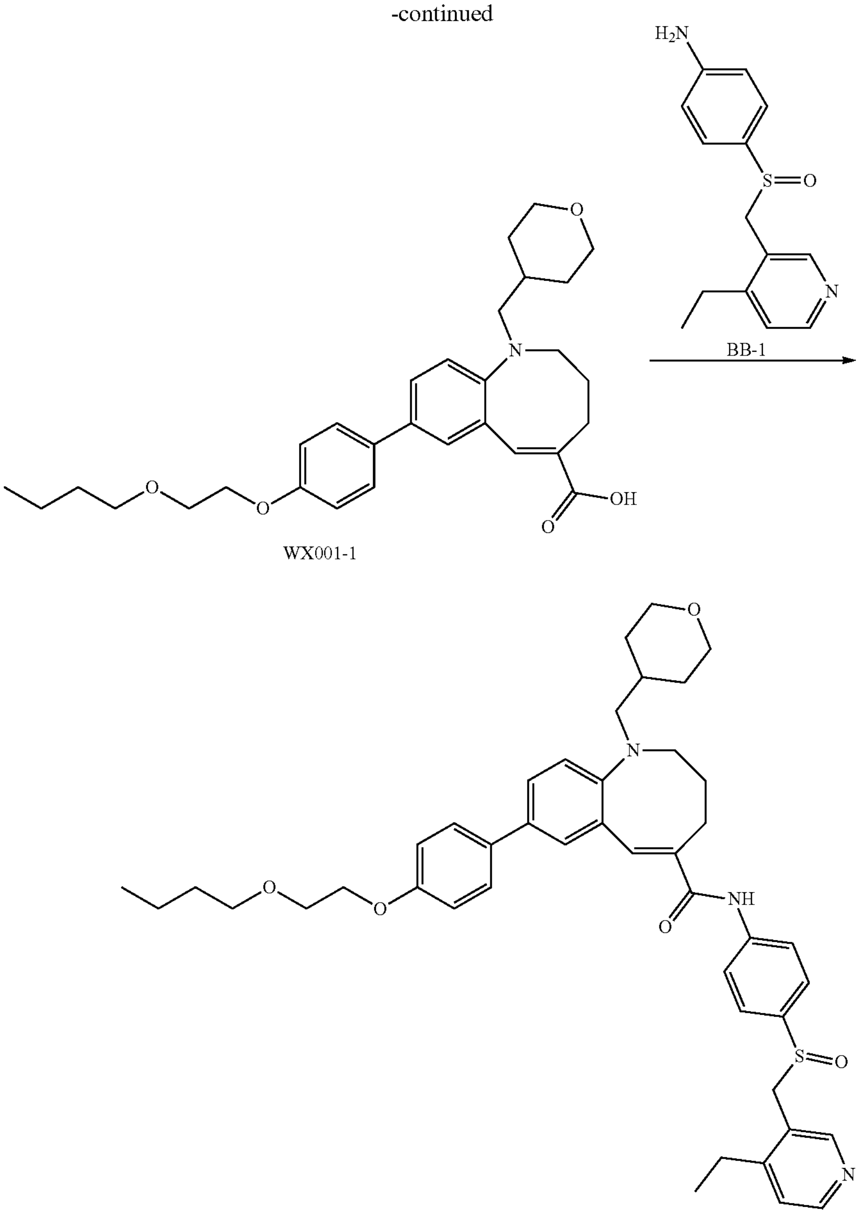

WX001-1

BB-1

WX001

Step 1: Synthesis of Compound WX001-1

Compound AA-3A (0.603 g) was dissolved in methanol (10 mL) and water (2 mL) at 25° C., then sodium hydroxide (521 mg) was added thereto, and the reaction solution was heated to 50° C. and stirred for 43 hours. The reaction solution was adjusted to pH=3 with 2M dilute hydrochloric acid solution, extracted with ethyl acetate (30 mL×3). The organic phases were combined, washed once with saturated brine (100 mL), dried over anhydrous sodium sulfate, filtered to remove anhydrous sodium sulfate, and the filtrate was concentrated under reduced pressure and the solvent was evaporated to obtain compound WX001-1. MS-ESI (m/z): 494.20 $[M+1]^+$.

Step 2: Synthesis of Compound WX001

At 25° C., EDCI (74 mg) was added to a solution of compounds WX001-1 (95 mg) and BB-1 (0.05 g, 192.05 μmol, 1 eq) in pyridine (3 mL), then the whole mixture was stirred at 60° C. under nitrogen protection for 4 hours. 50 mL of ethyl acetate was added to the reaction solution, then the reaction solution was concentrated under reduced pressure. The residue was directly separated by preparative plate (dichloromethane:methanol=12:1) to obtain compound WX001.

MS-ESI (m/z): 736.5 $[M+1]^+$.

$^1H$ NMR (400 MHz, $CDCl_3$) δ ppm 0.94 (t, J=7.40 Hz, 3H), 1.25 (t, J=7.4 Hz, 3H), 1.33-1.49 (m, 4H), 1.57-1.64 (m, 4H), 1.68-1.75 (m, 2H), 2.03-2.16 (m, 1H), 2.61 (br s, 2H), 2.69 (q, J=7.3 Hz, 2H), 3.17 (br d, J=6.4 Hz, 2H), 3.39 (br t, J=11.4 Hz, 2H), 3.49-3.59 (m, 4H), 3.74-3.85 (t, J=4.8 Hz 2H), 4.02 (br dd, J=11.4, 7.8 Hz, 2H), 4.06-4.13 (d, J=12.8 Hz 1H), 4.13-4.22 (m, 3H), 6.85 (br d, J=8.8 Hz, 1H), 6.98 (d, J=8.8 Hz, 2H), 7.17 (d, J=4.8 Hz, 1H), 7.36 (d, J=8.4 Hz, 3H), 7.40-7.50 (m, 3H), 7.53 (s, 1H), 7.74 (d, J=8.4 Hz, 2H), 7.79-7.90 (m, 2H), 8.43 (d, J=5.2 Hz, 1H).

Embodiment 2
WX002 or WX003
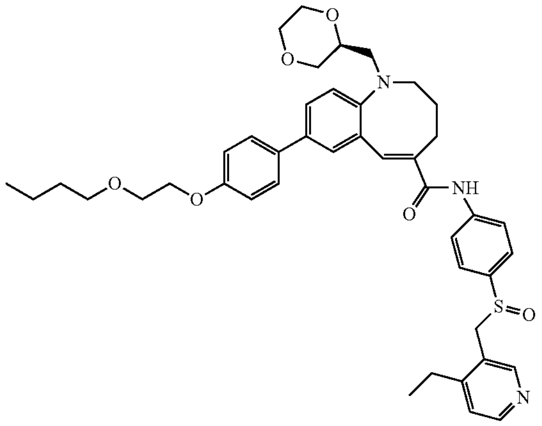
WX003 or WX002
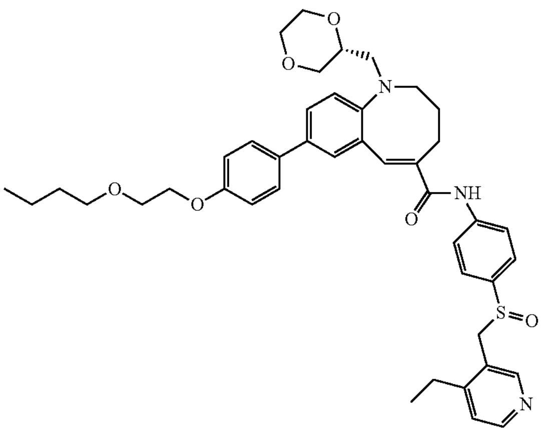
Synthetic Route:
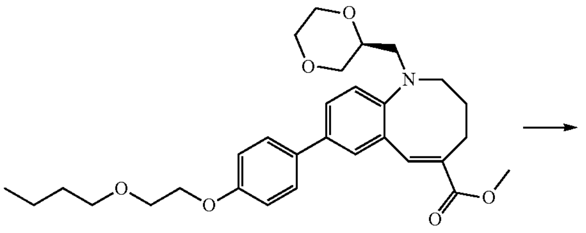
AA-3C-A or AA-3C-B
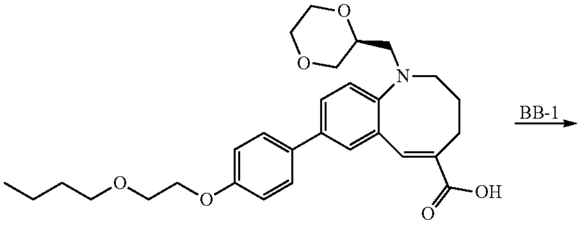
WX002-1 or WX003-1
-continued
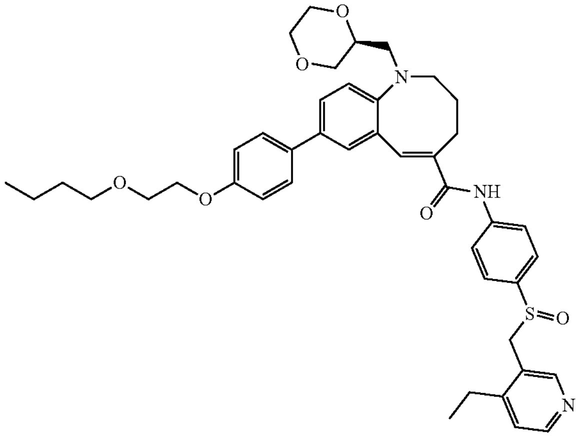
WX002 or WX003
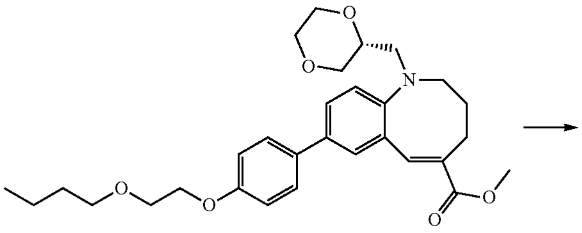
AA-3C-B or AA-3C-A
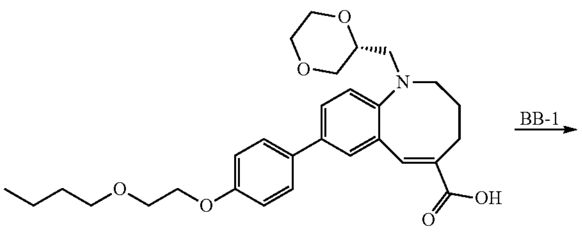
WX003-1 or WX002-1
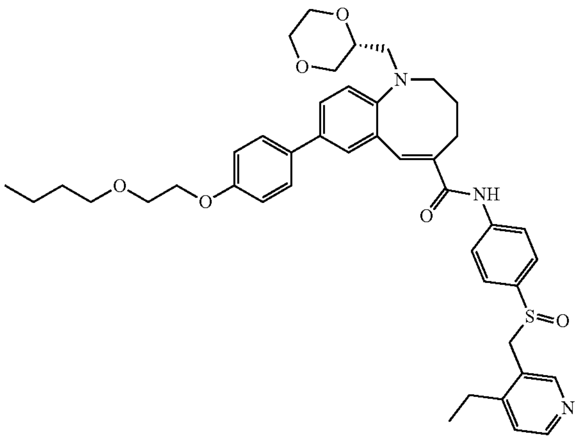
WX003 or WX002

Step 1: Synthesis of Compound WX002-1

At 25° C., sodium hydroxide (353 mg) was added to a solution of compound AA-3C-B (0.9 g) in methanol (10 mL) and water (2 mL), and the whole mixture was stirred at 60° C. for 18.5 hours. The mixture was first concentrated under reduced pressure by rotary evaporation to remove methanol, then the concentrated oil was adjusted to pH=3 with 2M dilute hydrochloric acid, and the above mixture was extracted three times with ethyl acetate (50 mL×3), and the combined organic phases were washed once with saturated brine (50 mL), dried over anhydrous sodium sulfate, filtered and concentrated under reduced pressure to obtain compound WX002-1. MS-ESI (m/z): 496.3 $[M+1]^+$.

Step 2: Synthesis of Compound WX002

At 25° C., EDCI (74 mg) was added to a solution of compounds WX002-1 (95 mg) and BB-1 (50 mg) in pyridine (3 mL), then the whole mixture was stirred at 60° C. under nitrogen protection for 4 hours. 50 mL of ethyl acetate was added to the reaction solution, then the reaction solution was concentrated under reduced pressure to obtain a yellow oil. The yellow oil was directly separated by prep-TLC ($SiO_2$, DCM:MeOH=12:1) to obtain compound WX002. MS-ESI (m/z): 738.6 $[M+1]^+$.

$^1H$ NMR (400 MHz, $CDCl_3$) δ ppm 0.94 (t, J=7.2 Hz, 3H), 1.24 (t, J=7.6 Hz, 3H), 1.34-1.47 (m, 2H), 1.50-1.67 (m, 6H), 2.58 (br s, 2H), 2.68 (q, J=7.6 Hz, 2H), 3.19-3.36 (m, 2H), 3.37-3.53 (m, 2H), 3.56 (t, J=6.8 Hz, 2H), 3.61-3.72 (m, 2H), 3.72-3.78 (m, 2H), 3.78-3.85 (m, 3H), 3.88 (dd, J=11.6, 2.0 Hz, 1H), 3.94-4.03 (m, 1H), 4.05-4.12 (m, 1H), 4.13-4.22 (m, 3H), 6.88-6.98 (m, 2H), 7.16 (d, J=5.2 Hz, 2H), 7.36 (d, J=8.4 Hz, 3H), 7.40-7.48 (m, 3H), 7.52 (s, 1H), 7.74 (d, J=8.8 Hz, 2H), 7.84 (s, 1H), 7.91 (br s, 1H), 8.43 (d, J=5.2 Hz, 1H).

Step 3: Synthesis of Compound WX003-1

At 25° C., sodium hydroxide (353 mg) was added to a solution of compound AA-3C-A (0.9 g) in methanol (10 mL) and water (2 mL), and the whole mixture was stirred at 60° C. for 18.5 hours. The mixture was first concentrated under reduced pressure by rotary evaporation to remove methanol, then the concentrated oil was adjusted to pH=3 with 2M dilute hydrochloric acid, and the above mixture was extracted three times with ethyl acetate (50 mL×3), and the combined organic phases were washed once with saturated brine (50 mL), dried over anhydrous sodium sulfate, filtered and concentrated under reduced pressure to obtain compound WX003-1. MS-ESI (m/z): 496.2 $[M+1]^+$.

Step 4: Synthesis of Compound WX003

At 25° C., EDCI (74 mg) was added to a solution of compounds WX003-1 (95 mg) and BB-1 (50 mg) in pyridine (3 mL), then the whole mixture was stirred at 60° C. under nitrogen protection for 4 hours. 50 mL of ethyl acetate was added to the reaction solution, then the reaction solution was concentrated under reduced pressure, and then separated by prep-TLC ($SiO_2$, DCM:MeOH=12:1) to obtain compound WX003. MS-ESI (m/z): 738.6 $[M+1]^+$;

$^1H$ NMR (400 MHz, $CDCl_3$) δ ppm 0.94 (t, J=7.2 Hz, 3H), 1.25 (t, J=7.2 Hz, 3H), 1.33-1.46 (m, 2H), 1.55-1.65 (m, 4H), 2.59 (br s, 2H), 2.69 (q, J=7.8 Hz, 2H), 3.21-3.35 (m, 2H), 3.37-3.53 (m, 2H), 3.56 (t, J=6.6 Hz, 2H), 3.61-3.78 (m, 4H), 3.78-3.85 (m, 3H), 3.85-3.91 (m, 1H), 3.98 (br s, 1H), 4.07-4.20 (m, 4H), 6.89 (d, J=8.8 Hz, 1H), 6.98 (d, J=8.8 Hz, 2H), 7.18 (d, J=5.2 Hz, 1H), 7.36 (m, 3H), 7.40-7.49 (m, 3H), 7.53 (s, 1H), 7.74 (d, J=8.8 Hz, 2H), 7.81-7.89 (m, 2H), 8.43 (d, J=5.2 Hz, 1H).

Embodiment 3

WX004 or WX005

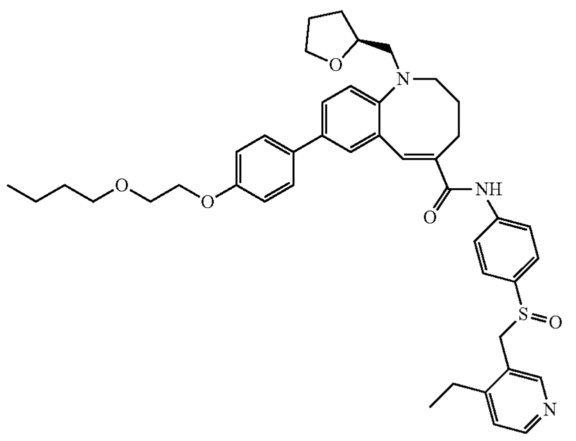

WX005 or WX004

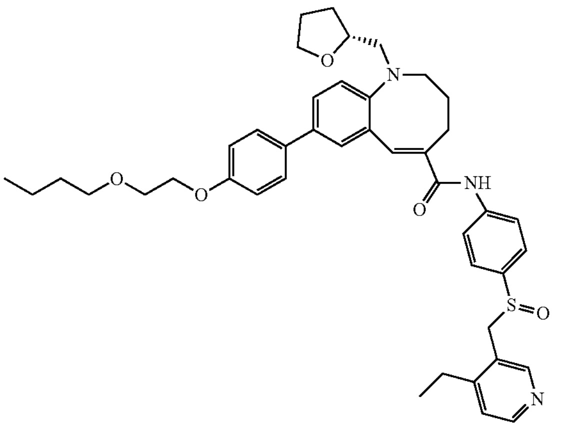

Synthetic Route:

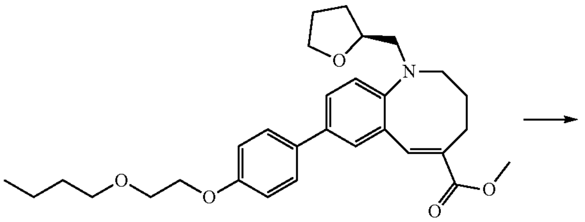

AA-3B-A or AA-3B-B

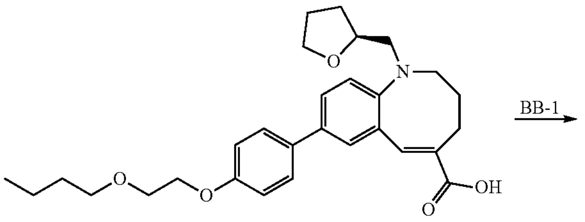

WX004-1 or WX005-1

-continued

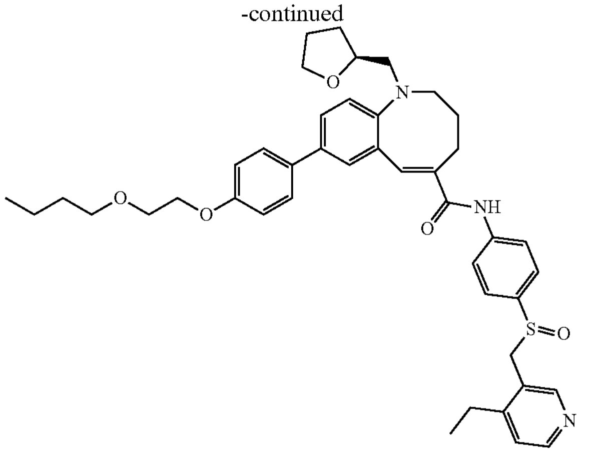

WX004 or WX005

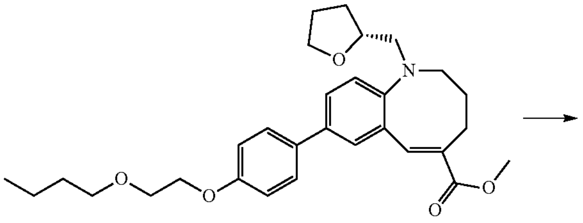

AA-3B-B or AA-3B-A

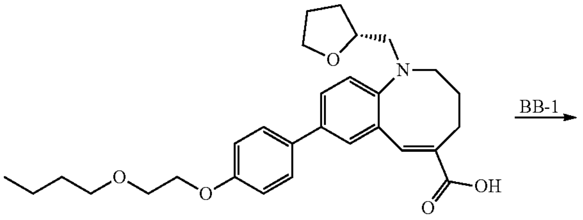

WX005-1 or WX004-1

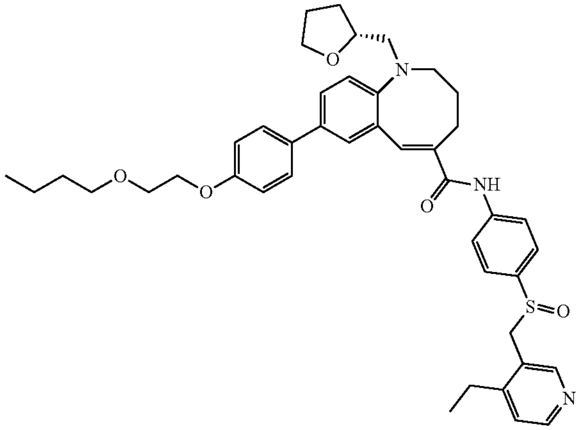

WX005 or WX004

Step 1: Synthesis of Compound WX004-1

At 25° C., compound AA-3B-A (470 mg) was dissolved in a mixed solution of methanol (10 mL) and water (2 mL), then sodium hydroxide (114 mg) was added thereto, and the mixture was stirred at 50° C. for 14 hours. The solution was concentrated under reduced pressure, then adjusted to pH=5-6 with dilute hydrochloric acid solution, then extracted three times with ethyl acetate (20 mL×3). The combined organic phases were washed once with saturated brine, and then dried over anhydrous sodium sulfate, filtered and concentrated under reduced pressure, and compound WX004-1 was obtained. MS-ESI (m/z): 480.2 $[M+1]^+$.

Step 2: Synthesis of Compound WX004

At 25° C., EDCI (74 mg) was added to a solution of compounds WX004-1 (92 mg) and BB-1 (50 mg) in pyridine (3 mL), and the whole mixture was then stirred at 60° C. under nitrogen protection for 4 hours. 50 mL of ethyl acetate was added to the reaction solution, then concentrated under reduced pressure and separated by prep-TLC ($SiO_2$, DCM: MeOH=12:1) to obtain compound WX004. MS-ESI (m/z): 722.4 (M+1)+;

$^1H$ NMR (400 MHz, $CDCl_3$) δ ppm 0.94 (t, J=7.4 Hz, 3H), 1.24 (t, J=7.6 Hz, 3H), 1.34-1.47 (m, 2H), 1.53-1.65 (m, 6H), 1.85-2.03 (m, 2H), 2.06-2.18 (m, 1H), 2.60 (br s, 2H), 2.63-2.73 (m, 2H), 3.32-3.47 (m, 2H), 3.56 (t, J=6.6 Hz, 2H), 3.66-3.75 (m, 1H), 3.75-3.84 (m, 3H), 3.90-3.98 (m, 1H), 4.04-4.11 (m, 1H), 4.14-4.18 (m, 3H), 4.19-4.28 (m, 1H), 6.86-7.04 (m, 3H), 7.16 (d, J=5.2 Hz, 1H), 7.29-7.49 (m, 6H), 7.53 (s, 1H), 7.74 (d, J=8.8 Hz, 2H), 7.86 (s, 1H), 7.94 (br s, 1H), 8.43 (d, J=5.2 Hz, 1H).

Step 3: Synthesis of Compound WX005-1

At 25° C., compound AA-3B-B (450 mg) was dissolved in a mixture of water (2 mL) and methanol (10 mL), then sodium hydroxide (109 mg) was added thereto, and stirred at 50° C. for 14 hours. The solution was concentrated under reduced pressure, then adjusted to pH=5-6 with dilute hydrochloric acid solution, then extracted three times with ethyl acetate (20 mL×3). The combined organic phases were washed once with saturated brine, then dried over anhydrous sodium sulfate, filtered and concentrated under reduced pressure to obtain compound WX005-1, which was directly used in the next step. MS-ESI (m/z): 480.2 $[M+1]^+$.

Step 4: Synthesis of Compound WX005

At 25° C., EDCI (74 mg) was added to a solution of compounds WX005-1 (92 mg) and BB-1 (50 mg) in pyridine (3 mL), and then the whole mixture was stirred at 60° C. under nitrogen protection for 3 hours. 50 mL of ethyl acetate was added to the reaction solution, then the reaction solution was concentrated under reduced pressure and then separated by prep-TLC ($SiO_2$, DCM:MeOH=12:1) to obtain compound WX005. MS-ESI (m/z): 722.4 $(M+1)^+$;

$^1H$ NMR (400 MHz, $CDCl_3$) δ ppm 0.94 (t, J=7.4 Hz, 3H), 1.24 (t, J=7.4 Hz, 3H), 1.34-1.47 (m, 2H), 1.50-1.65 (m, 6H), 1.85-2.04 (m, 2H), 2.11 (br dd, J=7.4, 5.0 Hz, 1H), 2.60 (br s, 2H), 2.67 (q, J=7.6 Hz, 2H), 3.30-3.48 (m, 2H), 3.56 (t, J=6.6 Hz, 2H), 3.70 (m, 1H), 3.76-3.84 (m, 3H), 3.89-3.98 (m, 3H), 4.04-4.12 (m, 1H), 4.13-4.22 (m, 3H), 4.24 (br s, 1H), 6.88-7.03 (m, 3H), 7.16 (d, J=5.2 Hz, 1H), 7.31-7.48 (m, 6H), 7.53 (s, 1 H), 7.74 (d, J=8.4 Hz, 2H), 7.86 (s, 1H), 7.93 (br s, 1H), 8.43 (d, J=5.2 Hz, 1H).

Embodiment 4

WX006 or WX007

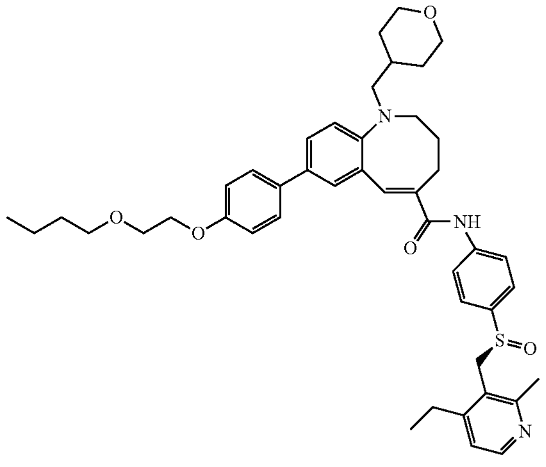

WX007 or WX006

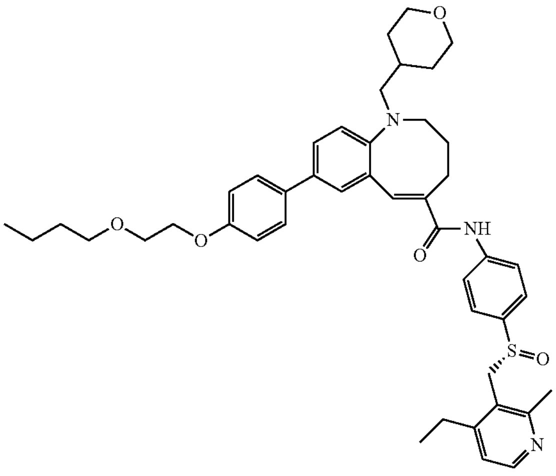

Synthetic Route:

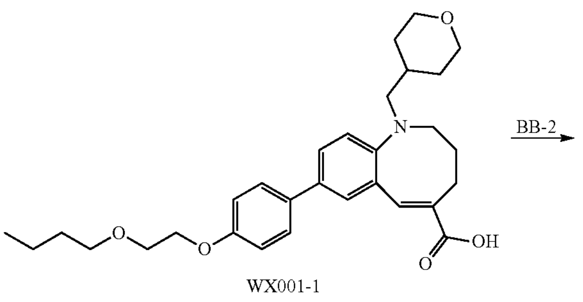

WX001-1

-continued

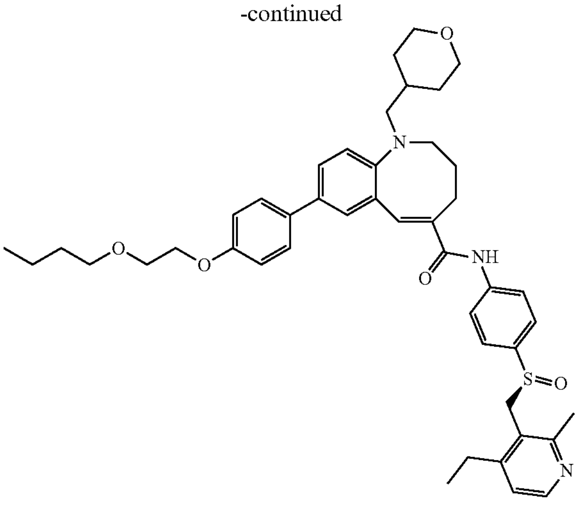

WX006 or WX007

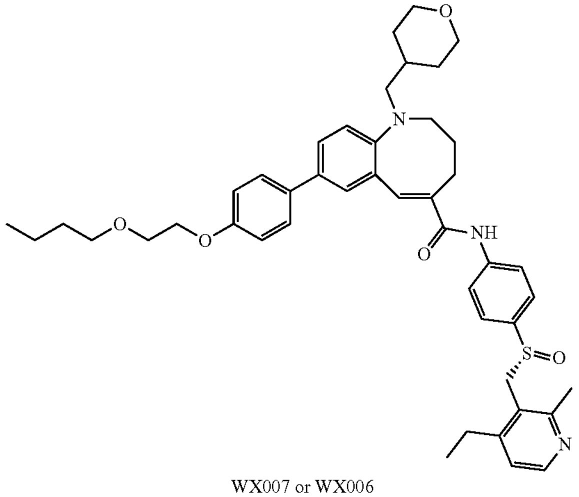

WX007 or WX006

At 60° C., compound BB-2 (50 mg) and EDCI (70 mg) were added to a solution of compound WX001-1 (90 mg) in pyridine (3 mL) to react for 4 hours, and the reaction solution was concentrated to remove the pyridine and then water (20 mL) was added thereto. The reaction solution was extracted with DCM/MeOH=20/1 (20 mL×2), and the organic phases were combined, washed with saturated brine (20 mL) and dried over anhydrous sodium sulfate. Then the organic phases were filtered, concentrated and the residue was purified by pre.TLC (DCM/MeOH=15/1) and then split by SFC to obtain compounds WX006 (retention time: 9.742 min) and WX007 (retention time: 11.790 min).

SFC splitting condition: column type: ChiralPak AD-3 150×4.6 mm I.D., 3 m; mobile phase: A: $CO_2$ B:IPA (0.05% DEA); gradient: 40% B; flow rate: 2.5 mL/min; column temperature: 40° C.; column pressure: 100 bar.

WX006 MS-ESI (m/z): 750.2 $(M+1)^+$ $^1H$ NMR (400 MHz, $CDCl_3$) δ=8.40 (d, J=5.2 Hz, 1H), 8.07 (s, 1H), 7.74 (d, J=8.8 Hz, 2H), 7.53 (s, 1H), 7.45-7.32 (m, 6H), 7.00 (d, J=5.2 Hz, 1H), 6.96 (d, J=8.8 Hz, 2H), 6.83 (d, J=8.8 Hz, 2H), 4.39 (d, J=12.8 Hz, 1H), 4.15 (t, J=4.8 Hz, 2H), 4.06-4.00 (m, 3H), 3.81 (t, J=4.8 Hz, 2H), 3.57-3.52 (m, 4H), 3.39 (t, J=11.2 Hz, 2H), 3.16 (d, J=6.8 Hz, 2H), 2.59-2.54 (m, 4H), 2.36 (s, 3H), 2.11-2.08 (m, 1H), 1.72-

1.58 (m, 6H), 1.44-1.35 (m, 4H), 1.18 (t, J=7.6 Hz, 3H), 0.93 (t, J=7.2 Hz, 3H).
WX007 MS-ESI (m/z): 750.4 (M+1)$^+$
$^1$H NMR (400 MHz, $CDCl_3$) δ=8.33 (d, J=5.2 Hz, 1H), 8.24 (s, 1H), 7.74 (d, J=8.8 Hz, 2H), 7.53 (s, 1H), 7.44-7.31 (m, 6H), 6.99 (d, J=4.8 Hz, 1H), 6.95 (d, J=8.8 Hz, 2H), 6.82 (d, J=8.8 Hz, 2H), 4.37 (d, J=12.8 Hz, 1H), 4.14 (t, J=4.8 Hz, 2H), 4.05-3.99 (m, 3H), 3.80 (t, J=4.8 Hz, 2H), 3.56-3.49 (m, 4H), 3.38 (t, J=11.2 Hz, 2H), 3.15 (d, J=6.8 Hz, 2H), 2.59-2.52 (m, 4H), 2.34 (s, 3H), 2.09-2.04 (m, 1H), 1.71-1.57 (m, 6H), 1.44-1.36 (m, 4H), 1.16 (t, J=7.6 Hz, 3H), 0.93 (t, J=7.2 Hz, 3H).
Embodiment 5
WX008 or WX009 or WX010 or WX011
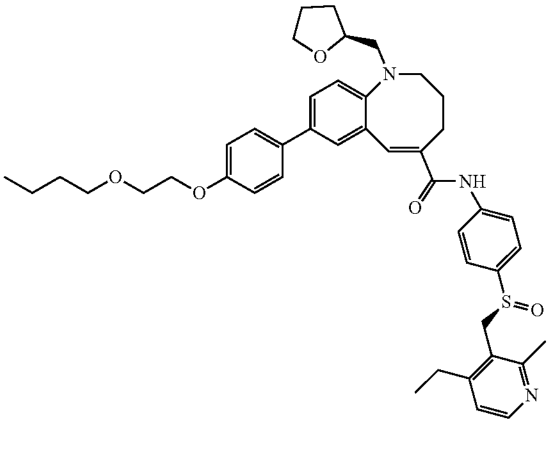
WX009 or WX008 or WX010 or WX011
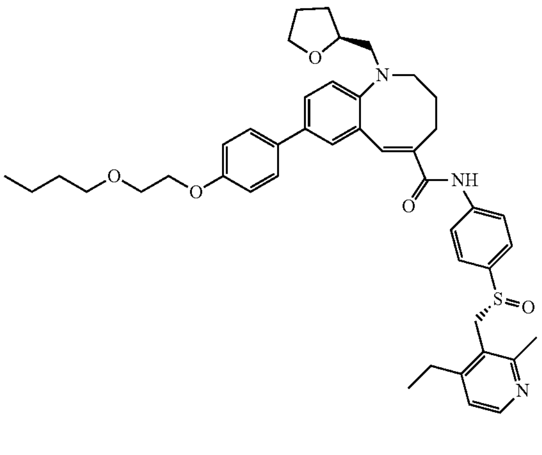
-continued
WX010 or WX011 or WX008 or WX009
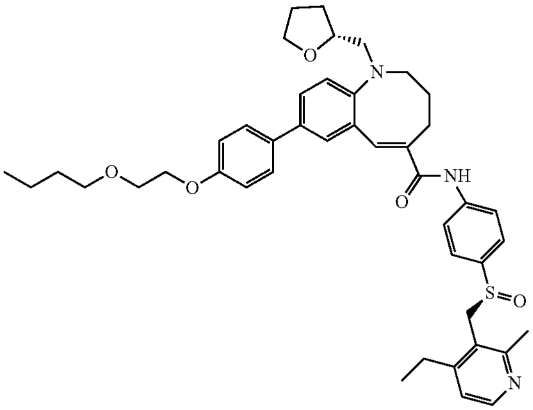
WX011 or WX010 or WX008 or WX009
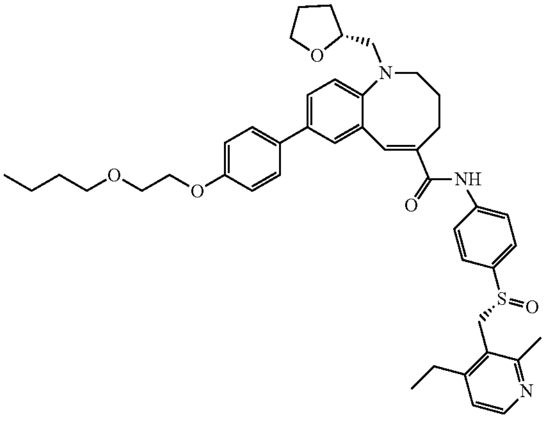
Synthetic Route:
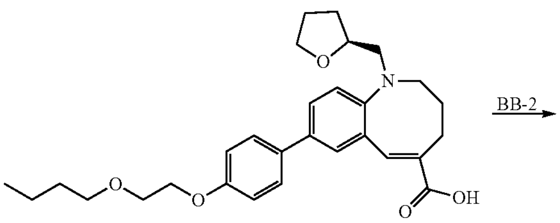
WX004-1 or WX005-1

-continued

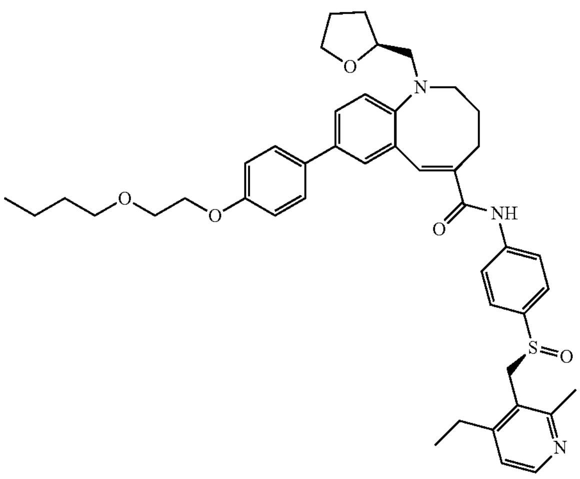

WX008 or WX009 or WX010 or WX011

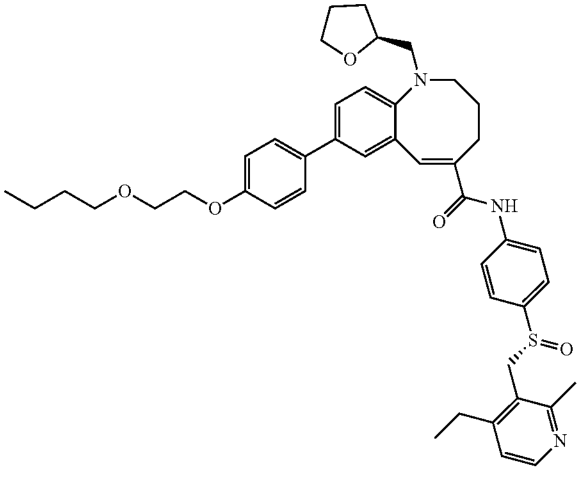

WX009 or WX008 or WX010 or WX011

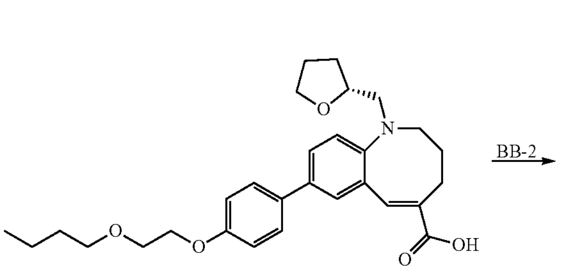

WX004-1 or WX005-1

-continued

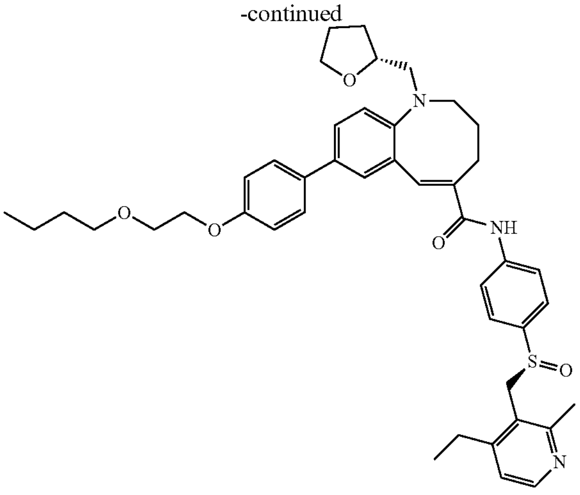

WX010 or WX011 or WX008 or WX009

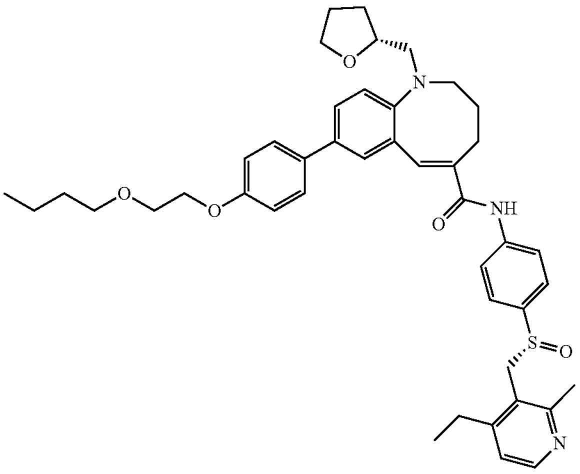

WX011 or WX010 or WX008 or WX009

Step 1: Synthesis of Compounds WX008 and WX009

At 60° C., EDCI (56 mg) and compound BB-2 (48 mg) were added to a solution of compound WX004-1 (70 mg) in pyridine (3 mL) to react for 4 hours, and the reaction solution was concentrated to remove the pyridine and then water (20 mL) was added thereto. The reaction solution was extracted with DCM/MeOH=20/1 (20 mL×2), and the organic phases were combined, washed with saturated brine (20 mL) and dried over anhydrous sodium sulfate. Then the organic phases were filtered, concentrated and the residue was purified by pre.TLC (DCM/MeOH=15/1) and then split by SFC to obtain compounds WX008 (retention time: 2.258 min) and WX009 (retention time: 3.404 min). SFC splitting condition: column type: Chiralpak AD-3 50*4.6 mm I.D., 3 m; mobile phase: A: $CO_2$ B: isopropanol (0.05% DEA);

gradient: 40% B; flow rate: 4 mL/min; column temperature: 35° C.; column pressure: 1500 psi.

WX008 MS-ESI (m/z): 736.4 $(M+1)^+$ $^1$H NMR (400 MHz, $CDCl_3$) δ=8.34 (d, J=4.8 Hz, 1H), 8.10 (s, 1H), 7.74 (d, J=8.8 Hz, 2H), 7.52 (s, 1H), 7.44-7.30 (m, 6H), 7.00 (d, J=5.2 Hz, 1H), 6.95 (d, J=8.8 Hz, 2H), 6.9. (d, J=9.2 Hz, 2H), 4.38 (d, J=12.8 Hz, 1H), 4.25-4.21 (m, 1H), 4.15 (t, J=4.8 Hz, 2H), 4.04 (d, J=13.2 Hz, 1H), 3.94 (q, J=7.6 Hz, 1H), 3.82-3.67 (m, 4H), 3.55 (t, J=6.4 Hz, 2H), 3.44-3.32 (m, 2H), 2.58-2.53 (m, 4H), 2.37 (s, 3H), 2.14-2.07 (m, 1H), 2.03-1.89 (m, 2H), 1.65-1.54 (m, 5H), 1.44-1.35 (m, 2H), 1.17 (t, J=7.6 Hz, 3H), 0.93 (t, J=7.2 Hz, 3H);

WX009 MS-ESI (m/z): 736.4 $(M+1)^+$ $^1$H NMR (400 MHz, $CDCl_3$) δ=8.34 (d, J=4.8 Hz, 1H), 8.06 (s, 1H), 7.74 (d, J=8.8 Hz, 2H), 7.53 (s, 1H), 7.44-7.31 (m, 6H), 7.00 (d, J=4.8 Hz, 1H), 6.95 (d, J=8.8 Hz, 2H), 6.92 (d, J=8.8 Hz, 2H), 4.39 (d, J=13.2 Hz, 1H), 4.26-4.20 (m, 1H), 4.15 (t, J=4.8 Hz, 2H), 4.04 (d, J=13.2 Hz, 1H), 3.94 (q, J=7.6 Hz, 1H), 3.82-3.70 (m, 4H), 3.55 (t, J=6.8 Hz, 2H), 3.44-3.32 (m, 2H), 2.58-2.53 (m, 4H), 2.38 (s, 3H), 2.14-2.07 (m, 1H), 2.03-1.89 (m, 2H), 1.72-1.55 (m, 5H), 1.44-1.33 (m, 2H), 1.17 (t, J=7.6 Hz, 3H), 0.93 (t, J=7.2 Hz, 3H).

Step 2: Synthesis of Compounds WX010 and WX011

At 60° C., EDCI (56 mg) and compound BB-2 (48 mg) were added to a solution of compound WX005-1 (70 mg) in pyridine (3 mL) to react for 1 hour, and the reaction solution was concentrated to remove the pyridine and water (20 mL) was added thereto. The reaction solution was extracted with DCM/MeOH=20/1 (20 mL×2), and the organic phases were combined, washed with saturated brine (20 mL) and dried over anhydrous sodium sulfate. Then the organic phases were filtered, concentrated and the residue was purified by pre.TLC (DCM/MeOH=15/1) and then split by SFC to obtain compounds WX010 (retention time: 3.214 min) and WX011 (retention time: 5.999 min).

SFC splitting condition: column type: ChiralpakAD-3 50*4.6 mm I.D., 3 m; mobile phase: A: $CO_2$ B: isopropanol (0.05% DEA); gradient: 40% B; flow rate: 4 mL/min; column temperature: 35° C.; column pressure: 1500 psi.

WX010 MS-ESI (m/z): 736.4 (M+1)+

$^1$H NMR (400 MHz, $CDCl_3$) δ=8.34 (d, J=5.2 Hz, 1H), 7.77-7.73 (m, 2H), 7.53 (s, 1H), 7.47-7.33 (m, 6H), 7.02-6.93 (m, 4H), 4.40 (d, J=13.2 Hz, 1H), 4.26-4.22 (m, 1H), 4.16 (t, J=4.8 Hz, 2H), 4.06 (d, J=12.8 Hz, 1H), 3.97-3.92 (m, 1H), 3.82-3.68 (m, 4H), 3.60-3.54 (m, 3H), 3.45-3.33 (m, 2H), 2.62-2.54 (m, 4H), 2.39 (s, 3H), 2.15-2.08 (m, 1H), 2.00-1.89 (m, 2H), 1.65-1.55 (m, 5H), 1.45-1.34 (m, 2H), 1.18 (t, J=7.6 Hz, 3H), 0.94 (t, J=7.2 Hz, 3H);

WX011 MS-ESI (m/z): 736.5 $(M+1)^+$ $^1$H NMR (400 MHz, $CDCl_3$) δ=8.34 (d, J=5.2 Hz, 1H), 7.91 (brs, 1H), 7.77-7.73 (m, 2H), 7.53 (s, 1H), 7.46-7.32 (m, 6H), 7.02-6.93 (m, 4H), 4.40 (d, J=13.2 Hz, 1H), 4.25-4.22 (m, 1H), 4.16 (t, J=4.8 Hz, 2H), 4.06 (d, J=13.2 Hz, 1H), 3.97-3.92 (m, 1H), 3.82-3.68 (m, 4H), 3.60-3.54 (m, 3H), 3.45-3.33 (m, 2H), 2.62-2.54 (m, 4H), 2.39 (s, 3H), 2.15-2.08 (m, 1H), 2.03-1.91 (m, 2H), 1.67-1.55 (m, 5H), 1.45-1.36 (m, 2H), 1.16 (t, J=7.6 Hz, 3H), 0.94 (t, J=7.2 Hz, 3H).

Embodiment 6

WX012 or WX013

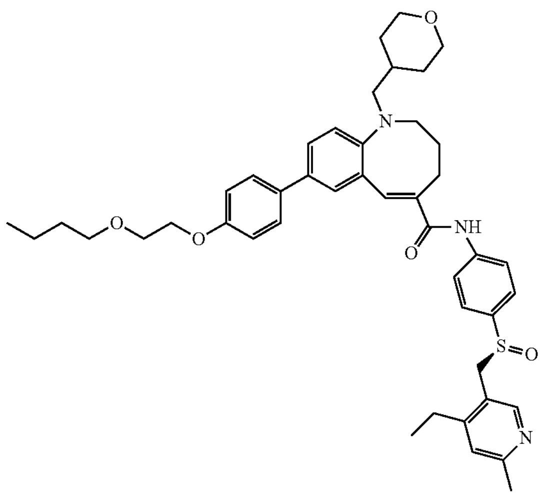

WX013 or WX012

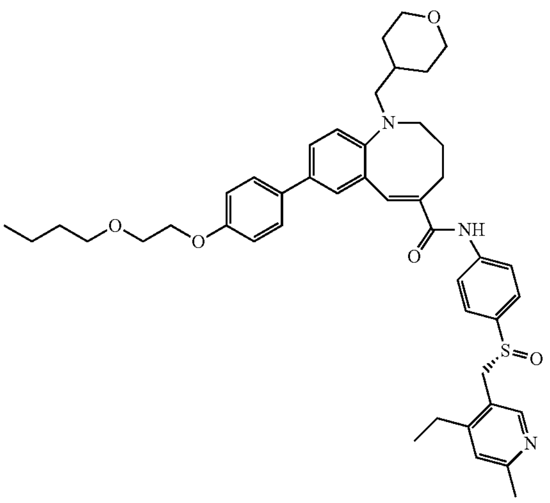

Synthetic Route:

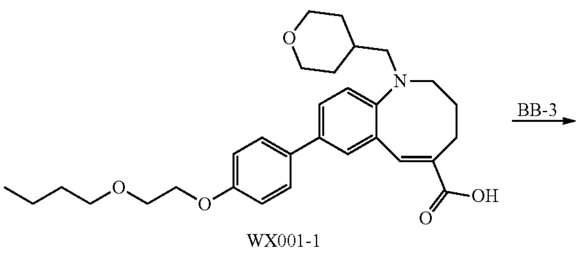

WX001-1

-continued

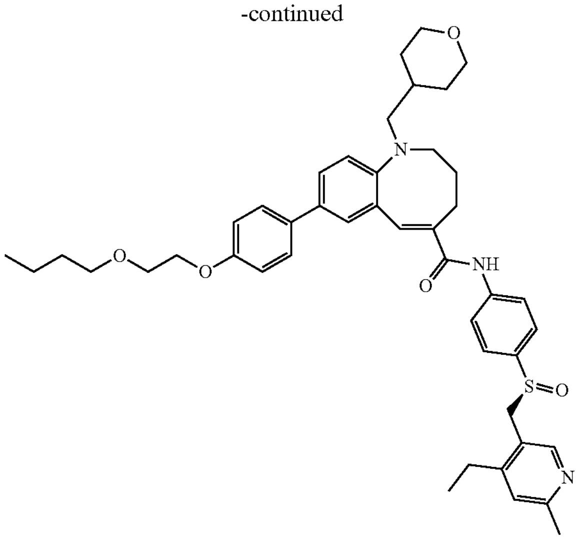

WX012 or WX013

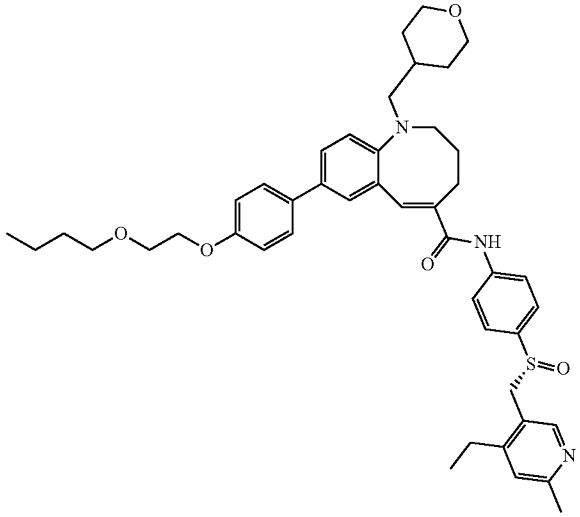

WX013 or WX012

At 25° C., EDCI (70 mg) was added to a solution of compounds BB-3 (50 mg) and WX001-1 (90 mg) in pyridine (2 mL), and the reaction was conducted at 60° C. for 2 hours. Water (5 mL) was added to the reaction solution and extracted with ethyl acetate (5 mL×3), and the organic phases were combined, washed with saturated brine (10 mL), dried over anhydrous sodium sulfate, and the organic phase was concentrated by rotary evaporation. The crude product was purified by prep-TLC ($SiO_2$, DCM:MeOH=20:1) then split by SFC to obtain compounds WX012 (retention time: 7.475 min) and WX013 (retention time: 9.823 min).

SFC splitting condition: column type: (S,S) Whelk-01 100×4.6 mm I.D., 5 m; mobile phase: A: $CO_2$ B: (20% acetonitrile/80% methanol) (0.05% diethylamine); gradient: 50% B; flow rate: 2.5 mL/min; column temperature: 40° C.

WX012: MS-ESI (m/z): 750.2 $(M+1)^+$ $^1$H NMR (400 MHz, $CDCl_3$) δ=7.87 ppm (s, 1H), 7.74 (d, J=8.80 Hz, 2H), 7.69 (s, 1H), 7.54 (s, 1H), 7.46 (d, J=8.40 Hz, 2H), 7.45-7.41 (m, 1H), 7.33-7.41 (m, 3H), 7.05-6.96 (m, 3H), 6.84 (d, J=8.80 Hz, 1H), 4.15 (dd, J=9.16, 4.14 Hz, 3H), 4.09-3.98 (m, 3H), 3.84-3.71 (m, 2H), 3.60-3.50 (m, 4H), 3.40 (br t, J=11.00 Hz, 2H), 3.17 (br d, J=6.80 Hz, 2H), 2.64 (dt, J=7.80 Hz, 4H), 2.52 (s, 3H), 2.10 (br s, 1H), 1.73 (br s, 2H), 1.63-1.57 (m, 4H), 1.50-1.37 (m, 4H), 1.23 (t, J=7.60 Hz, 3H), 0.94 (t, J=7.20 Hz, 3H);

WX013: MS-ESI (m/z): 750.4 $(M+1)^+$ $^1$H NMR (400 MHz, $CDCl_3$) δ=7.88 ppm (s, 1H), 7.74 (d, J=8.5 Hz, 2H), 7.70 (s, 1H), 7.54 (s, 1H), 7.49-7.45 (m, 2H), 7.43 (m, 1H), 7.39 (s, 1H), 7.38-7.34 (m, 2H), 7.03 (s, 1H), 6.98 (d, J=8.8 Hz, 2H), 6.84 (d, J=8.8 Hz, 1H), 4.19-4.12 (m, 3H), 4.08-3.98 (m, 3H), 3.84-3.79 (m, 2H), 3.58-3.51 (m, 4H), 3.40 (m, 2H), 3.17 (m, 2H), 2.63 (m, 4H), 2.51 (s, 3H), 2.16-2.04 (m, 1H), 1.74-1.68 (m, 4H), 1.61 (m, 2H), 1.49-1.36 (m, 4H), 1.23 (t, J=7.8 Hz, 3H), 0.94 (t, J=7.40 Hz, 3H).

Embodiment 7

WX014 or WX015 or WX016 or WX017

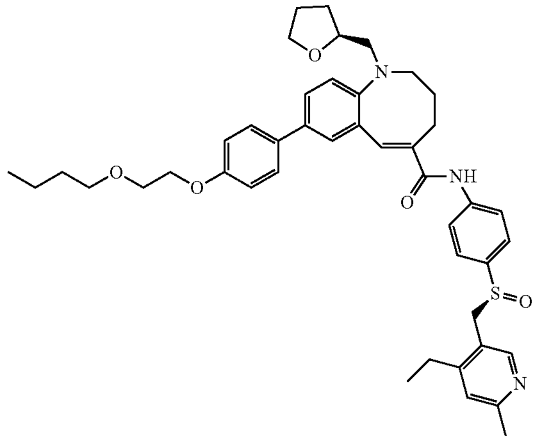

WX015 or WX014 or WX 016 or WX017

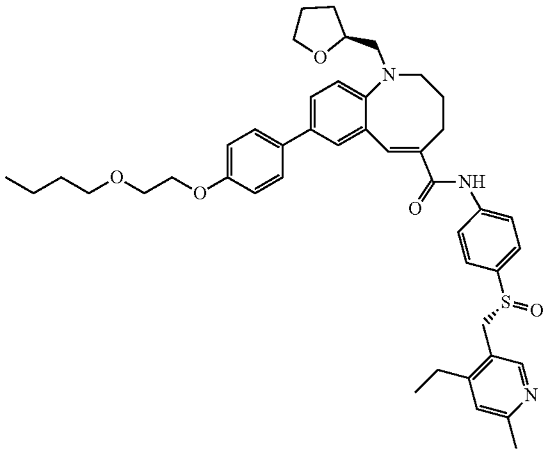

-continued
WX016 or WX017 or WX014 or WX015
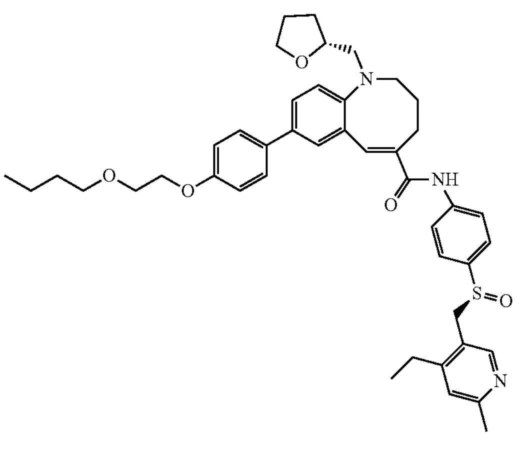
WX017 or WX016 or WX014 or WX015
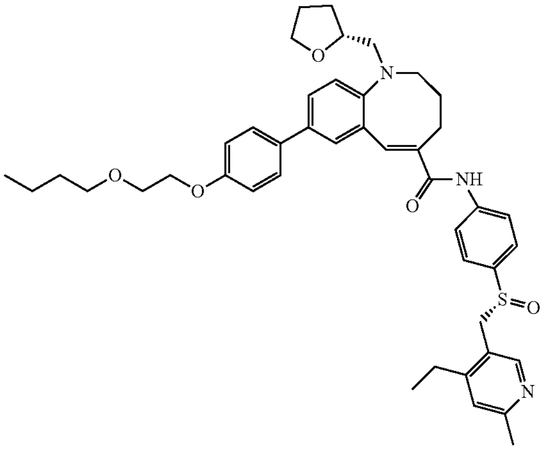
Synthetic Route:
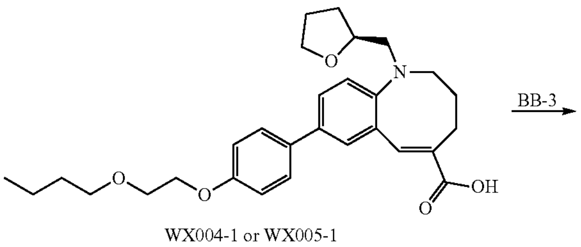
WX004-1 or WX005-1
-continued
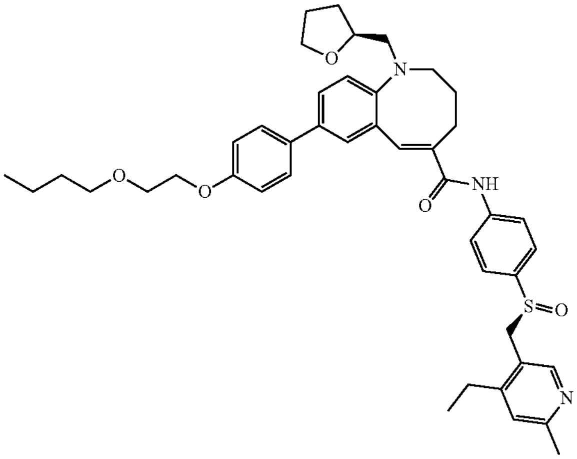
WX014 or WX015 or WX016 or WX017
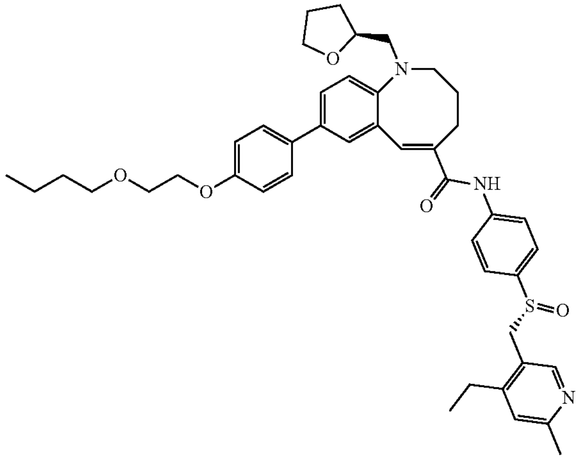
WX015 or WX014 or WX016 or WX017
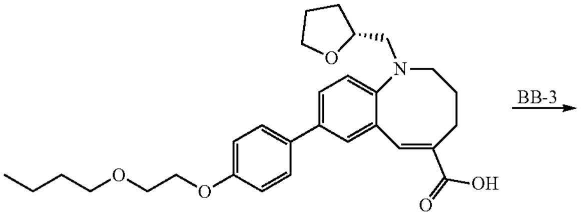
WX005-1 or WX004-1
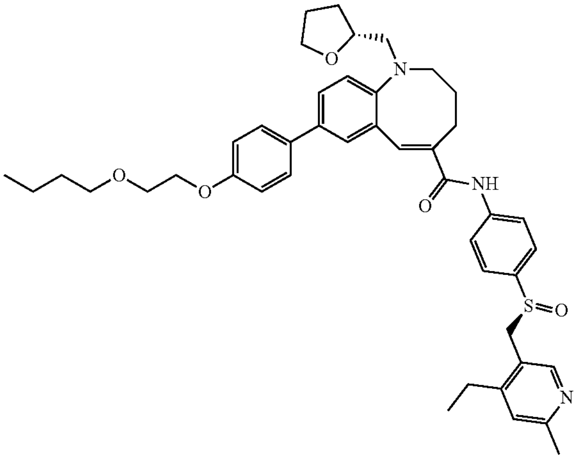
WX016 or WX017 or WX014 or WX015

-continued

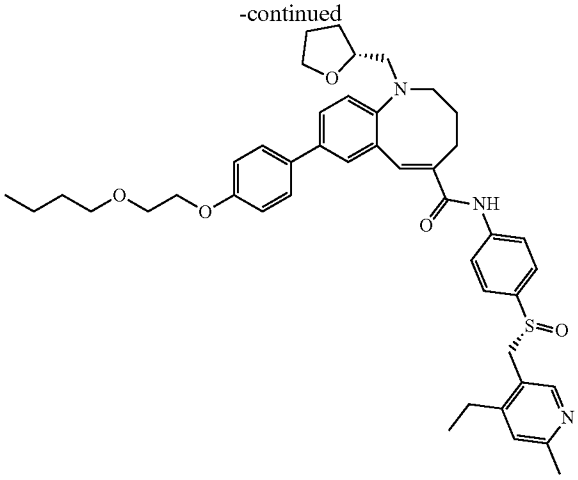

WX017 or WX016 or WX014 or WX015

Step 1: Synthesis of Compounds WX014 and WX015

At 25° C., EDCI (70 mg) was added to a solution of compounds BB-3 (50 mg) and WX004-1 (87 mg) in pyridine (2 mL), and the reaction was conducted at 60° C. for 2 hours. Water (5 mL) was added to the reaction solution and extracted with ethyl acetate (5 mL×3), and the organic phases were combined and washed with saturated brine (10 mL), dried over anhydrous sodium sulfate, and the organic phase was concentrated by rotary evaporation. The crude product was purified by prep-TLC ($SiO_2$, DCM:MeOH=20:1) then split by SFC to obtain compounds WX014 (retention time: 7.236 min) and WX015 (retention time: 9.585 min).

SFC splitting condition: column type: (S,S) Whelk-01 100×4.6 mm I.D., 5 m; mobile phase: A: $CO_2$ B: (20% acetonitrile/80% methanol) (0.05% diethylamine); gradient: 50% B; flow rate: 2.5 mL/min; column temperature: 40° C.; column pressure: 100 bar.

WX014: MS-ESI (m/z): 736.3 $(M+1)^+$ $^1$H NMR (400 MHz, $CDCl_3$) δ=7.98 ppm (s, 1H), 7.76-7.71 (m, 3H), 7.53 (s, 1H), 7.47-7.32 (m, 6H), 7.02 (s, 1H), 7.00-6.90 (m, 3H), 4.27-4.13 (m, 4H), 4.07-3.91 (m, 2H), 3.84-3.67 (m, 5H), 3.60-3.52 (m, 3H), 3.52-3.32 (m, 2H), 2.66-2.56 (m, 3H), 2.51 (s, 3H), 2.15-2.07 (m, 1H), 2.06-1.88 (m, 2H), 1.66-1.55 (m, 5H), 1.40 (m, 2H), 1.22 (t, J=7.4 Hz, 3H), 0.94 (t, J=7.4 Hz, 3H);

WX015: MS-ESI (m/z): 736.4 $(M+1)^+$ $^1$H NMR (400 MHz, $CDCl_3$) δ=7.94 ppm (br s, 1H), 7.74 (m, 3H), 7.53 (s, 1H), 7.49-7.32 (m, 6H), 7.07-6.92 (m, 4H), 4.24 (br s, 1H), 4.20-4.12 (m, 3H), 4.11-3.99 (m, 1H), 3.99-3.86 (m, 1H), 3.87-3.77 (m, 3H), 3.76-3.67 (m, 1H), 3.64-3.49 (m, 3H), 3.48-3.33 (m, 2H), 2.72-2.56 (m, 4H), 2.56-2.48 (m, 3H), 2.12 (br s, 1H), 2.04-1.89 (m, 2H), 1.62 (m, 5H), 1.46-1.36 (m, 2H), 1.22 (m, J=7.4 Hz, 3H), 0.94 (m, J=7.4 Hz, 3H).

Step 2: Synthesis of Compounds WX016 and WX017

At 25° C., EDCI (70 mg) was added to a solution of compounds BB-3 (50 mg) and WX005-1 (87 mg) in pyridine (2 mL), and the reaction was conducted at 60° C. for 2 hours. Water (5 mL) was added to the reaction solution and extracted with ethyl acetate (5 mL×3), and the organic phases were combined and washed with saturated brine (10 mL) and dried over anhydrous sodium sulfate. Then the organic phase was concentrated by rotary evaporation, and the crude product was purified by prep-TLC ($SiO_2$, DCM:MeOH=20:1) then split by SFC to obtain compounds WX016 (retention time: 6.733 min) and WX017 (retention time: 8.815 min).

SFC splitting condition: column type: (S,S) Whelk-01 100×4.6 mm I.D., 5 m; mobile phase: A: $CO_2$ B: (20% acetonitrile/80% methanol) (0.05% diethylamine) gradient: 50% B; flow rate: 2.5 mL/min; column temperature: 40° C.; column pressure: 100 bar.

WX016: MS-ESI (m/z): 736.3 $(M+1)^+$ $^1$H NMR (400 MHz, $CDCl_3$) δ=7.93 ppm (br s, 1H), 7.78-7.69 (m, 3H), 7.55 (s, 1H), 7.48-7.33 (m, 6H), 7.04 (s, 1H), 7.00-6.92 (m, 3H), 4.24 (br s, 1H), 4.19-4.12 (m, 3H), 4.11-4.02 (m, 1H), 4.02-3.89 (m, 1H), 3.84-3.68 (m, 4H), 3.56 (m, 3H), 3.52-3.33 (m, 2H), 2.68-2.57 (m, 4H), 2.53 (s, 3H), 2.16-2.08 (m, 1H), 2.05-1.88 (m, 2H), 1.65-1.57 (m, 5H), 1.40 (m, 2H), 1.23 (t, J=7.4 Hz, 3H), 0.94 (t, J=7.40 Hz, 3H);

WX017: MS-ESI (m/z): 736.3 $(M+1)^+$ $^1$H NMR (400 MHz, $CDCl_3$) δ=8.00 ppm (s, 1H), 7.77-7.70 (m, 3H), 7.53 (s, 1H), 7.47-7.32 (m, 6H), 7.03-6.91 (m, 4H), 4.28-4.19 (m, 1H), 4.18-4.12 (m, 3H), 4.08-3.99 (m, 1H), 3.99-3.89 (m, 1H), 3.84-3.67 (m, 4H), 3.60-3.52 (m, 3H), 3.46-3.32 (m, 2H), 2.66-2.56 (m, 4H), 2.51 (s, 3H), 2.16-2.05 (m, 1H), 2.04-1.88 (m, 2H), 1.66-1.56 (m, 5H), 1.40 (m, 2H), 1.22 (t, J=7.4 Hz, 3H), 0.94 (t, J=7.40 Hz, 3H).

Embodiment 8

WX018 or WX019

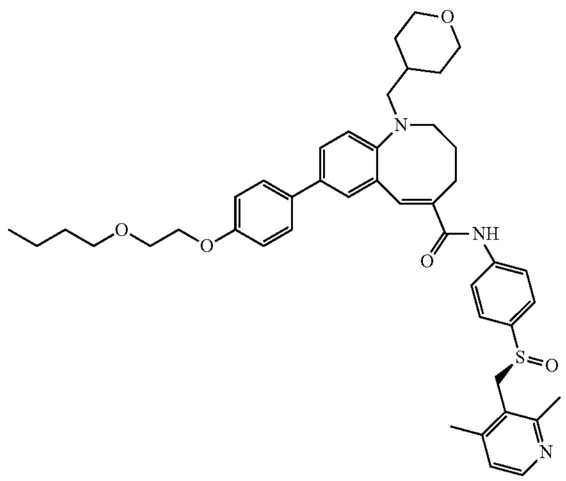

-continued

WX019 or WX018

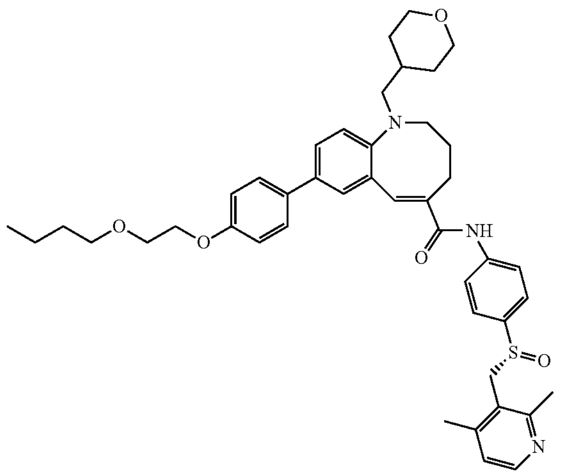

Synthetic Route:

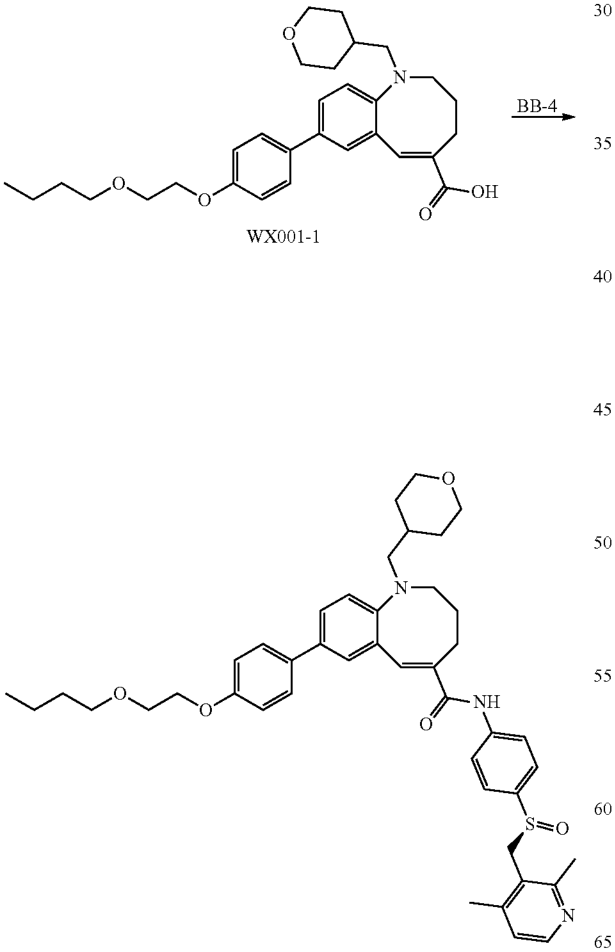

WX001-1

WX018 or WX019

-continued

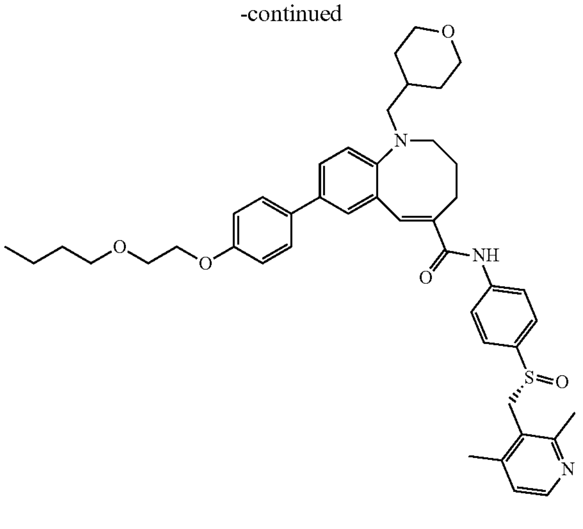

WX019 or WX018

At 25° C., EDCI (44 mg) was added to a solution of compounds WX001-1 (57 mg) and BB-4 (30 mg) in pyridine (3 mL), and the whole mixture was stirred at 60° C. for 4 hours. 50 mL of ethyl acetate was added to the reaction solution, then the reaction solution was concentrated under reduced pressure and separated by prep-TLC ($SiO_2$, DCM: MeOH=12:1) then split by SFC to obtain compounds WX018 (retention time: 9.606 min) and WX019 (retention time: 11.154 min).

SFC splitting condition: column type: ChiralPak AD-3 150×4.6 mm I.D., 3 m; mobile phase: A: $CO_2$ B: IPA (0.05% DEA); gradient: 40% B; flow rate: 2.5 mL/min; column temperature: 40° C.; column pressure: 100 bar.

WX018: MS-ESI (m/z): 736.5 $(M+1)^+$ $^1H$ NMR (400 MHz, $CDCl_3$) δ ppm 0.94 (t, J=7.4 Hz, 3H), 1.34-1.46 (m, 4H), 1.59-1.66 (m, 4H), 1.71 (br d, J=12.0 Hz, 2H), 2.10 (m, 1H), 2.21 (s, 3H), 2.39 (s, 3H), 2.55-2.66 (m, 2H), 3.17 (br d, J=6.8 Hz, 2H), 3.40 (br t, J=11.0 Hz, 2H), 3.47-3.61 (m, 4H), 3.78-3.88 (m, 2H), 3.99-4.11 (m, 3H), 4.16 (t, J=4.8 Hz, 2H), 4.39 (d, J=12.8 Hz, 1H), 6.85 (d, J=8.8 Hz, 1H), 6.90-7.02 (m, 3H), 7.34 (d, J=2.0 Hz, 1H), 7.39-7.49 (m, 5H), 7.53 (s, 1H), 7.75 (d, J=8.4 Hz, 2H), 7.80 (s, 1H), 8.30 (d, J=5.2 Hz, 1H).

WX019: MS-ESI (m/z): 736.5 $(M+1)^+$ $^1H$ NMR (400 MHz, $CDCl_3$) δ ppm 0.94 (t, J=7.4 Hz, 3H), 1.35-1.50 (m, 4H), 1.59-1.66 (m, 4H), 1.71 (br d, J=13.2 Hz, 2H), 2.10 (br s, 1H), 2.21 (s, 3H), 2.39 (s, 3H), 2.54-2.64 (m, 2H), 3.17 (br d, J=6.4 Hz, 2H), 3.40 (br t, J=11.0 Hz, 2H), 3.48-3.61 (m, 4H), 3.78-3.86 (m, 2H), 3.98-4.10 (m, 3H), 4.16 (t, J=4.8 Hz, 2H), 4.39 (d, J=13.2 Hz, 1H), 6.85 (d, J=8.4 Hz, 1H), 6.91-7.01 (m, 3H), 7.34 (d, J=2.4 Hz, 1H), 7.38-7.49 (m, 5H), 7.53 (s, 1H), 7.75 (d, J=8.8 Hz, 2H), 7.81 (s, 1H), 8.30 (d, J=4.8 Hz, 1H).

Embodiment 9

WX020 or WX021

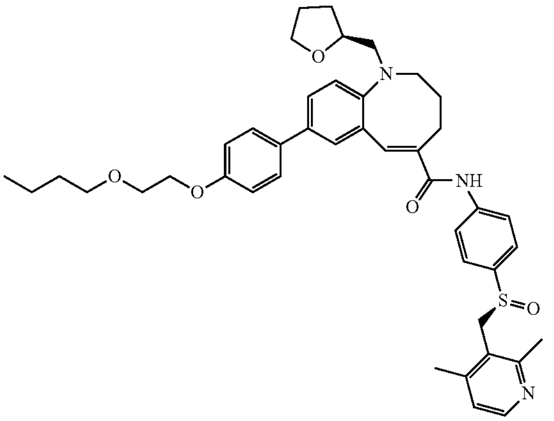

WX021 or WX020

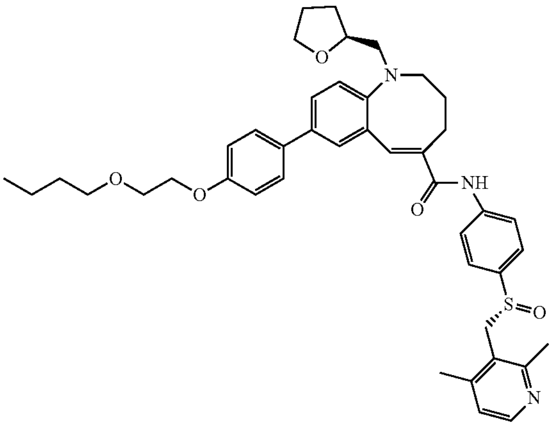

Synthetic Route:

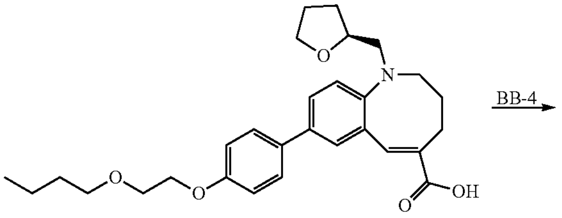

WX004-1 or WX005-1

-continued

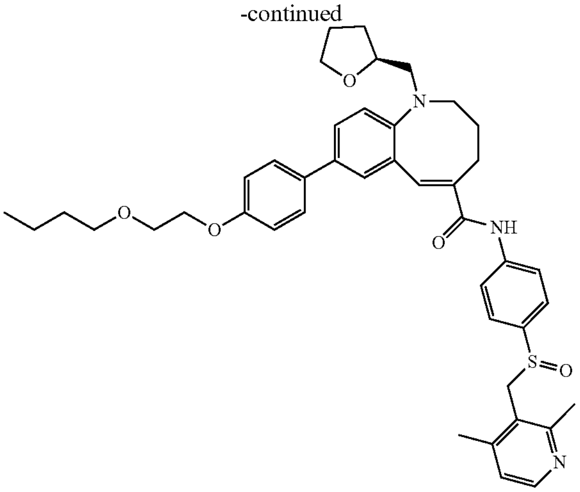

WX020 or WX021

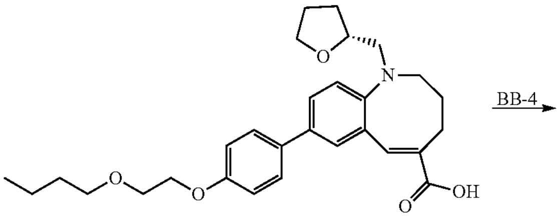

WX005-1 or WX004-1

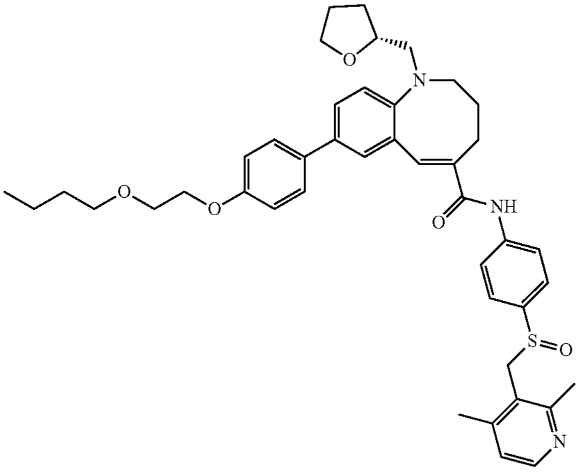

WX021 or WX020

Step 1: Synthesis of Compound WX020

At 25° C., EDCI (44 mg) was added to a solution of compounds WX004-1 (55 mg) and BB-4 (30 mg) in pyridine (3 mL), then the whole mixture was stirred at 60° C. for 4 hours. 50 mL of ethyl acetate was added to the reaction solution, then the reaction solution was concentrated under reduced pressure and directly separated by prep-HPLC (basic) to obtain compound WX020. MS-ESI (m/z): 722.5 $(M+1)^+$.

$^1$H NMR (400 MHz, $CDCl_3$) δ ppm 0.94 (t, J=7.4 Hz, 3H), 1.32-1.47 (m, 2H), 1.55-1.66 (m, 6H), 1.92-1.99 (m, 2H), 2.05-2.17 (m, 1H), 2.20 (s, 3H), 2.41 (s, 3H), 2.60 (br s, 2H), 3.29-3.48 (m, 2H), 3.56 (t, J=6.2 Hz, 2H), 3.67-3.84 (m, 4H), 3.94 (q, J=7.5 Hz, 1H), 4.06 (d, J=12.8 Hz, 1H), 4.16 (t, J=4.8 Hz, 2H), 4.23 (m, 1H), 4.39 (d, J=12.8 Hz, 1H), 6.90-7.00 (m, 4H), 7.33 (d, J=2.0 Hz, 1H), 7.37-7.49 (m, 5H), 7.54 (s, 1H), 7.76 (d, J=8.8 Hz, 2H), 7.87 (s, 1H), 8.30 (d, J=5.2 Hz, 1H).

Step 2: Synthesis of Compound WX021

At 25° C., EDCI (44 mg) was added to a solution of compounds WX005-1 (55 mg) and BB-4 (30 mg) in pyridine (3 mL), then the whole mixture was stirred at 60° C. for 4 hours. 50 mL of ethyl acetate was added to the reaction solution, then the reaction solution was concentrated under reduced pressure and then separated by prep-HPLC (basic) to obtain compound WX021. MS-ESI (m/z): 722.5 $(M+1)^+$.

$^1H$ NMR (400 MHz, $CDCl_3$) δ ppm 0.94 (t, J=7.4 Hz, 3H), 1.40 (m, 2H), 1.53-1.72 (m, 6H), 1.88-2.02 (m, 2H), 2.07-2.16 (m, 1H), 2.19 (s, 3H), 2.40 (s, 3H), 2.53-2.64 (m, 2H), 3.31-3.46 (m, 2H), 3.56 (t, J=6.6 Hz, 2H), 3.66-3.84 (m, 4H), 3.90-3.98 (m, 1H), 4.06 (d, J=13.2 Hz, 1H), 4.12-4.19 (m, 2H), 4.19-4.28 (m, 1H), 4.38 (d, J=13.2 Hz, 1H), 6.88-7.00 (m, 4H), 7.32 (d, J=2.0 Hz, 1H), 7.36-7.48 (m, 5H), 7.53 (s, 1H), 7.75 (d, J=8.4 Hz, 2H), 7.91 (br s, 1H), 8.30 (d, J=4.8 Hz, 1H).

Embodiment 10

WX022

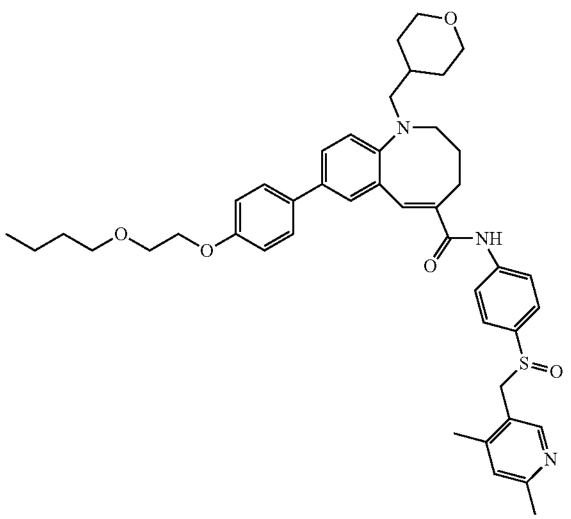

Synthetic Route:

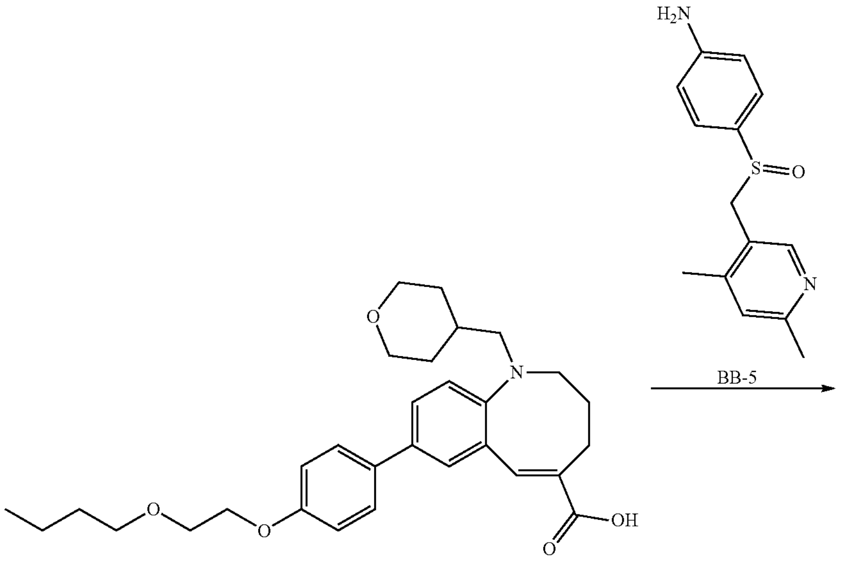

WX001-1

-continued

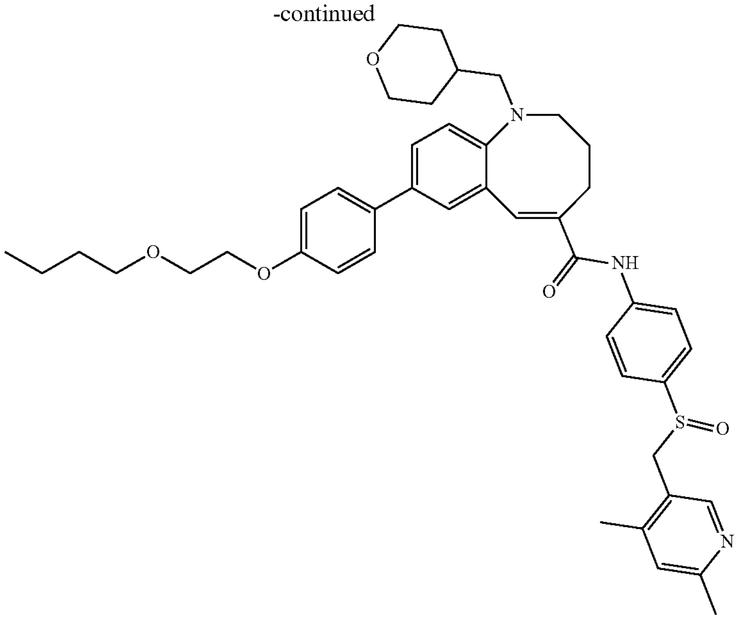

WX022

At 25° C., EDCI (59 mg) was added to a solution of compounds WX001-1 (76 mg) and BB-5 (40 mg) in pyridine (3 mL), and then the whole mixture was stirred at 60° C. under nitrogen protection for 4 hours. 50 mL of ethyl acetate was added to the reaction solution, then the reaction solution was concentrated under reduced pressure and separated by prep-TLC ($SiO_2$, DCM:MeOH=12:1) to obtain compound WX022. MS-ESI (m/z): 736.5 (M+1)+.

$^1$H NMR (400 MHz, $CDCl_3$) δ ppm 0.94 (t, J=7.4 Hz, 3H), 1.35-1.51 (m, 4H), 1.55-1.65 (m, 4H), 1.71 (br d, J=11.6 Hz, 2H), 2.10 (br s, 1H), 2.27 (s, 3H), 2.50 (s, 3H), 2.56-2.65 (m, 2H), 3.17 (br d, J=7.2 Hz, 2H), 3.40 (br t, J=11.2 Hz, 2H), 3.51-3.59 (m, 4H), 3.76-3.84 (m, 2H), 3.97-4.06 (m, 2H), 4.06-4.13 (m, 2H), 4.13-4.19 (m, 2H), 6.85 (d, J=8.8 Hz, 1H), 6.98 (d, J=8.8 Hz, 3H), 7.33-7.49 (m, 6H), 7.54 (s, 1H), 7.69-7.77 (m, 3H), 7.85 (s, 1H).

Embodiment 11

WX023 or WX024

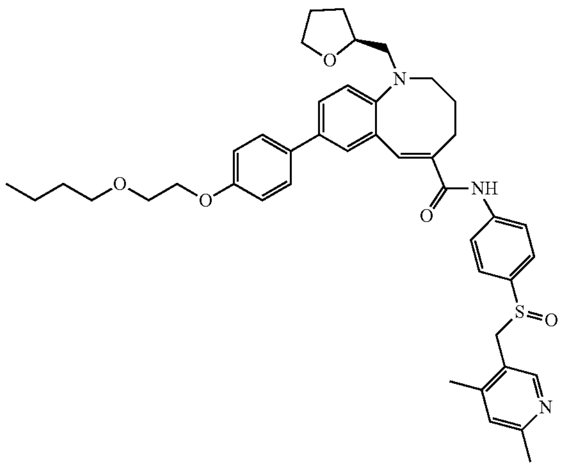

-continued

WX024 or WX023

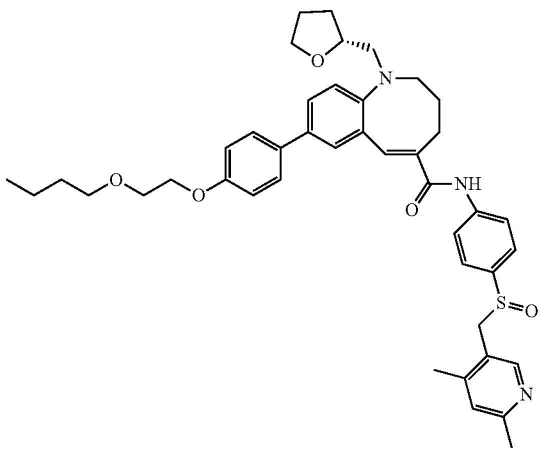

Synthetic Route:

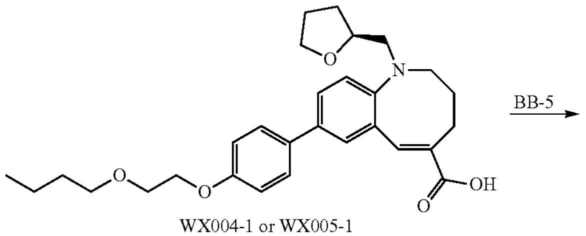

WX004-1 or WX005-1

-continued

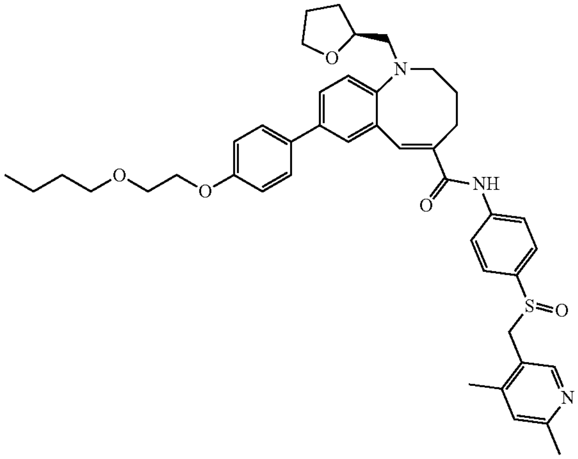

WX023 or WX024

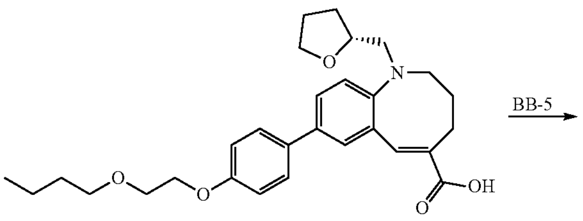

WX005-1 or WX004-1

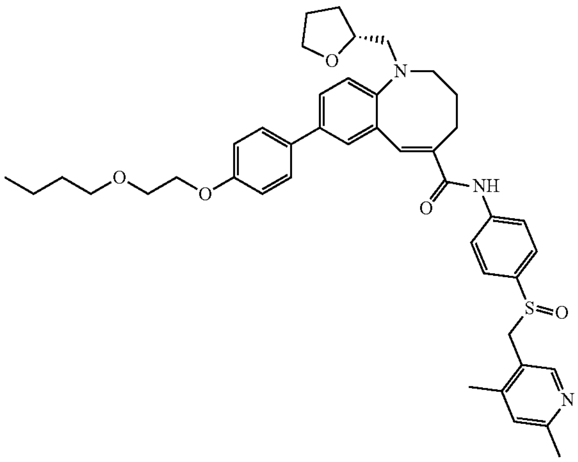

WX024 or WX023

Step 1: Synthesis of Compound WX023

At 25° C., EDCI (29 mg) was added to a solution of compounds WX004-1 (37 mg) and BB-5 (20 mg) in pyridine (3 mL), then the whole mixture was stirred at 60° C. under nitrogen protection for 3 hours. 50 mL of ethyl acetate was added to the reaction solution, then the reaction solution was concentrated under reduced pressure and separated by prep-TLC ($SiO_2$, DCM:MeOH=12:1) to obtain compound WX023. MS-ESI (m/z): 722.5 (M+1)+.

$^1$H NMR (400 MHz, $CDCl_3$) δ ppm 0.94 (t, J=7.4 Hz, 3H), 1.36-1.45 (m, 2H), 1.60-1.67 (m, 4H), 1.88-2.01 (m, 2H), 2.05-2.16 (m, 1H), 2.27 (s, 3H), 2.52 (s, 3H), 2.56-2.65 (m, 2H), 3.33-3.47 (m, 2H), 3.52-3.63 (m, 3H), 3.67-3.84 (m, 5H), 3.91-3.98 (m, 1H), 4.09 (s, 2H), 4.16 (t, J=4.89 Hz, 2H), 4.20-4.30 (m, 1H), 6.92-7.03 (m, 4H), 7.34-7.43 (m, 4H), 7.46 (d, J=8.4 Hz, 2H), 7.53-7.57 (m, 1H), 7.69-7.78 (m, 3H), 7.82-7.90 (m, 1H).

Step 2: Synthesis of Compound WX024

At 25° C., EDCI (29 mg) was added to a solution of compounds WX005-1 (37 mg) and BB-5 (20 mg) in pyridine (3 mL), and then the whole mixture was stirred at 60° C. under nitrogen protection for 4 hours. 50 mL of ethyl acetate was added to the reaction solution, then the reaction solution was concentrated under reduced pressure and separated by prep-TLC ($SiO_2$, DCM:MeOH=12:1) to obtain compound WX024. MS-ESI (m/z): 722.5 (M+1)+.

$^1$H NMR (400 MHz, $CDCl_3$) δ ppm 0.94 (t, J=7.4 Hz, 3H), 1.32-1.46 (m, 2H), 1.55-1.60 (m, 3H), 1.87-2.02 (m, 3H), 1.90-2.00 (m, 2H), 2.06-2.17 (m, 1H), 2.25 (s, 3H), 2.50 (s, 3H), 2.61 (br s, 2H), 3.32-3.47 (m, 2H), 3.51-3.63 (m, 2H), 3.67-3.84 (m, 4H), 3.90-3.98 (m, 1H), 4.09 (d, J=8.4 Hz, 2H), 4.12-4.18 (m, 2H), 4.20-4.28 (m, 1H), 6.90-7.01 (m, 4H), 7.32-7.43 (m, 4H), 7.45 (d, J=8.4 Hz, 2H), 7.54 (s, 1H), 7.69-7.77 (m, 3H), 7.88 (s, 1H).

Embodiment 12

WX025

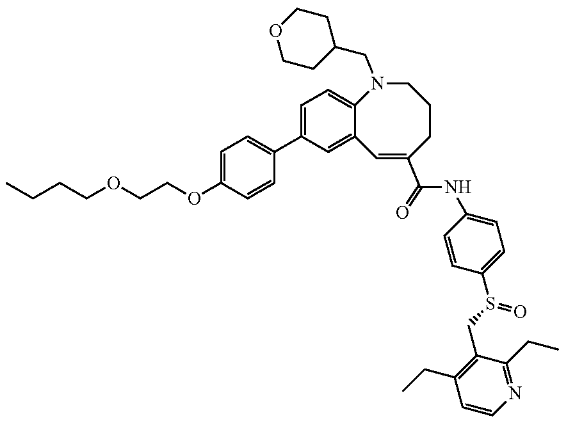

Synthetic Route:

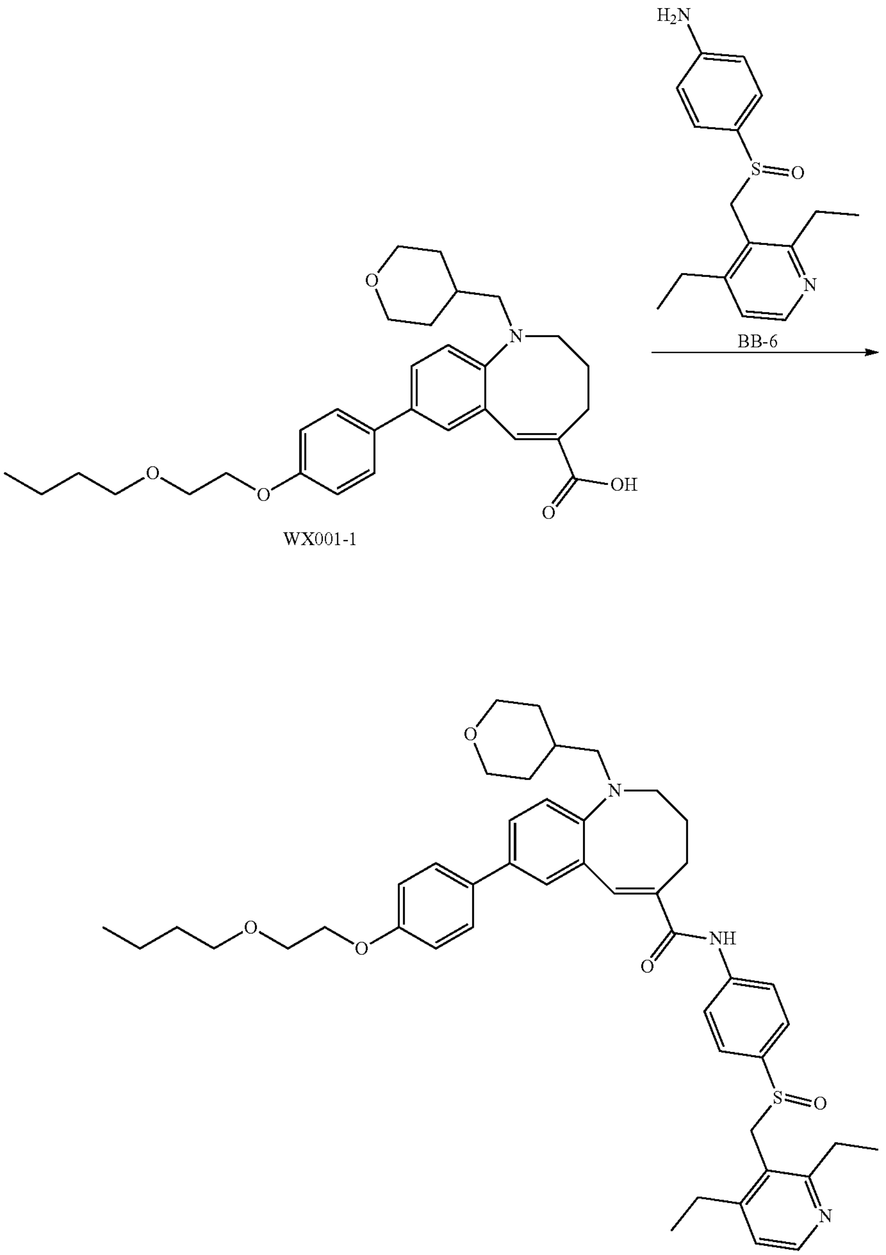

WX001-1

WX025

At 25° C., compounds WX001-1 (150 mg) and BB-6 (88 mg) were dissolved in pyridine (3 mL), then EDCI (117 mg) was added thereto, then the solution was stirred at 60° C. for 3 hours. The solution was concentrated directly and separated by prep-TLC. Compound WX025 was obtain. MS-ESI (m/z): 764.6 (M+1)+.

$^1H$ NMR (400 MHz, $CDCl_3$) δ=8.42 ppm (d, J=5.2 Hz, 1H), 7.83 (s, 1H), 7.74 (d, J=8.8 Hz, 2H), 7.53 (s, 1H), 7.38-7.49 (m, 5H), 7.35 (d, J=2 Hz, 1H), 6.95-7.04 (m, 3H), 6.85 (d, J=8.8 Hz, 1H), 4.41 (d, J=13.2 Hz, 1H), 4.16 (t, J=4.8 Hz, 2H), 3.99-4.10 (m, 3H), 3.78-3.84 (m, 2H), 3.49-3.59 (m, 4H), 3.40 (br t, J=10.8 Hz, 2H), 3.17 (br d, J=6.4 Hz, 2H), 2.70 (q, J=7.6 Hz, 2H), 2.51-2.59 (m, 2H), 2.02-2.16 (m, 1H), 1.70 (br d, J=12.4 Hz, 2H), 1.56-1.65 (m, 6H), 1.35-1.47 (m, 4H), 1.22-1.29 (m, 3H), 1.18 (t, J=7.6 Hz, 3H), 0.94 (t, J=7.6 Hz, 3H).

Biological Data:

Experimental Embodiment 1: CCR2/CCR5 In Vitro Test

Experimental Objectives:

The inhibitory effects of the compounds on CCR2 and CCR5 receptors were evaluated by detecting intracellular calcium signaling changes by FLIPR Calcium assay, using the $IC_{50}$ values of the compounds as indicators.

Experimental Materials:

1. Cell lines: The cells were seeded and incubated overnight at 37° C. in a 5% $CO_2$ incubator CCR2/CCR5 density: 1 M (20 k/well)

| Target | Clone# | Passage# | Host |
|---|---|---|---|
| CCR2 | C7 | P6 | HEK293 |
| CCR5 | C13 | P4 | HEK293 |

2. Reagent: Fluo-4 Direct, (Invitrogen, Cat #F10471)

3. Device equipment:

Polylysine-coated 384 cell plate (Greiner #781946)

384-well compound plate (Greiner #781280)

FLIPR, molecular devices

ECHO, Labcyte

4. Compounds:

The compound was prepared by dissolving in DMSO to a 10 mM solution, and the compound solution was placed in a nitrogen chamber.

| Compound ID | Purity | Amount of compounds_mg |
|---|---|---|
| Cenicriviroc | 97.00 | 1.15 |

Agonist Reference Compounds:

| | | | |
|---|---|---|---|
| MCP-1 | Sigma | SRP3109 | Stock solution: 10 μm aqueous solution |
| RANTES | Sigma | SRP3269 | Stock solution: 10 μm aqueous solution |

Experimental Procedures and Methods:

Preparation of probenecid in FLIPR assay buffer: 1 mL of FLIPR assay buffer was added to 77 mg of probenecid to make a 250 mM solution. The solution was prepared every day to keep fresh.

2× (8 μM) Fluo-4 Direct™ loading buffer (10 mL of each)

A bottle of Fluo-4 Direct™ crystals (F10471) was thawed 10 mL of FLIPR assay buffer was added to the sample bottle.

0.2 mL of probenecid was added to each 10 mL of Fluo-Direct. The final measured concentration was 2.5 mM The solution was rotated, then left for >5 minutes (protected from light)

The solution was prepared every day to keep fresh.

Experimental Procedures:

a) Agonist Compound Preparation:

MCP-1 was diluted in FLIPR assay buffer 1:2 for 10 spots, starting at 0.5 μM (eventually to 100 nM). RANTES was diluted in FLIPR assay buffer 1:3 for 10 spots, starting at 0.5 μM (eventually to 100 nM). 20 μL of serially diluted compound buffer was added to each well of the DRC plate.

b) Antagonist Compound Preparation: Antagonist Reference Compounds

The standard compound was diluted in DMSO 1:3 for 11 points, starting at 1 mM.

The test compound was diluted in DMSO 1:3 for 11 spots, starting at 2 mM. 250 nL of compound solution was transferred to cell plates using Echo (Greiner #781946)

c) The cell plate was taken from the incubator and 20 μL of 2× Fluo-4 Direct no wash loading buffer was gently dispensed into a 384-well cell culture plate using a pipette. The volume in the final cell plate was 40 μL d) Incubation was conducted at 37° C. 5% $CO_2$ for 50 minutes, at room temperature for 10 minutes e) The cell plate was taken from the incubator and placed in the FLIPR. The composite plate and pipette tip box were placed in the FLIPR f) For DRC plates:

1) The program on FLIPRTETRA was run

2) Fluorescent signals were read 3) 10 μL of compound was transferred from DRC plate to cell plate 4) Fluorescent signals were read 5) The "Max-Min" was calculated from Read 90 to the maximum allowed. EC80 values for each cell line were calculated using FLIPR 6) Agonist reference compound at 5 times EC80 concentration was prepared g) For composite plates (1-addition):

1) The program on FLIPRTETRA was run 2) 10 μL of agonist reference compound at 5 times EC80 concentration was transferred from the composite plate to the cell plate.

3) Fluorescence signals were read.

4) The "Max-Min" was calculated from Read 90 to the maximum allowed h) Data was analyzed by using Prism, the $IC_{50}$ values of the compounds were calculated.

The experimental results are shown in Table 1:

TABLE 1

FLIPR assay $IC_{50}$ (nM) test results

| Compound number | CCR2 | CCR5 |
|---|---|---|
| WX001 | 17.64 | 4.36 |
| WX002 | 19.54 | 7.47 |
| WX003 | 16.46 | 11.65 |
| WX004 | 19.37 | 6.47 |
| WX005 | 20.88 | 8.90 |
| WX006 | 15.92 | — |
| WX007 | 1.96 | 5.74 |
| WX008 | 15.18 | — |
| WX009 | 1.84 | 4.64 |
| WX010 | 13.70 | — |
| WX011 | 1.15 | 3.79 |
| WX012 | 1.50 | 8.40 |
| WX013 | 19.93 | — |
| WX014 | 1.39 | 12.13 |
| WX015 | 21.36 | — |
| WX016 | 1.75 | 16.42 |
| WX017 | 34.00 | — |
| WX018 | — | 15.25 |
| WX019 | — | 3.90 |
| WX020 | — | 5.61 |
| WX021 | — | 5.89 |
| WX022 | — | 13.56 |
| WX023 | — | 9.71 |
| WX024 | — | 11.28 |
| WX025 | 2.26 | 4.26 |

"—" means not detected

Conclusion: The compounds of the present disclosure have significant antagonistic effects on CCR2 and CCR5 receptors.

Experimental Embodiment 2 Inhibition of Human Liver Microsomal Cytochrome P450 Isozymes (CYP1A2, CYP2C9, CYP2C19, CYP2D6 and CYP3A4) Activity A total of five specific probe substrates for the five isozymes of CYP, phenacetin (CYP1A2), diclofenac (CYP2C9), (S')-mephenytoin (CYP2C19), dextromethorphan (CYP21D6), and midazolam (CYP3A4), were incubated respectively with human liver microsomes and the test compounds, and the reaction was initiated by the addition of reduced nicotinamide adenine dinucleotide phosphate (NADPH), and the samples were treated and the concentrations of the five metabolites produced by the specific substrates, acetaminophen, 4'-hydroxydiclofenac, 4'-hydroxymephenytoin, dextrorphan and 1'-hydroxymidazolam were measured by liquid chromatography tandem mass spectrometry (LC-MS/MS) after the end of the reaction, and the corresponding half maximal inhibitory concentrations ($IC_{50}$) were calculated.

TABLE 2

| | $IC_{50}$ (μM) | | | | |
|---|---|---|---|---|---|
| Compound number | CYP1A2 | CYP2C9 | CYP2C19 | CYP2D6 | CYP3A4-M |
| Reference compounds (Cenicriviroc) | >50 | >50 | >50 | >50 | 0.75 |
| Reference A | >50 | >50 | >50 | >50 | 0.786 |
| WX007 | >50 | >50 | >50 | >50 | >50 |
| WX009 | >50 | >50 | >50 | >50 | 4.6 |
| WX012 | >50 | 22.6 | 10.1 | >50 | >50 |

Experimental conclusion: WX007, WX009, WX012 show no risk of inhibition of human liver microsomal cytochrome P450 isozymes (CYP1A2, CYP2B6, CYP2C8, CYP2C9, CYP2C19, CYP2D6 and CYP3A4) activity, while the reference compounds and reference A show strong inhibition of CYP3A4.

Experimental Embodiment 3 Comparative Pharmacokinetic Test in Mice

C57BL/6 male mice were used as test animals in the present study, and the plasma drug concentrations of the test compound WX009 and the reference compound in mice by intravenous administration or oral administration were quantified by LC/MS/MS method at different time points respectively to evaluate the pharmacokinetic characteristics of the two test drugs in mice.

A clarified solution of the test compound was injected via tail vein into C57BL/6 mice (overnight fasting, 7-10 weeks old), and the test compound was given by gavage into C57BL/6 mice (overnight fasting, 7-10 weeks old). Approximately 30 μL of blood was collected from the jugular or tail vein at 0.0833, 0.25, 0.5, 1, 2, 4, 6, 8, and 24 hours after administration, and placed in anticoagulation tubes added with EDTA-K2, then centrifuged at 4° C. for 15 minutes at 3000 g to give the plasma. Plasma drug concentration was determined by LC-MS/MS, and relevant pharmacokinetic parameters were calculated using WinNonlin™ Version 6.3 (Pharsight, Mountain View, CA) pharmacokinetic software with a non-compartmental model linear logarithmic trapezoidal method.

TABLE 3

Pharmacokinetic parameters of test compound WX009 and reference compounds in mice

| Pharmacokinetic parameters in mice | Intravenous injection (2 mg/kg) Plasma clearance rate (mL/min/kg) | Intravenous injection (2 mg/kg) Half-life (h) | Oral (10 mg/kg) Peak concentration (nM) | Oral (10 mg/kg) Peak time (h) | Oral (10 mg/kg) Area under the time-concentration curve (0-inf, nM · h) | Bioavailability |
|---|---|---|---|---|---|---|
| Reference compounds (Cenicriviroc) | 2.28 | 3.55 | 1533 | 1.0 | 6401 | 6.02 |
| WX009 | 0.46 | 4.4 | 5076 | 2.0 | 37356 | 8% |

Conclusion: The plasma clearance rate of WX009 is slower than that of the reference compound; the oral plasma systemic exposure ($AUC_{0\text{-}inf}$) is approximately six times higher than that of the reference compound. In rodent mice, the pharmacokinetics of WX009 is significantly better than that of the reference compound.

The invention claimed is:

1. A compound represented by formula (I) or a pharmaceutically acceptable salt thereof, (I)

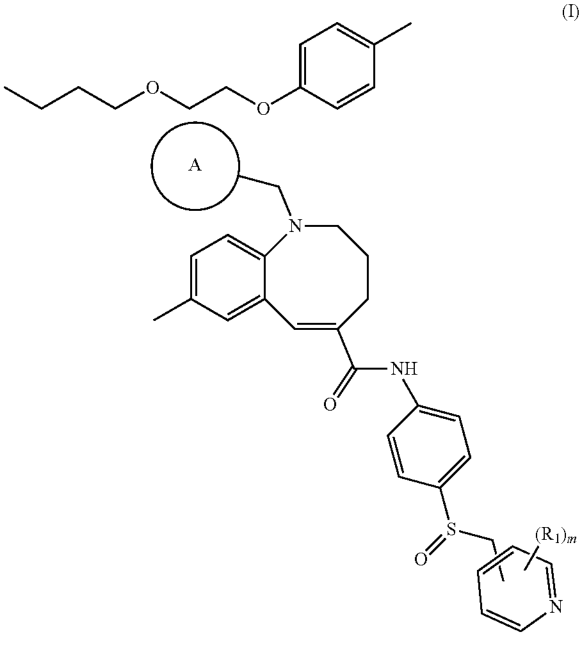

wherein, each of $R_1$ is independently selected from halogen, OH, $NH_2$, CN, $C_{1-3}$ alkyl and $C_{1-3}$ alkoxy, and the $C_{1-3}$ alkyl and $C_{1-3}$ alkoxy are optionally substituted by 1, 2 or 3 F;

m is selected from 0, 1 and 2;

ring A is selected from 5- to 6-membered heterocycloalkyl;

where the heterocycloalkyl contains 1, 2 or 3 heteroatoms or heteroatom groups independently selected from —O—, —NH—, —S—and N.

2. The compound as claimed in claim 1 or the pharmaceutically acceptable salt thereof, wherein, each of $R_1$ is independently selected from halogen, OH, $NH_2$, CN, $C_{1-3}$ alkyl and $C_{1-3}$ alkoxy.

3. The compound as claimed in claim 2 or the pharmaceutically acceptable salt thereof, wherein, each of $R_1$ is independently selected from methyl, ethyl and n-propyl.

4. The compound as claimed in claim 1 or the pharmaceutically acceptable salt thereof, wherein, ring A is selected from

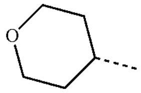 , 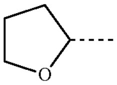 and 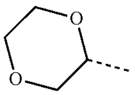 .

5. The compound as claimed in claim 1 or the pharmaceutically acceptable salt thereof, wherein, the structural moiety

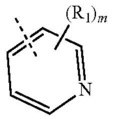

is selected from

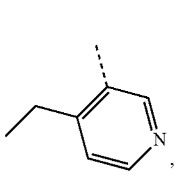 , 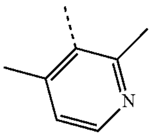 , 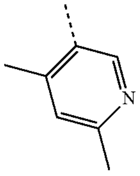 ,

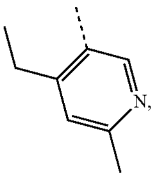 , 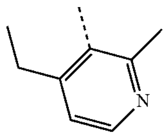 and

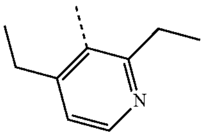 .

6. A compound represented by the following formula or a pharmaceutically acceptable salt thereof, selected from:
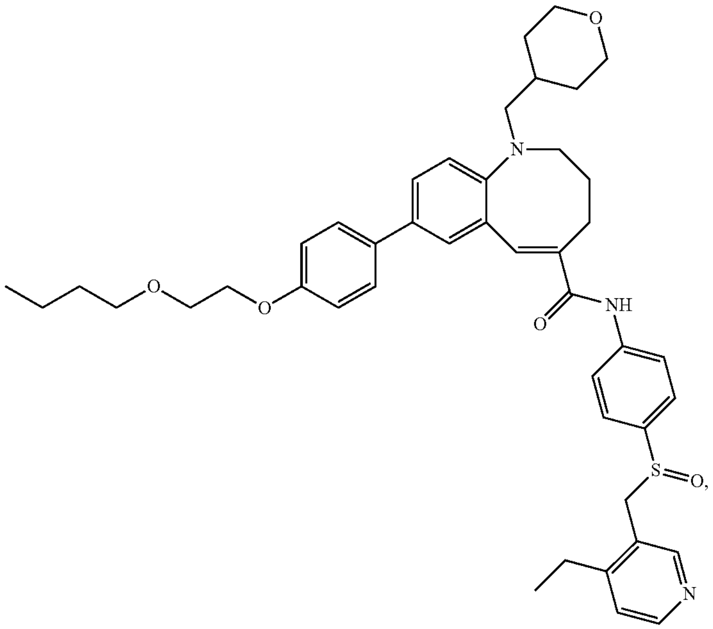
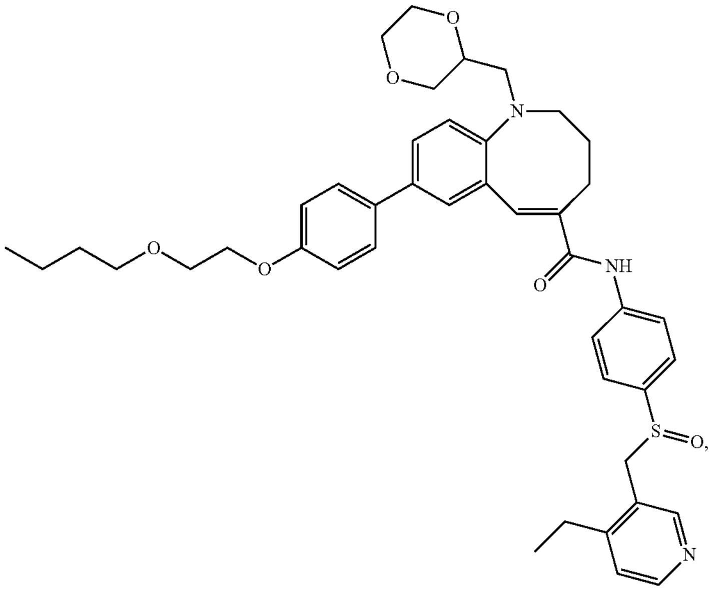

-continued
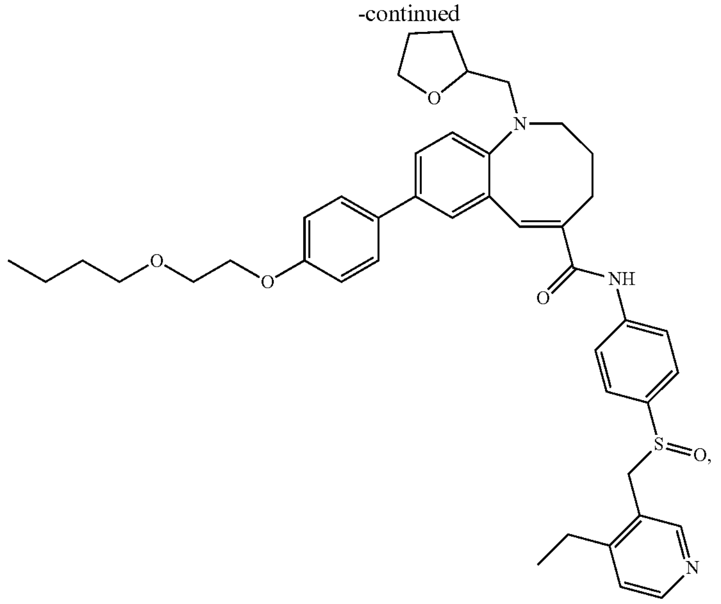
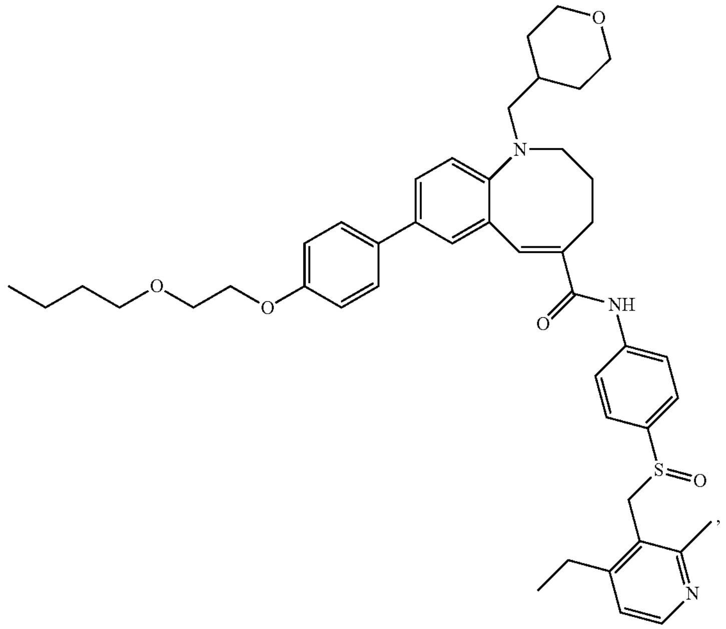

-continued
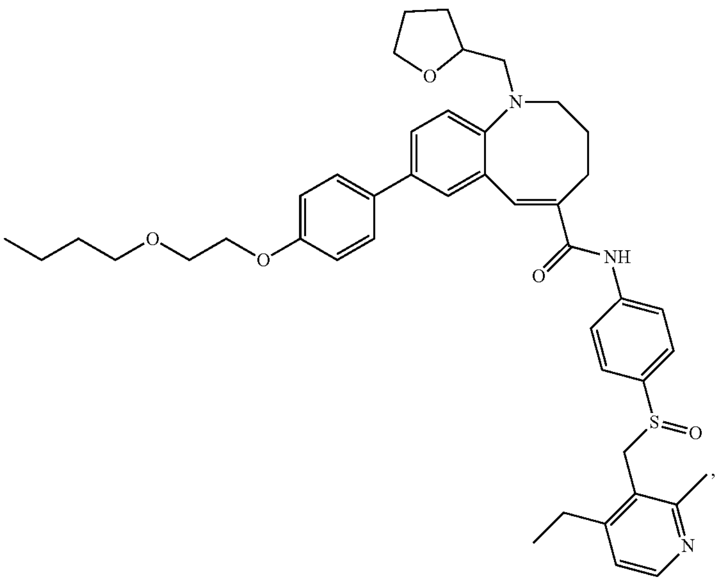
,
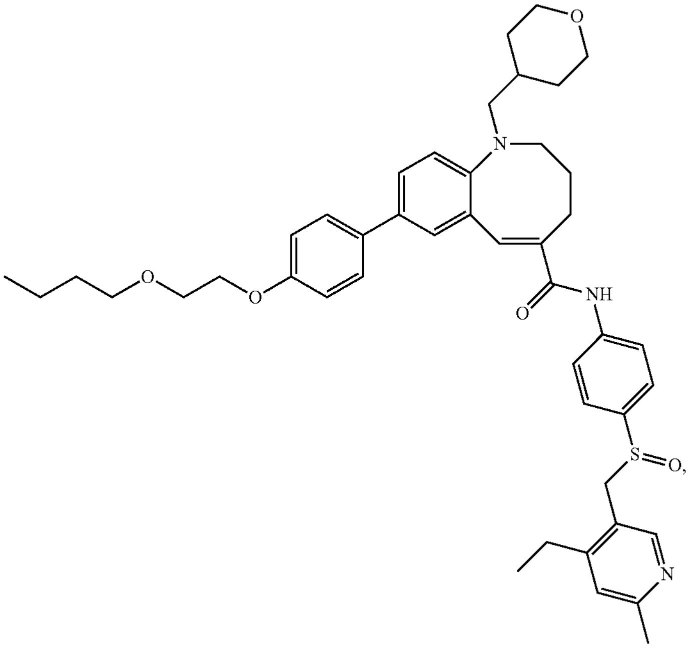
,

-continued
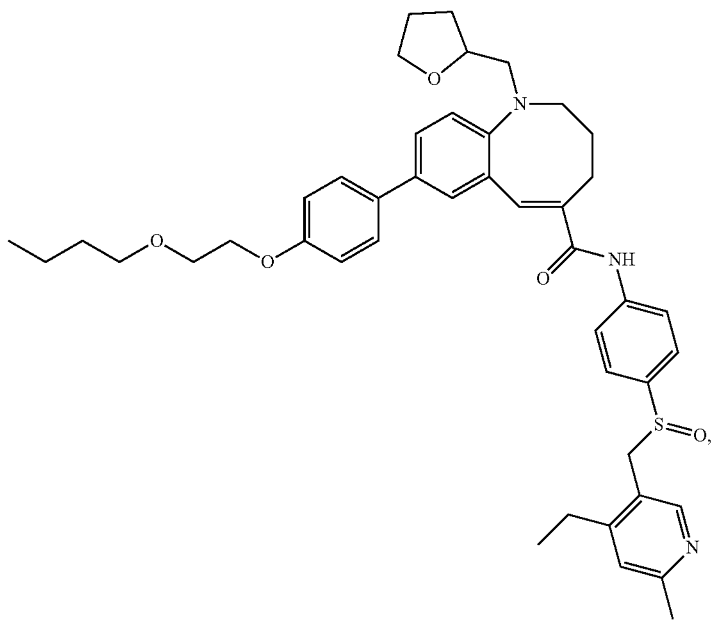
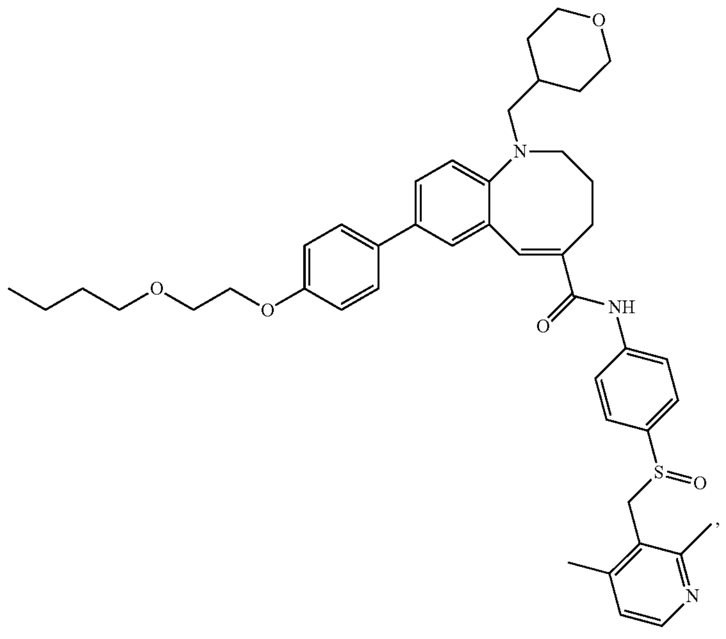

-continued
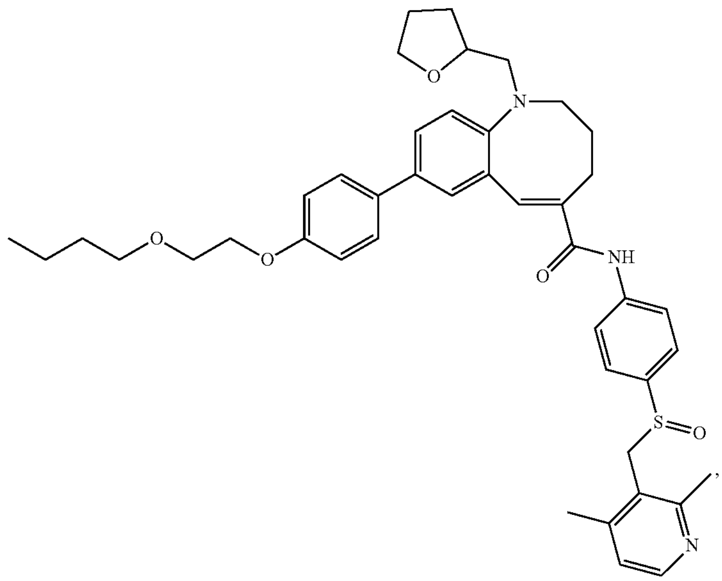
,
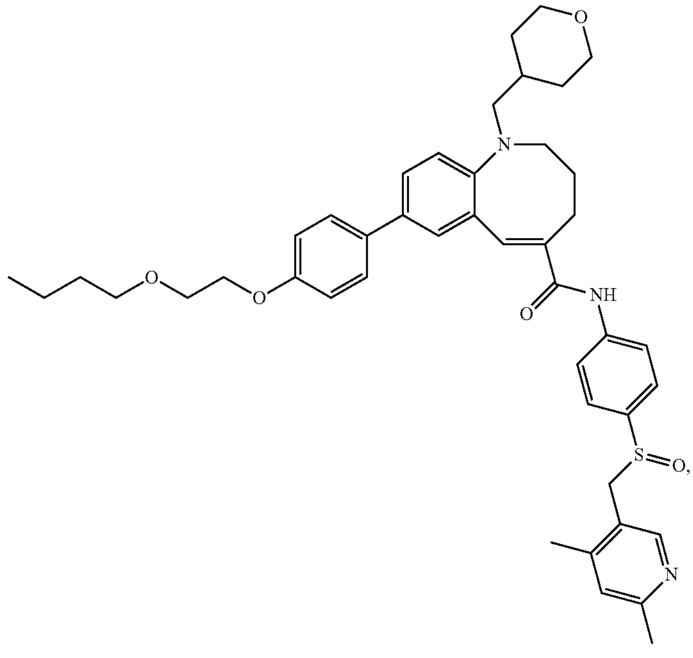
,

-continued
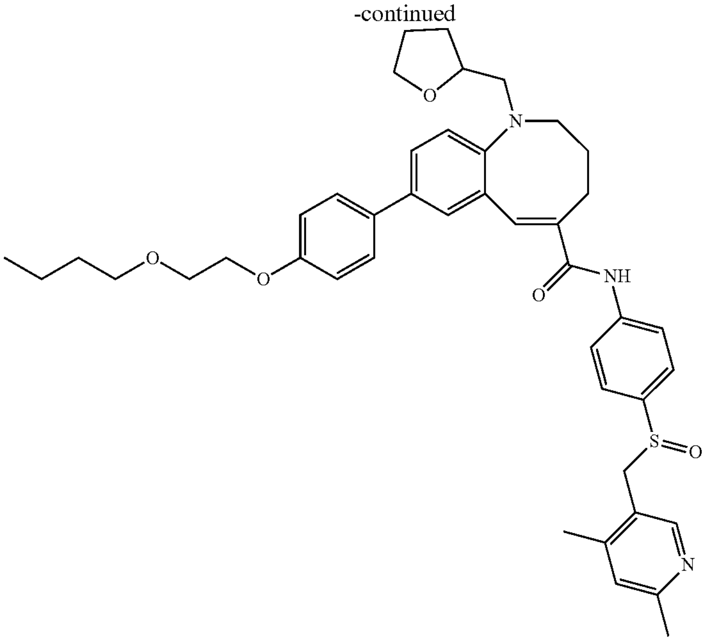
and
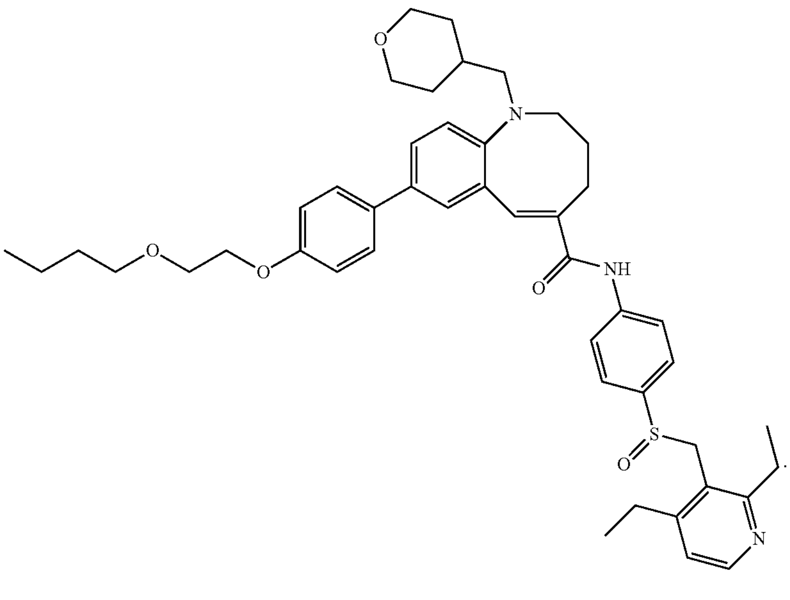
.

7. The compound as claimed in claim 6 or the pharmaceutically acceptable salt thereof, selected from:
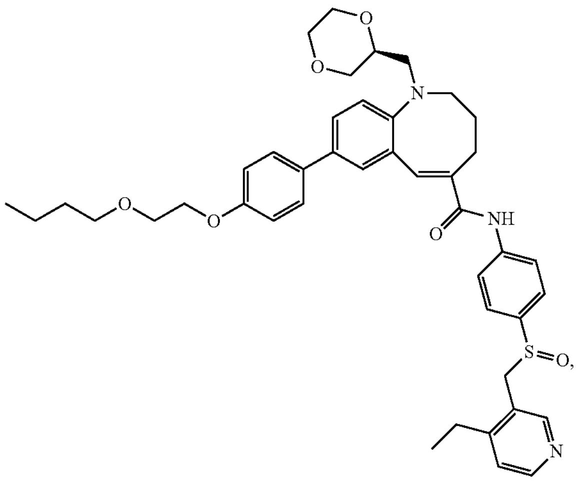
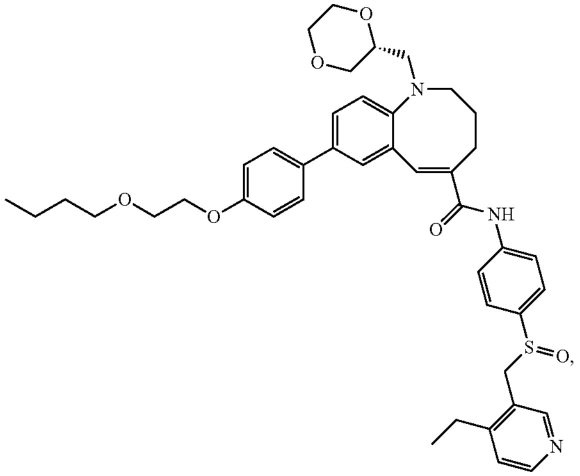
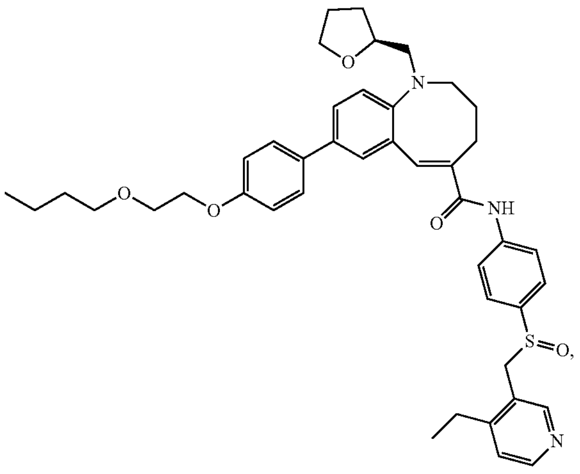
-continued
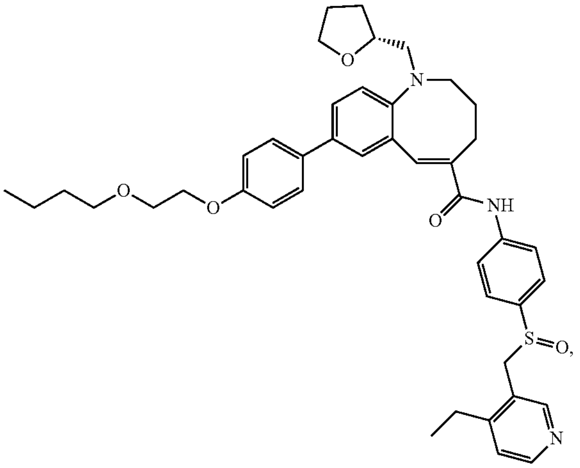
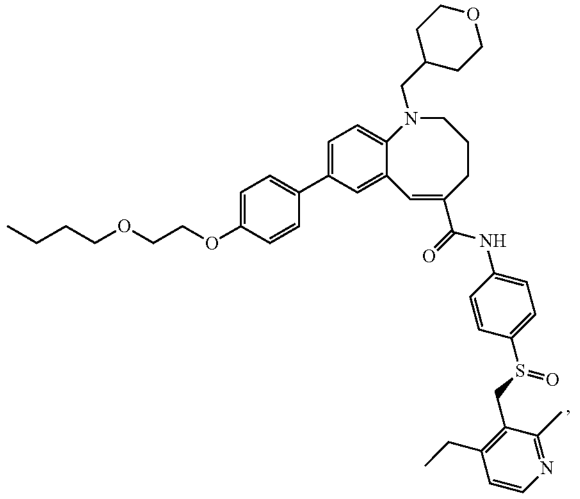
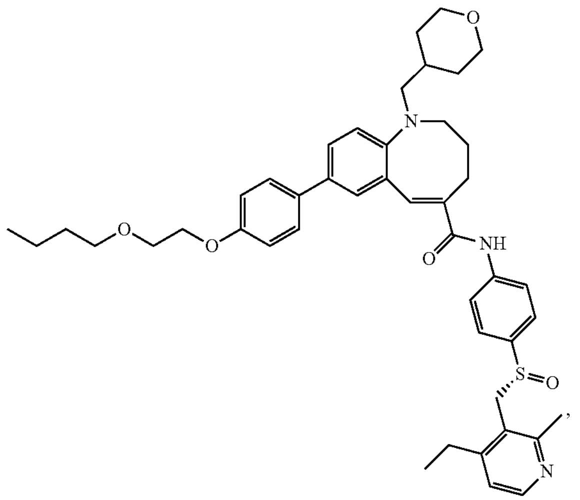

-continued
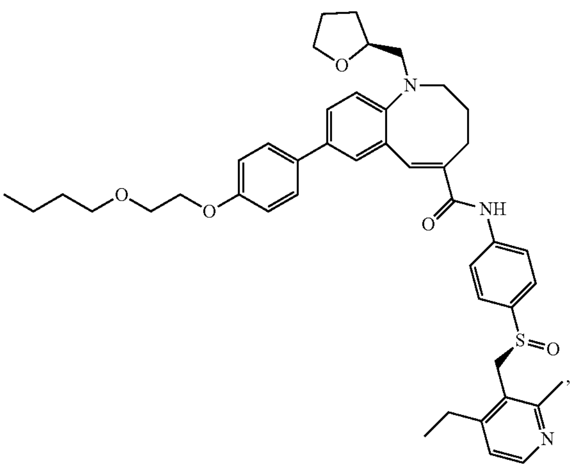
,
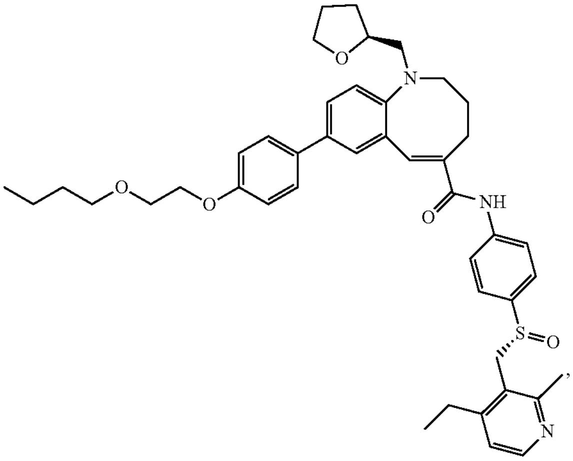
,
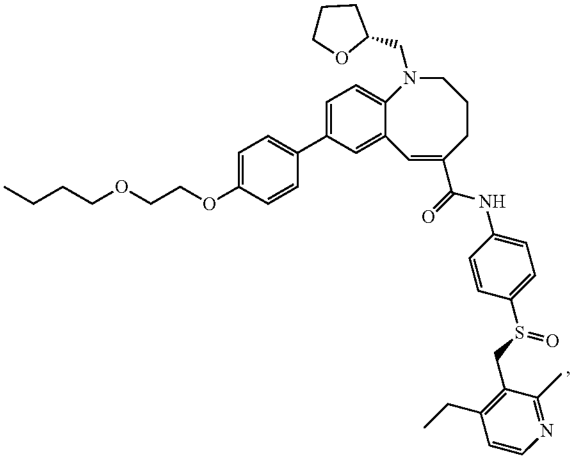
,
-continued
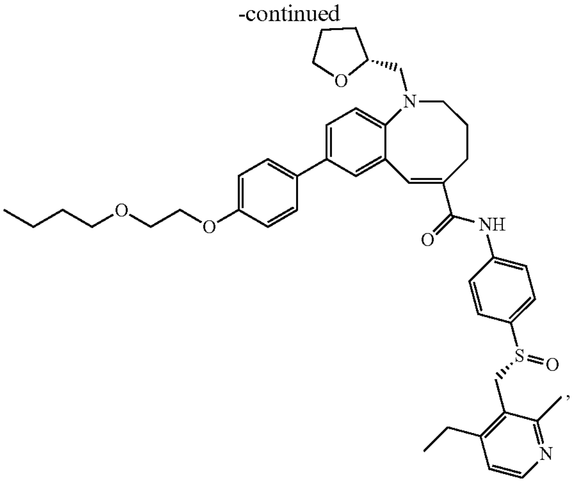
,
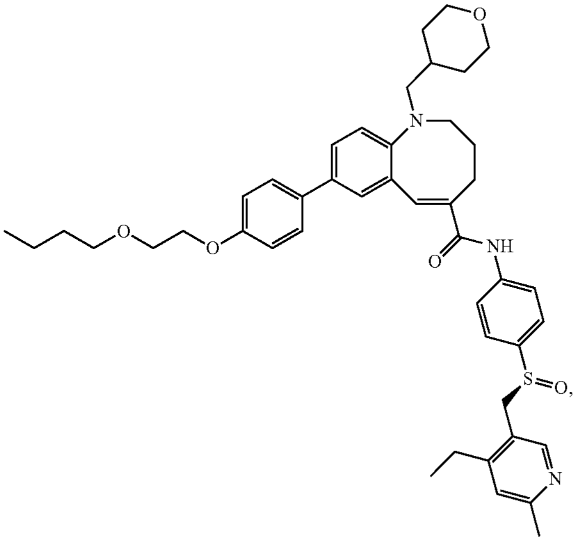
,
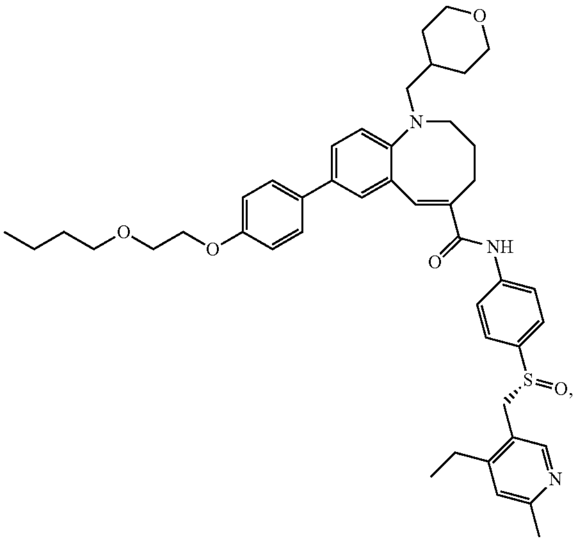
, -continued
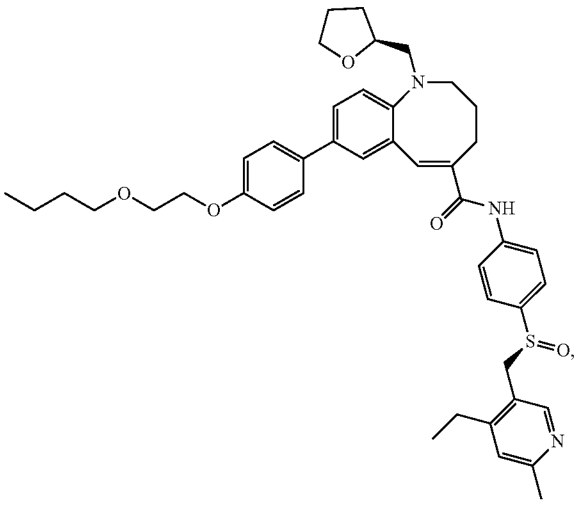
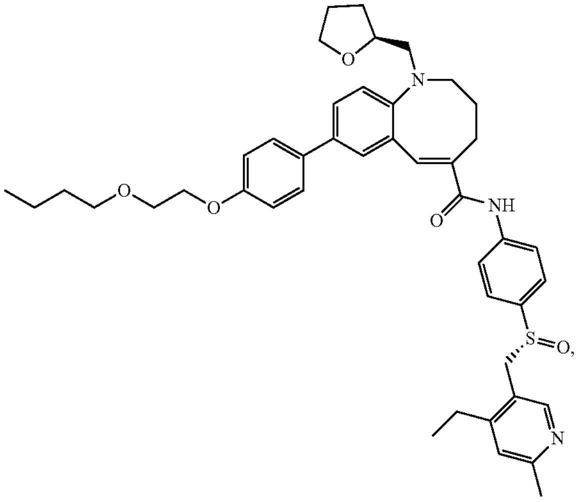
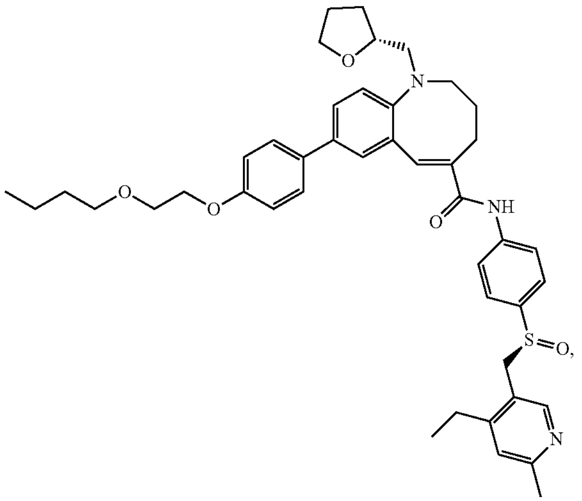
-continued
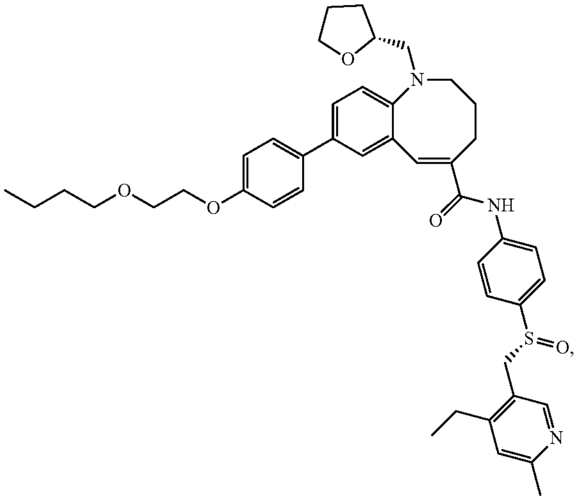
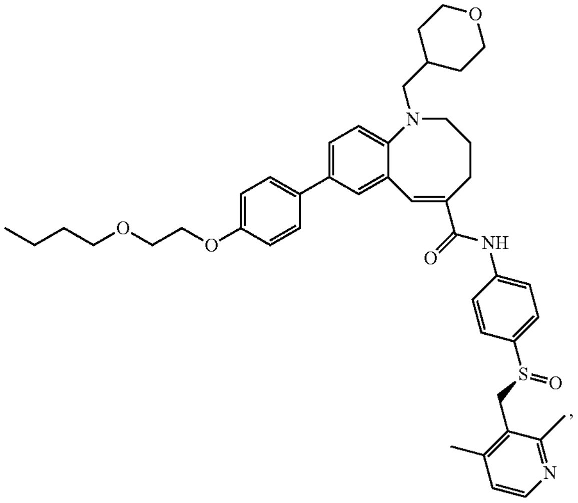
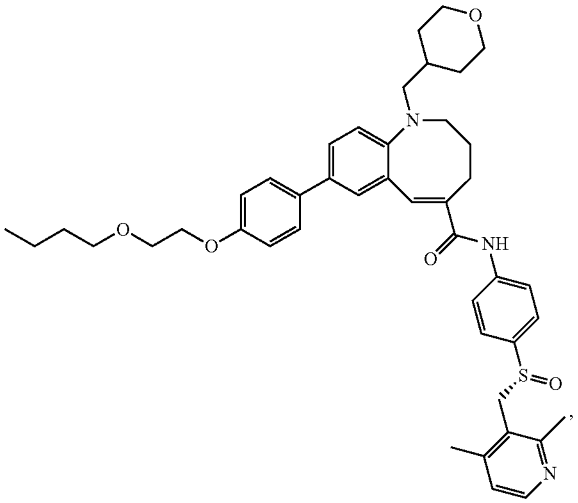

-continued
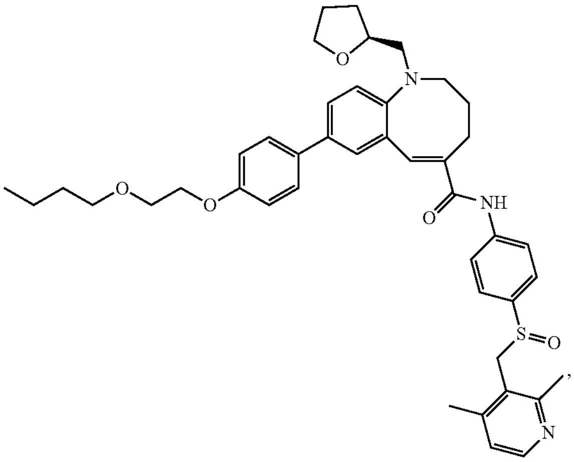
,
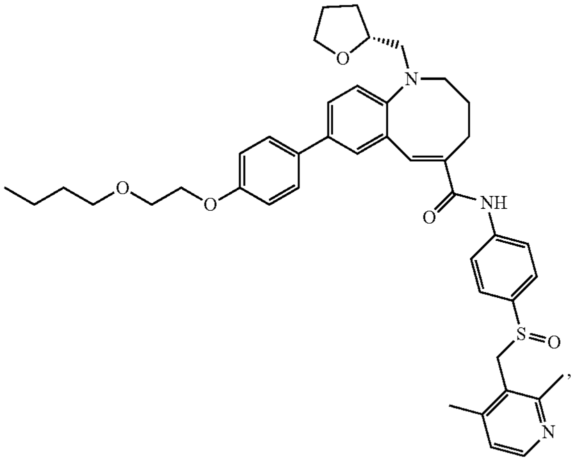
,
-continued
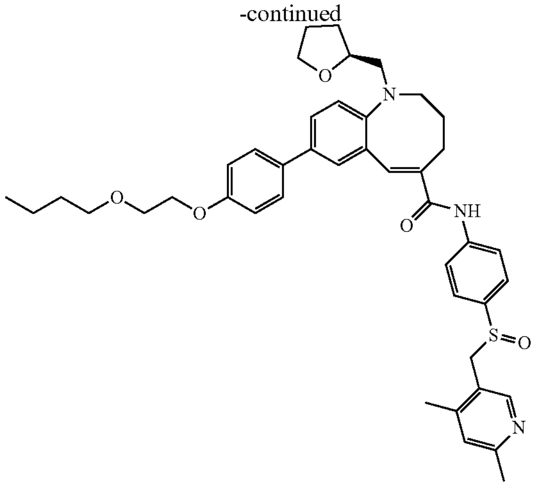
and
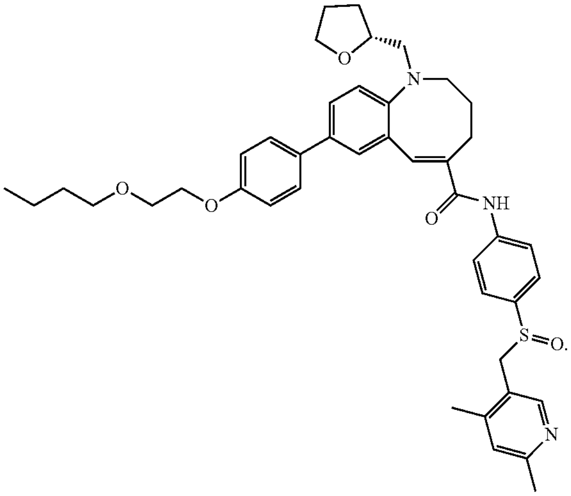
8. A method for antagonizing a CCR2/CCR5 dual receptor in a subject in need thereof, comprising: administering to the subject an effective amount of a compound as claimed in claim 1 or a pharmaceutically acceptable salt thereof.
* * * * *